(12) United States Patent
Burnett et al.

(10) Patent No.: US 7,368,562 B2
(45) Date of Patent: May 6, 2008

(54) SUBSTITUTED AZETIDINONE COMPOUNDS, PROCESSES FOR PREPARING THE SAME, FORMULATIONS AND USES THEREOF

(75) Inventors: Duane A. Burnett, Bernardsville, NJ (US); John W. Clader, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/705,977

(22) Filed: Feb. 13, 2007

(65) Prior Publication Data

US 2007/0155674 A1    Jul. 5, 2007

Related U.S. Application Data

(62) Division of application No. 10/791,979, filed on Mar. 3, 2004, now Pat. No. 7,192,944.

(60) Provisional application No. 60/452,722, filed on Mar. 7, 2003.

(51) Int. Cl.
| C07H 7/02 | (2006.01) |
| A61K 31/7052 | (2006.01) |
| A61P 9/10 | (2006.01) |
| A61P 3/06 | (2006.01) |
| A61P 25/28 | (2006.01) |
| C07D 205/08 | (2006.01) |
| A61K 31/397 | (2006.01) |
| C07K 2/00 | (2006.01) |

(52) U.S. Cl. ..................... 536/29.11; 514/23
(58) Field of Classification Search ............. 536/29.11; 514/23
See application file for complete search history.

(56) References Cited

U.S. PATENT DOCUMENTS

| 2,809,194 A | 10/1957 | Novello |
| 3,108,097 A | 10/1963 | Ugi |
| 3,152,173 A | 10/1964 | Ehrhart |
| 3,267,104 A | 8/1966 | Hermans |
| 3,399,192 A | 8/1968 | Regnler |
| 3,692,895 A | 9/1972 | Nelson |
| 3,716,583 A | 2/1973 | Nakamura |
| 3,781,328 A | 12/1973 | Witte |
| 3,948,973 A | 4/1976 | Phillips |
| 4,072,705 A | 2/1978 | Mieville |
| 4,075,000 A | 2/1978 | Abdulla |
| 4,144,232 A | 3/1979 | Koppel |
| 4,148,923 A | 4/1979 | Giudicelli |
| 4,166,907 A | 9/1979 | Krapcho |
| 4,178,695 A | 12/1979 | Erbeia |
| 4,179,515 A | 12/1979 | Mieville |
| 4,235,896 A | 11/1980 | Mieville |
| 4,239,763 A | 12/1980 | Milavec |
| 4,250,191 A | 2/1981 | Edwards |
| 4,260,743 A | 4/1981 | Bose |
| 4,304,718 A | 12/1981 | Kamiya |
| 4,375,475 A | 3/1983 | Willard |
| 4,443,372 A | 4/1984 | Luo |
| 4,444,784 A | 4/1984 | Hoffman |
| 4,472,309 A | 9/1984 | Kamiya |
| 4,479,900 A | 10/1984 | Luo |
| 4,500,456 A | 2/1985 | Spitzer |
| 4,534,786 A | 8/1985 | Luo |
| 4,564,609 A | 1/1986 | Tamura |
| 4,567,195 A | 1/1986 | Schwarz |
| 4,576,748 A | 3/1986 | Greenlee |
| 4,576,749 A | 3/1986 | Zahler |
| 4,576,753 A | 3/1986 | Kamiya |
| 4,581,170 A | 4/1986 | Mueller |

(Continued)

FOREIGN PATENT DOCUMENTS

BE    884722 A    12/1980

(Continued)

OTHER PUBLICATIONS

*Exhibit A*: SCH 58235 Micronized (ezetimibe), Drug Formulation Development Summary.

(Continued)

*Primary Examiner*—Mark L Berch
(74) *Attorney, Agent, or Firm*—Mark W. Russell

(57) ABSTRACT

The present invention provides compounds represented by the structural formula (I):

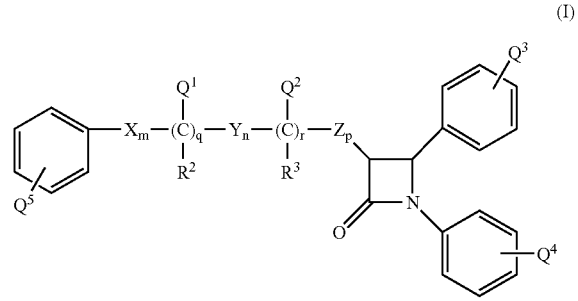

or pharmaceutically acceptable isomers, salts, solvates or esters of the compound of Formula (I), wherein each of the substituents is as specified herein, formulations including the above compounds, processes for preparing the same and methods for treating vascular conditions, such as atherosclerosis or hypercholesterolemia diabetes, obesity, stroke, demyelination and lowering plasma levels of sterols and/or stanols.

32 Claims, No Drawings

U.S. PATENT DOCUMENTS

| | | |
|---|---|---|
| 4,595,532 A | 6/1986 | Miller |
| 4,602,003 A | 7/1986 | Malinow |
| 4,602,005 A | 7/1986 | Malinow |
| 4,614,614 A | 9/1986 | Ernest |
| 4,616,047 A | 10/1986 | Lafon |
| 4,620,867 A | 11/1986 | Luo |
| 4,626,549 A | 12/1986 | Molloy |
| 4,633,017 A | 12/1986 | Mueller |
| 4,642,903 A | 2/1987 | Davies |
| 4,654,362 A | 3/1987 | Lommen |
| 4,675,399 A | 6/1987 | Miller |
| 4,680,289 A | 7/1987 | Applezweig |
| 4,680,391 A | 7/1987 | Firestone |
| 4,687,777 A | 8/1987 | Meguro |
| 4,739,101 A | 4/1988 | Bourgogne |
| 4,778,883 A | 10/1988 | Yoshioka |
| 4,784,734 A | 11/1988 | Torii |
| 4,794,108 A | 12/1988 | Kishimoto |
| 4,800,079 A | 1/1989 | Boyer |
| 4,803,266 A | 2/1989 | Kawashima |
| 4,814,354 A | 3/1989 | Ghebre-Sellassie |
| 4,834,846 A | 5/1989 | Abramson |
| 4,871,752 A | 10/1989 | Ilg et al. |
| 4,876,365 A | 10/1989 | Kirkup |
| 4,879,301 A | 11/1989 | Umio |
| 4,895,726 A | 1/1990 | Curtet |
| 4,925,672 A | 5/1990 | Gremm |
| 4,937,267 A | 6/1990 | Holloway |
| 4,939,248 A | 7/1990 | Yoshioka |
| 4,952,689 A | 8/1990 | Kawashima |
| 4,961,890 A | 10/1990 | Boyer |
| 4,983,597 A | 1/1991 | Yang |
| 4,990,535 A | 2/1991 | Cho |
| 5,021,461 A | 6/1991 | Robinson |
| 5,030,628 A | 7/1991 | Joyeau |
| 5,073,374 A | 12/1991 | McCarty |
| 5,091,525 A | 2/1992 | Brennan |
| 5,093,365 A | 3/1992 | Berge |
| 5,099,034 A | 3/1992 | Yoshida |
| 5,100,675 A | 3/1992 | Cho |
| 5,106,833 A | 4/1992 | Broze |
| 5,110,730 A | 5/1992 | Edgington |
| 5,112,616 A | 5/1992 | McCarty |
| 5,120,713 A | 6/1992 | Mugica |
| 5,120,729 A | 6/1992 | Chabala |
| 5,130,333 A | 7/1992 | Pan |
| 5,145,684 A | 9/1992 | Liversidge |
| 5,157,025 A | 10/1992 | Aberg |
| 5,162,117 A | 11/1992 | Stupak |
| 5,178,878 A | 1/1993 | Wehling |
| 5,188,825 A | 2/1993 | Iles |
| 5,190,970 A | 3/1993 | Pan |
| 5,204,461 A | 4/1993 | Murayama |
| 5,219,574 A | 6/1993 | Wehling |
| 5,223,264 A | 6/1993 | Wehling |
| 5,229,362 A | 7/1993 | Kirst |
| 5,229,381 A | 7/1993 | Doherty |
| 5,229,510 A | 7/1993 | Knight |
| 5,260,305 A | 11/1993 | Dennick |
| 5,278,176 A | 1/1994 | Lin |
| H001286 H | 2/1994 | Eisman |
| 5,286,631 A | 2/1994 | Boeck |
| 5,298,497 A | 3/1994 | Tschollar |
| 5,306,817 A | 4/1994 | Thiruvengadam |
| 5,318,767 A | 6/1994 | Liversidge |
| 5,348,953 A | 9/1994 | Doherty |
| 5,350,868 A | 9/1994 | Yoshida |
| 5,358,852 A | 10/1994 | Wu |
| 5,384,124 A | 1/1995 | Courtelle |
| 5,385,885 A | 1/1995 | Gasic |
| 5,399,363 A | 3/1995 | Liversidge |
| 5,401,513 A | 3/1995 | Wehling |
| 5,412,092 A | 5/1995 | Rey |
| 5,429,824 A | 7/1995 | June |
| 5,446,464 A | 8/1995 | Feldle |
| 5,461,039 A | 10/1995 | Tschollar |
| 5,464,632 A | 11/1995 | Cousin |
| 5,494,683 A | 2/1996 | Liversidge |
| 5,503,846 A | 4/1996 | Wehling |
| 5,510,118 A | 4/1996 | Bosch |
| 5,510,466 A | 4/1996 | Krieger |
| 5,518,187 A | 5/1996 | Bruno |
| 5,518,738 A | 5/1996 | Eickhoff |
| 5,545,628 A | 8/1996 | Deboeck |
| 5,550,229 A | 8/1996 | Iwasaki |
| 5,552,160 A | 9/1996 | Liversidge |
| 5,561,227 A | 10/1996 | Thiruvengadam |
| 5,563,264 A | 10/1996 | Kume |
| 5,567,439 A | 10/1996 | Myers |
| 5,576,014 A | 11/1996 | Mizumoto |
| 5,587,172 A | 12/1996 | Cherukuri |
| 5,587,180 A | 12/1996 | Allen |
| 5,591,456 A | 1/1997 | Franson |
| 5,593,971 A | 1/1997 | Tschollar |
| 5,595,761 A | 1/1997 | Allen |
| 5,607,697 A | 3/1997 | Alkire |
| 5,612,353 A | 3/1997 | Ewing |
| 5,612,367 A | 3/1997 | Timko |
| 5,612,378 A | 3/1997 | Tianbao |
| 5,618,707 A | 4/1997 | Homann |
| 5,622,719 A | 4/1997 | Myers |
| 5,622,985 A | 4/1997 | Olukotun |
| 5,624,920 A | 4/1997 | McKittrick |
| 5,627,176 A | 5/1997 | Kirkup |
| 5,631,023 A | 5/1997 | Kearney |
| 5,631,365 A | 5/1997 | Rosenblum |
| 5,633,246 A | 5/1997 | McKittrick |
| 5,635,210 A | 6/1997 | Allen |
| 5,639,475 A | 6/1997 | Bettman |
| 5,639,739 A | 6/1997 | Dominguez |
| 5,656,624 A | 8/1997 | Vaccaro |
| 5,661,145 A | 8/1997 | Davis |
| 5,674,893 A | 10/1997 | Behounek |
| 5,688,785 A | 11/1997 | Vaccaro |
| 5,688,787 A | 11/1997 | Burnett |
| 5,688,990 A | 11/1997 | Shankar |
| 5,691,375 A | 11/1997 | Behounek |
| 5,698,527 A | 12/1997 | Kim |
| 5,698,548 A | 12/1997 | Dugar |
| 5,703,188 A | 12/1997 | Mandeville |
| 5,703,234 A | 12/1997 | Iwasaki |
| 5,709,886 A | 1/1998 | Bettman |
| 5,718,388 A | 2/1998 | Czekai |
| 5,728,827 A | 3/1998 | Thiruvengadam et al. |
| 5,734,077 A | 3/1998 | Regnier |
| 5,739,321 A | 4/1998 | Wu |
| 5,744,467 A | 4/1998 | McKittrick |
| 5,747,001 A | 5/1998 | Wiedmann |
| 5,753,254 A | 5/1998 | Khan |
| 5,756,470 A | 5/1998 | Yumibe |
| 5,759,865 A | 6/1998 | Bruns |
| 5,767,115 A | 6/1998 | Rosenblum |
| 5,776,491 A | 7/1998 | Allen |
| 5,807,576 A | 9/1998 | Allen |
| 5,807,577 A | 9/1998 | Quali |
| 5,807,578 A | 9/1998 | Acosta-Cuello |
| 5,807,834 A | 9/1998 | Morehouse |
| 5,808,056 A | 9/1998 | Amato |
| 5,817,806 A | 10/1998 | Rossi |
| 5,827,536 A | 10/1998 | Laruelle |
| 5,827,541 A | 10/1998 | Yarwood |
| 5,831,091 A | 11/1998 | Ohmizu |
| 5,843,984 A | 12/1998 | Clay |
| 5,846,966 A | 12/1998 | Rosenblum |

| | | | | | | |
|---|---|---|---|---|---|---|
| 5,847,008 | A | 12/1998 | Doebber | 6,245,743 | B1 | 6/2001 | Marlowe |
| 5,847,115 | A | 12/1998 | Iwasaki | 6,248,781 | B1 | 6/2001 | Jeppesen |
| 5,851,553 | A | 12/1998 | Myers | 6,251,852 | B1 | 6/2001 | Gould |
| 5,856,473 | A | 1/1999 | Shankar | 6,262,042 | B1 | 7/2001 | Cook |
| 5,858,409 | A | 1/1999 | Karetny | 6,262,047 | B1 | 7/2001 | Zhu |
| 5,859,051 | A | 1/1999 | Adams | 6,262,098 | B1 | 7/2001 | Huebner |
| 5,862,999 | A | 1/1999 | Czekai | 6,277,584 | B1 | 8/2001 | Chu |
| 5,866,163 | A | 2/1999 | Myers | 6,277,831 | B1 * | 8/2001 | Frick et al. .................... 514/43 |
| 5,869,098 | A | 2/1999 | Misra | 6,316,029 | B1 | 11/2001 | Jain |
| 5,871,781 | A | 2/1999 | Myers | RE37,721 | E | 5/2002 | Rosenblum |
| 5,880,148 | A | 3/1999 | Edgar | 2001/0028895 | A1 | 10/2001 | Bisgaier |
| 5,883,109 | A | 3/1999 | Gregg | 2002/0006919 | A1 | 1/2002 | Thosar |
| 5,886,171 | A | 3/1999 | Wu | 2002/0039774 | A1 | 4/2002 | Kramer |
| 5,919,672 | A | 7/1999 | Homann | 2002/0128252 | A1 | 9/2002 | Glombik |
| 5,925,333 | A | 7/1999 | Krieger | 2002/0128253 | A1 | 9/2002 | Glombik |
| 5,952,003 | A | 9/1999 | Guentensberger | 2002/0132855 | A1 | 9/2002 | Nelson |
| 5,952,321 | A | 9/1999 | Doherty | 2002/0137689 | A1 | 9/2002 | Glombik |
| 5,959,123 | A | 9/1999 | Singh | 2002/0147184 | A1 | 10/2002 | Kosoglou et al. |
| 5,972,389 | A | 10/1999 | Shell | 2002/0151536 | A1 | 10/2002 | Davis et al. |
| 5,976,570 | A | 11/1999 | Greaves | 2002/0169134 | A1 | 11/2002 | Davis |
| 5,985,936 | A | 11/1999 | Novak | 2002/0183305 | A1 | 12/2002 | Davis et al. |
| 5,990,102 | A | 11/1999 | Hickey | 2002/0192203 | A1 | 12/2002 | Cho et al. |
| 5,994,554 | A | 11/1999 | Kliewer | 2003/0013699 | A1 | 1/2003 | Davis et al. |
| 5,998,441 | A | 12/1999 | Palkowitz | 2003/0013729 | A1 | 1/2003 | Iqbal |
| 6,008,237 | A | 12/1999 | Sahoo | 2003/0053981 | A1 | 3/2003 | Davis et al. |
| 6,027,747 | A | 2/2000 | Terracol | 2003/0069221 | A1 | 4/2003 | Kosoglou et al. |
| 6,028,109 | A | 2/2000 | Wilson | 2003/0105028 | A1 | 6/2003 | Ghosal et al. |
| 6,030,990 | A | 2/2000 | Maeda | 2003/0119428 | A1 | 6/2003 | Davis et al. |
| 6,033,656 | A | 3/2000 | Mikami | 2003/0119757 | A1 | 6/2003 | Davis |
| 6,040,147 | A | 3/2000 | Ridker | 2003/0119796 | A1 | 6/2003 | Strony |
| 6,043,257 | A | 3/2000 | Dominguez | 2003/0119808 | A1 | 6/2003 | LeBeaut et al. |
| 6,056,975 | A | 5/2000 | Mitra | 2003/0119809 | A1 | 6/2003 | Davis |
| 6,057,342 | A | 5/2000 | Fevig | 2003/0153541 | A1 | 8/2003 | Dudley |
| 6,063,764 | A | 5/2000 | Creasey | 2004/0180860 | A1 | 9/2004 | Burnett et al. |
| 6,066,653 | A | 5/2000 | Gregg | 2004/0198700 | A1 | 10/2004 | Burnett et al. |
| 6,071,899 | A | 6/2000 | Hickey | | | | |
| 6,074,670 | A | 6/2000 | Stamm | | | | |
| 6,080,767 | A | 6/2000 | Klein | | | | |
| 6,080,778 | A | 6/2000 | Yankner | | | | |
| 6,084,082 | A | 7/2000 | Ravikumar | | | | |
| 6,090,830 | A | 7/2000 | Myers | | | | |
| 6,090,839 | A | 7/2000 | Adams | | | | |
| 6,093,812 | A | 7/2000 | Thiruvengadam | | | | |
| 6,096,883 | A | 8/2000 | Wu | | | | |
| 6,099,865 | A | 8/2000 | Augello | | | | |
| 6,103,705 | A | 8/2000 | Uzan | | | | |
| 6,110,493 | A | 8/2000 | Guentensberger | | | | |
| 6,117,429 | A | 9/2000 | Bucci | | | | |
| 6,121,319 | A | 9/2000 | Somers | | | | |
| 6,127,424 | A | 10/2000 | Martin | | | | |
| 6,133,001 | A | 10/2000 | Homann | | | | |
| 6,139,873 | A | 10/2000 | Hughes | | | | |
| 6,140,354 | A | 10/2000 | Dax | | | | |
| 6,143,885 | A | 11/2000 | Choi | | | | |
| 6,147,090 | A | 11/2000 | DeNinno | | | | |
| 6,147,109 | A | 11/2000 | Liao | | | | |
| 6,147,250 | A | 11/2000 | Somers | | | | |
| 6,159,997 | A | 12/2000 | Tsujita | | | | |
| 6,162,805 | A | 12/2000 | Hefti | | | | |
| 6,166,049 | A | 12/2000 | Smith | | | | |
| 6,174,665 | B1 | 1/2001 | Dullien | | | | |
| 6,180,138 | B1 | 1/2001 | Engh | | | | |
| 6,180,625 | B1 | 1/2001 | Persson | | | | |
| 6,180,660 | B1 | 1/2001 | Whitney | | | | |
| 6,191,117 | B1 | 2/2001 | Kozachuk | | | | |
| 6,191,159 | B1 | 2/2001 | Pinto | | | | |
| 6,200,998 | B1 | 3/2001 | Sahoo | | | | |
| 6,207,697 | B1 | 3/2001 | Han | | | | |
| 6,207,699 | B1 | 3/2001 | Rothman | | | | |
| 6,207,822 | B1 | 3/2001 | Thiruvengadam | | | | |
| 6,214,831 | B1 | 4/2001 | Yokoo | | | | |
| 6,235,706 | B1 | 5/2001 | Gould | | | | |
| 6,242,605 | B1 | 6/2001 | Raveendranath | | | | |

FOREIGN PATENT DOCUMENTS

| | | |
|---|---|---|
| CA | 2253769 | 11/1999 |
| DE | 2046823 A | 3/1972 |
| DE | 2521113 A | 3/1976 |
| EP | 0002151 A1 | 5/1979 |
| EP | 0002151 B1 | 5/1979 |
| EP | 0010299 B1 | 2/1984 |
| EP | 0179559 A2 | 4/1986 |
| EP | 0199630 A1 | 10/1986 |
| EP | 0264231 A1 | 4/1988 |
| EP | 0266896 B1 | 5/1988 |
| EP | 0274873 B1 | 7/1988 |
| EP | 0288973 B1 | 11/1988 |
| EP | 0311366 B1 | 4/1989 |
| EP | 0333268 A1 | 9/1989 |
| EP | 0337549 A1 | 10/1989 |
| EP | 0365364 A2 | 4/1990 |
| EP | 0369686 A1 | 5/1990 |
| EP | 0375527 A1 | 6/1990 |
| EP | 0199630 B1 | 9/1990 |
| EP | 0401705 A3 | 12/1990 |
| EP | 0415487 A2 | 3/1991 |
| EP | 0455042 A1 | 11/1991 |
| EP | 0457514 A1 | 11/1991 |
| EP | 0461548 A3 | 12/1991 |
| EP | 0462667 A2 | 12/1991 |
| EP | 0475148 A1 | 3/1992 |
| EP | 0475755 B1 | 3/1992 |
| EP | 0481671 A1 | 4/1992 |
| EP | 0482498 A3 | 4/1992 |
| EP | 0524595 A1 | 1/1993 |
| EP | 0337549 B1 | 10/1995 |
| EP | 0720599 B1 | 7/1996 |
| EP | 0457514 B1 | 8/1996 |
| EP | 0 753 298 A1 | 1/1997 |
| EP | 0793958 A2 | 9/1997 |

| | | | | | |
|---|---|---|---|---|---|
| EP | 0814080 A1 | 12/1997 | WO | WO 98/46215 | 10/1998 |
| EP | 0904781 A2 | 3/1999 | WO | WO98/47518 | 10/1998 |
| EP | 1 036 563 A1 | 9/2000 | WO | WO 98/57652 | 12/1998 |
| EP | 1048295 A2 | 11/2000 | WO | WO 99/06035 | 2/1999 |
| FR | 1103113 | 10/1955 | WO | WO 99/06046 | 2/1999 |
| FR | 2779347 | 12/1997 | WO | WO 99/08501 | 2/1999 |
| GB | 861367 | 2/1961 | WO | WO 99/09967 | 3/1999 |
| GB | 902658 | 8/1962 | WO | WO 99/11260 | 3/1999 |
| GB | 1415295 | 11/1975 | WO | WO99/12534 | 3/1999 |
| GB | 2329334 A | 3/1999 | WO | WO 99/1 5520 | 4/1999 |
| JP | 136485 | 5/1981 | WO | WO 99/04815 | 4/1999 |
| JP | 028057 | 10/1981 | WO | WO 99/15159 | 4/1999 |
| JP | 180212 | 3/1986 | WO | WO 99/18072 | 4/1999 |
| JP | 121479 | 12/1986 | WO | WO 99/20275 | 4/1999 |
| JP | 61280295 A | 12/1986 | WO | WO 99/20614 | 4/1999 |
| JP | 219681 | 4/1987 | WO | WO 99/22728 A1 | 5/1999 |
| JP | 63017859 A | 1/1988 | WO | WO 99/29300 | 6/1999 |
| JP | 91068020 | 10/1991 | WO | WO 99/38498 | 8/1999 |
| JP | 4054182 A | 2/1992 | WO | WO 99/38845 | 8/1999 |
| JP | 4266869 A | 9/1992 | WO | WO 99/38850 | 8/1999 |
| JP | 4356195 A | 12/1992 | WO | WO 99/46232 | 9/1999 |
| JP | 4356495 | 12/1992 | WO | WO 99/47123 | 9/1999 |
| JP | 5058993 A | 3/1993 | WO | WO 99/48488 | 9/1999 |
| JP | 5194209 A | 8/1993 | WO | WO99/66929 | 12/1999 |
| JP | 5239020 A | 9/1993 | WO | WO 99/66930 | 12/1999 |
| JP | 94047573 | 6/1994 | WO | WO 00/04011 | 1/2000 |
| JP | 95051558 B2 | 6/1995 | WO | WO 00/1 8395 | 4/2000 |
| WO | WO 00/07617 | 2/0000 | WO | WO 00/20623 | 4/2000 |
| WO | WO 00/16749 | 3/0000 | WO | WO 00/23415 | 4/2000 |
| WO | WO 00/37057 | 6/0000 | WO | WO 00/23416 | 4/2000 |
| WO | WO 82/01649 | 5/1982 | WO | WO 00/23425 | 4/2000 |
| WO | WO 87/04429 | 7/1987 | WO | WO 00/23445 | 4/2000 |
| WO | WO 88/04656 | 6/1988 | WO | WO 00/23451 | 4/2000 |
| WO | WO 88/05296 | 7/1988 | WO | WO 00/28981 | 5/2000 |
| WO | WO 91/03249 | 3/1991 | WO | WO 00/31548 | 6/2000 |
| WO | WO 92/13837 | 8/1992 | WO | WO00/32189 | 6/2000 |
| WO | WO 93/02048 | 2/1993 | WO | WO 00/34240 | 6/2000 |
| WO | WO 93/07167 | 4/1993 | WO | WO 00/37078 | 6/2000 |
| WO | WO 93/11150 | 6/1993 | WO | WO 00/3 8722 | 7/2000 |
| WO | WO 94/00480 | 1/1994 | WO | WO 00/38 726 | 7/2000 |
| WO | WO 94/14433 | 7/1994 | WO | WO 00/38721 | 7/2000 |
| WO | WO 94/1 7038 | 8/1994 | WO | WO 00/38723 | 7/2000 |
| WO | WO 94/20535 | 9/1994 | WO | WO 00/38724 | 7/2000 |
| WO | WO 94/26738 | 11/1994 | WO | WO 00)38725 | 7/2000 |
| WO | WO 95/04533 | 2/1995 | WO | WO 00/38727 | 7/2000 |
| WO | WO 95/06470 | 3/1995 | WO | WO 00/38728 | 7/2000 |
| WO | WO 95/08532 | 3/1995 | WO | WO 00/38729 | 7/2000 |
| WO | WO 95/18143 | 7/1995 | WO | WO 00/40247 | 7/2000 |
| WO | WO 95/26334 | 10/1995 | WO | WO 00/45817 | 8/2000 |
| WO | WO95/28919 | 11/1995 | WO | WO 00/50392 | 8/2000 |
| WO | WO 95/35277 | 12/1995 | WO | WO 00/53149 | 9/2000 |
| WO | WO 96/00288 | 1/1996 | WO | WO 00/53173 | 9/2000 |
| WO | WO 96/09827 | 4/1996 | WO | WO 00/53563 | 9/2000 |
| WO | WO 96/16037 | 5/1996 | WO | WO 00/56403 | 9/2000 |
| WO | WO96/1 9450 | 6/1996 | WO | WO 00/57859 | 10/2000 |
| WO | WO 96/1 9987 | 7/1996 | WO | WO 00/57918 | 10/2000 |
| WO | WO 96/40255 | 12/1996 | WO | WO00/60107 | 10/2000 |
| WO | WO 97/1 6455 | 5/1997 | WO | WO 00/63153 | 10/2000 |
| WO | WO 97/18304 | 5/1997 | WO | WO 00/63161 | 10/2000 |
| WO | WO 97/21676 | 6/1997 | WO | WO 00/63190 | 10/2000 |
| WO | WO 97/25042 | 7/1997 | WO | WO 00/63196 | 10/2000 |
| WO | WO 97/28149 | 8/1997 | WO | WO 00/63209 | 10/2000 |
| WO | WO 97/31907 | 9/1997 | WO | WO 00/63703 | 10/2000 |
| WO | WO 97/35576 | 10/1997 | WO | WO 00/69412 | 11/2000 |
| WO | WO 97/41098 | 11/1997 | WO | WO 00/69445 | 11/2000 |
| WO | WO97/46238 | 12/1997 | WO | WO 00/72825 | 12/2000 |
| WO | WO 98/01100 | 1/1998 | WO | WO 00/72829 | 12/2000 |
| WO | WO 98/05331 | 2/1998 | WO | WO 00/75103 | 12/2000 |
| WO | WO 98/14179 | 4/1998 | WO | WO 00/76482 | 12/2000 |
| WO | WO98/31360 | 7/1998 | WO | WO 00/76488 | 12/2000 |
| WO | WO 98/31361 | 7/1998 | WO | WO 00/78312 | 12/2000 |
| WO | WO98/31366 | 7/1998 | WO | WO 00/78313 | 12/2000 |
| WO | WO 98/43081 | 10/1998 | WO | WO 01/00579 | 1/2001 |

| | | |
|---|---|---|
| WO | WO 01/00603 | 1/2001 |
| WO | WO 01/08686 | 2/2001 |
| WO | WO 01/12176 | 2/2001 |
| WO | WO 01/12187 | 2/2001 |
| WO | WO 01/12612 | 2/2001 |
| WO | WO 01/14349 | 3/2001 |
| WO | WO 01/14350 | 3/2001 |
| WO | WO 01/14351 | 3/2001 |
| WO | WO 01/15744 | 3/2001 |
| WO | WO 01/16120 | 3/2001 |
| WO | WO 01/17994 | 3/2001 |
| WO | WO 01/18210 | 3/2001 |
| WO | WO 01/21181 | 3/2001 |
| WO | WO 01/21259 | 3/2001 |
| WO | WO 01/21578 | 3/2001 |
| WO | WO 01/21647 | 3/2001 |
| WO | WO 01/22962 | 4/2001 |
| WO | WO 01/25225 | 4/2001 |
| WO | WO 01/25226 | 4/2001 |
| WO | WO 01/30343 | 5/2001 |
| WO | WO 01/32161 | 5/2001 |
| WO | WO 01/34148 | 5/2001 |
| WO | WO 01/35970 | 5/2001 |
| WO | WO 01/40192 | 6/2001 |
| WO | WO 01/45676 | 6/2001 |
| WO | WO 01/49267 | 7/2001 |
| WO | WO 01/60807 | 8/2001 |
| WO | WO 01/64221 | 9/2001 |
| WO | WO 01/76632 | 10/2001 |
| WO | WO 01/96347 A1 | 12/2001 |
| WO | WO 02/08188 | 1/2002 |
| WO | WO 02/26729 | 4/2002 |
| WO | WO 02/50027 | 6/2002 |
| WO | WO 02/50060 | 6/2002 |
| WO | WO 02/50068 | 6/2002 |
| WO | WO 02/50090 | 6/2002 |
| WO | WO 02/058685 | 8/2002 |
| WO | WO 02/058696 | 8/2002 |
| WO | WO 02/058731 | 8/2002 |
| WO | WO 02/058732 | 8/2002 |
| WO | WO 02/058733 | 8/2002 |
| WO | WO 02/058734 | 8/2002 |
| WO | WO 02/064094 | 8/2002 |
| WO | WO 02/064130 | 8/2002 |
| WO | WO 02/064549 | 8/2002 |
| WO | WO 02/064664 | 8/2002 |
| WO | WO 02/072104 | 9/2002 |
| WO | WO 02/081454 | 10/2002 |
| WO | WO 03/018024 | 3/2003 |
| WO | WO 03/018059 | 3/2003 |
| WO | WO 03/039542 | 5/2003 |
| WO | WO 03/074101 | 9/2003 |
| WO | WO 03/088962 | 10/2003 |
| WO | WO 2006110882 | 10/2006 |

OTHER PUBLICATIONS

*Exhibit B*: SCH 58235 (ezetimibe), Drug Formulation Development Summary.
*Exhibit C*: SCH 58235 (ezetimibe), Drug Formulation Development Summary.
*Exhibit D*: SCH 58235 (ezetimibe), Drug Formulation Development Summary.
*Exhibit E*: SCH 58235 (ezetimibe), Drug Formulation Development Summary.
Exhibit F: SCH 58235 (ezetimibe), Drug Formulation Development Summary.
Exhibit G: SCH 58235 (ezetimibe), Drug Formulation Development Summary.
Exhibit H: SCH 58235 (ezetimibe), Drug Formulation Development Summary.

Exhibit 1: Master Sheet for the SCH 58235 and Lovastatin Research Study, *Schering-Plough Research Institiute* (Protocol No. C906-411), page 1576-1585.
Exhibit 2: Medical Research Study #1055-97, SCH 58235: Bioavailability of Single Oral Doses of Two Prototype Tablet Formulations and the Reference Capsule Formulation of SCH 58235 in Normal Male Volunteers: A Four Way Crossover Study #C97-221-01, Informed Consent, *Peninsular Testing Corporation*, p. 106-112.
Exhibit 3: Consent Form to Participate in a Research Study, "A Phase II Double Blind Dose Response Investigation of Efficacy and Safety of Four Doses of SCH 58235 Compared to Placebo in Subjects with Primary Hypercholesterolemia," *Schering-Plough Research Institute* (Protocol No. C98-010), p. 1558-1566.
Exhibit 4: Medical Research Study #1096/99, SCH 58235: Pharmacokinetic Pharmacodynamic Drug Interaction Study with Digoxin in Healthy Volunteers #C98-114, Informed Consent, *Peninsular Testing Corporation*, p. 124-130.
Exhibit 5: Informed Consent, "SCH 58235: Assessment of Multiple-Dose Drug Interaction Between 58235 and Gemfibrozil in Healthy Volunteers," *Schering-Plough Research Institute*, p. 1-8.
Vaccaro, W.D. et al , "Sugar-substituted 2- azetidinone cholesterol absorption inhibitors: enhanced potency by modification of the sugar" *Bioorganic & Medicinal Chemistry Ltrs.*, Oxford, G.B., 8:313-318 (1998).
Vaccaro, W.D. et al., "Carboxy-substituted 2-azetidinones as cholesterol absorption inhibitors", *Bioganic & Medicinal Chem. Ltrs. Oxford, G.B.* 8:319-322 (1998).
H. Davis et al., "Ezetimibe, a Potent Cholesterol Absorption Inhibitor, Inhibits the Development Aterosclerosis in Apo E Knockout Mice", *Arterioscler, Thromb. Vasc. Biol* 21:2032-2038, (Dec. 2001).
Simova, E., "Aldol-type addition of hydrocinnamic acid esters to benzylideneaniline", *Chemical Abstracts* No. 15, 86 (Apr. 11, 1997).
Otto et al., Stereochemistry of dehydration and halogenation fo αR and αS isomeric 3-(α-hydroxybenzyl)-1,4 diphenyl=2 azetidinones, *Chemical Abstracts* No. 19, 99 (Nov. 7, 1983).
T. Durst et al, "Metallation of N-Substituted β-Lactams. A Method of the Introduction of 3-substituents intoβ-Lactams" *Canadian Journal of Chemistry*, 50:3196-3201 (1971).
Nobuki, O. et al., "Stereoselective synthesis of b-lactam derivatives by ultrasound promoted Reformatskii reaction" *Chemical Abstracts* No. 106, 17(Apr. 27, 1987).
M. Hoekman, et al., "Synthesis Homologues of 4,5-Dihydroxy-and 4-Hydroxy-5-oxohexanoic Acid γ-Lactones", *J. Agric. Food Chem.*, 30:920-024 (1982).
H. Otto et al. "Darstellung and Stereochemie von 3-(α-Hydroxybenzyl)-1,4-diphenyl-2-azetidononen", *Liebigs Ann. Chem.* 1152-1161 (1983).
G. George et al., "3-(1'-Hydroxyethyl)-2-Azetidinones From 3-Hydroxybutyrates and N-Arylaldimines" *Tetrahedron Letters*, 26:3903-3906 (1985).
Hart et al. "An Enantioselective Approach to Carbapenem Antibodies: Formal Synthesis of (+)-Thienamycin", 26 *Tetrahedron Letters*, 45:5493-5496 (1985).
Panfil, I. et al. "Synthesis of β-Lactams from α, β-Unsaturated Sugar δ-Lactones" 24 *Heterocycles* 6:1609-1617 (1986).
D. Roger Illingworth, "An Overview of Lipid-Lower Drugs" *Drugs* 36:63:71 (1988).
Joseph L. Witztum, M.D., " Current Approaches to Drug Therapy for the Hyercholesterolemic Patient" *Circulation* 80:1101-1114 (1989).
B. Ram et al. "Potential Hypolipidemic agents:Part V", 29B Indian J. Chem. 1134-37 (1990).
Schnitzer-Polokoff, R. et al., "Effects of Acyl-CoA: Cholesterol O-Acyltransferase Inhibition on Cholesterol Absorption and Plasma Lipoprotein Composition in Hamsters" Comp. Biochem. Physiol. 99A:665-670 (1991).
Horie, M. et al, "Hypolipidemic effects of NB-598 in dogs" *Atherosclerosis* 88: 183-192 (1991).
Baxter, A., "Squalestatin 1, a Potent Inhibitor of Squalene Synthase, Which Lowers Serum Cholesterol in Vivo", *The Journal of Biological Chemistry* 267:11705-11708 (1992).

Summary Factfile, "Anti-Antherosclerotic Agents" *Current Drugs Ltd.* (1992).

Harwood H. James, "Pharmacologic consequences of cholesterol absorption inhibition: alteration in cholesterol metabolism and reduction in plasma cholesterol concentration induced by the synthetic saponin β-tigogenin cellobioside (CP-88818; tiqueside) 1" *Journal of Lipid Research* 34:377-395 (1993).

Salisbury, B. et al., "Hypocholesterolemic activity of a novel inhibitor of cholesterol absorption, SCH 48461" *Atherosclerosis* 115:45-63 (1995).

Clader, J. W. et al., "Substituted (1,2-Diarylethyl)amide Acyl-CoA;Cholesterol Acyltransferase Inhibitors: Effect of Polar Groups in Vitro and in Vivo Activity" *Journal of Medicinal Chemistry* 38:1600-1607 (1995).

Sybertz, E., "Sch 48461, a novel inhibitor of cholesterol absorption" Atherosclerosis pp. 311-315 (1995).

Vaccaro, W, et al, "2-Azetidinone Cholesterol Absorption Inhibitors; Increased Potency by Substitution of the C-4 Phenyl Ring", *Bioorg. & Med. Chem.* 6:1429-1437 (1998).

G. Wu et al, A Novel One-Step Diastereo-and enantioselective formation of trans-azetidinones and its application to the total synthesis of cholesterol absorption inhibitors A.C.S. (Apr. 21, 1999).

B. Staels, "New Roles for PPARS in Cholesterol Homeostasis", *Trends in Pharmacological Sciences*, 22:9 p. 444 (Sep. 2001).

Abbott et al, "Tricor® Capsules, Micronized", *Physicians Desk Reference*, Jan. 8, 2001.

M. Feher et al., 1991, Lipids and Lipid Disorders, p.1-87 (1991).

M. Ricote et al., "New Roles for PPARs in Cholesterol Homeostakis", *Trends in Pharmacological Science*, vol. 22, No. 9 44-443 (2001).

C. Dujovne et al, "Reduction of LDL Cholesterol in Patients with Primary Hypercholesterolemia by SCH 48461: Results of a mutlicenter Dose-Ranging Study", *J. Clin, Pharm*. 41:1 70-78 (Jan. 2001).

W. Oppolzer et al., "Asymmetric Diels—Alder Reactions, Facile Preparation and Structure of Sulfonamido—Isobornyl Acrylates", *Tetrahedron Letters* No. 51, 25:5885-5888 (1984).

M. Davidson et al., "Colesevelam Hydischloride: a non-absorbed, polymeric cholesterol lowing agent", *Expert Opinion Investigating Drugs*, 11:2663-71, (Nov. 2000).

M. Davidson et al., "Colesevelam hydrochloride (cholestagel): a new, potent bileacid sequestrant associated with a low incidence of gastrointestinal effects", 159 *Arch. Intern. Med.* 16 1893-900 (Sep. 1999).

I. Wester, "Cholesterol—Lowering effect of plant sterols", *Euro. J. Lipid, Sci. Tech.* 37-44 (2000).

A. Andersson et al., "Cholesterol—lowering effects of a stanol ester-containing low fat margarine used in conjunction with strict lipid-lowering diet", *1 European Heart. J. Supplements* S80-S90 (1999).

H. Gylling et al, Reduction of Serum Cholesterol in Postmenopausal Women with Previous Myocardial Infarction and Cholesterol Malabsorption induced by Dietery Sitostarol Ester Margarine, *96 Circulation12* 4226-4231 (Dec. 16, 1997).

T. Miettinen et al, "Reduction of Serum Cholesterol with Sitostanol-Ester Margarine in a Mildly Hypercholesterolemic Population", *New England Journal of Med.* 333 1308-1312 (Nov. 16, 1995).

T. Bocan et al., "The ACAT Inhibitor Avasimibe Reduces Macrophages and Matrix Metalloproteinase Expression in Atherosclerotic Lesions of Hypercholesterolemic Rabbits", *Arterioscler Thromb Vasc. Biol.* 70-79 (Jan. 2000).

M. Van Heek et al., "In Vivo Metabolism—Based Discovery of a Potent Cholesterol Absorption Inhibitor, SCH 58235, in the Rat Rhesus Monkey through the identification of the active metabolites of SCH48461," *J. Pharma and Experimental Therapeutics 1* 157-163 (1997).

H. Davis et al., "The Cholesterol Absorption Inhibitor Ezetimible Inhibits the Development of Atherosclerosis in apo E Knockout (-/-) mice fed low fat and western diets," *151 Atherosclerosis 1*:133 (Jul. 2000).

L. Nguyen et al., "Unexpected Failure of Bile Acid Malabsorption to Stimulate Cholesterol Synthesis in Sitosterolemia with Xanthomatosis", *10 Atherosclerosis 2*, 289-197 (1990).

L. Nguyen et al., "Regulation of Cholesterol Biosynthesisin Sitosterolemia: effects of lovastatin, Cholestyramine, and dietary sterol restriction," *32 J.Lipid Res.* 1941-1948 (1991).

M. Cobb et al., "Sitosterolemia: Opposing Effects of cholestyramine and Lovastatin on Plasma Sterol Levels in a Homozygous GIrl and Her Heterozygous Father," *45 Metabolism 6* 673-679 (Jun. 1996).

M. Huettinger et al., "Hypolipidemic Activity of HOE-402 is mediated by Stimulation of the LDL Receptor Pathway", *13 Arteriosclerosis and Thrombosis 7* 1005-1012 (Jul. 1993).

J. Best et al., "Diabetic Dyslipidaemia", *59 Drugs* 1101-1111 (May 2000).

P. Chong, et al, "Current, New and Future Treatment in Dislipidaemia and Atherosclerosis", *60 Drugs 1* 55-93 (Jul. 2000).

M. Brown et al, "A Receptor—Mediated Pathway for Cholesterol Homeostasis", *232 Science* 34-47 (Apr. 4, 1986).

L. Lipka et al., "Reduction of LDL-Cholesterol and Elevation of HDL-Cholesterol in Subjects with Primary Hypercholesterolemia by SCH 58235: Pooled Analysis of Two Phase II Studies", *JACC 257A* (Feb. 2000).

Medical Economics, Co., Inc., *Physician's Desk Reference*, 207-208, 2054 (55th Ed. 2001).

K. Fassbender et al., "Simvastatin Strongly Reduces Levels of Alzheimer's Disease β-Amyloid Peptides Aβ 42 and Aβ40 in vitro and in vivo", *PNAs Early Edition*, www.phas.org/cgi/doi/10,1073/phas.081620098 (2001).

Andrx Announces Results of Alzheimer's Disease Clinical Study, *Andrx Corporate Release* (Apr. 11, 2001).

Andrx (ADRX): Pos Phase II Results Using Avicor in Alzheimer's: Str Buy; $130, *US Bancorp Piper*, Apr. 12, 2001.

Statins May Protect Against Alzheimer's Disease; much research needed, *Geriatrics* Feb. 2001.

Dementia and Statins, *The Lancet* Mar. 17, 2001.

Research & Development: Andrx Says Cholesterol Drug May Treat Alzheimers, *Reuters* Apr. 11, 2001.

Cholesterol Drugs Ease Alzheimer's Damage; www.usatoday.com Apr. 10, 2001.

Lovastation XL of Use in Alzheimer's? News Edge (May 2, 2001).

L. Refolo et al, Hypercholesterolemia Accelerates the Alzheimer's Amyloid Pathology in a Transgenic Morse Model, *Neurobiology of Disease* 321-331 (2000).

D. Kang et al., "Modulation of Amyloid β-protein Clearance and Alheimer's Disease Susceptibility by the LDL Receptor—Related Protein Pathaway", *Journal of Clinical Investigation* 106:9, 1159-1166 (Nov. 2000).

Y.A. Kesaniewmi, "Intestinal Cholesterol Absorption Effiviency in Man is Related to Apoprotein E Phenotype", *J. Clin Invest.* 80(2) 578-81 (Aug. 1987).

J. Busciglio et al., "Generation of β-amyloid in the secretary pathway in neuronal and nonneuronal cells", *90 Proc. Nat'l. Acad. Sci, USA*, 2092-2096 Neurobiology (Mar. 1993).

L. Farrer et al., "Assessment of Genetic Risk for Alzheimer's Disease Among first Degree Relatives", *Annals of Neurology* 25:5, 485-493 (May 1989).

A. Goate et al., "Segregation of a Missense Mutation in the Amyloid Precursor Protein Gene with Familial Alzheimer's Disease", *349 Nature No. 6311*, 704-706 (Feb. 21, 1991).

D. Mann et al., "The Pattern of Acquisition of Plaques and Tangle in the Brains of Patients Under 50 years of Age with Down's Syndrome", *89 J. Neuro. Sci.*, 169-179 (Feb. 1989).

G. McKhann et al., "Clinical Diagnosis of Alzheimer's Disease", *34 Neurology No. 7*, 939-944 (Jul. 1984).

D. Selokoe, "Alzheimer's Disease: Genotypes, Pheontype and Treatments", *275 Science*, 630-631 (Jan. 31, 1997).

C. Van Duijn, et al., "Familial Aggregation of Alzheimer's Disease and Related Disorders: A collaborative Re-Analysis of Case-Control Studies", *20 Int'l J. Epidemiology No. 2 (Suppl. 2)*, 513-520 (1991).

T Nagahara et al., "Dibasic (Amidcinoaryl) Propanoic Acid Derivatives as Novel Blood Coagulation Factor Xa Inhibitors", *J. Med. Chem* 37:1200-1207 (1994).

Mellott et al., "Acceleration of Recombinant Tissue-Type Plasminogen Activator Induced Reperfusion and Prevention of Reocculsion by Recombinant Antistasin, a selective factor XA Inhibitor, in a Canine Model of Femoral Arterial Thrombosis", *Circulation Research*, 70:1152-1160 (1992).

Sitko et al., "Conjunctive Enhancement of Enzymatic Thrombolysis and Prevention of Thrombotic Reocclusion With the Selective Factor Xa Inhibitor, Tick Anticoagulant Peptide", *Circulation*, 85:808-815 (1992).

Seymour et al., 1994, *Biochemistry*, 33:3949-3959.

Markwardt, 1994, *Thrombosis and Hemostasis*, 72:477-479.

Mendall et al., "C-Reactive Protein and its relation to cardiovascular risk factor: A population based cross sectional study", *BMJ*; 312:1061-1065 (Apr. 27, 1996).

Ridker P. et al., "Prospective Studies of C-Reactive Protein as a risk factor for cardiovascular disease", 46 *J. Investig. Med.*; 8:391-395 (1998).

Waters, D. et al., "A Controlled Clinical Trial to Assess the Effect of a Calcium Channel Blocker on the Progression of Coronary Atherosclerosis", *Circulation*; 82:1940-1953 (1990).

Fleckenstein, 1985, *Cir. Res*. vol. 52 (Suppl. 1) 13-16.

Fleckenstein, 1983, "Experimental Facts and Therapeutic Prospects", *John Wiley, New York*, pp. 286-313.

McCall, D., 1985, *Curr. Pract. Cardiol*. vol. 10, 1-11.

Remington 1995, The Science and Practice of Pharmacy, (19th Ed. 1995) p. 963.

M. Chistie et al., "Early—Onset Amyloid Deposition and Cognitive Deficits in Transgenic Mice Expressing a Double Mutant Form of Amyloid Precursor Protein 695", 276 *J. Biol. Chem*. No. 24; 21562-70 (Jun. 15, 2001).

C. Janus et al., "Aβ Peptide Immunization Reduces Behavioral impairment and Plaques in a Model of Alzheimer's Disease", *408 Nature* 21/28; 979-982 (Dec. 2000).

Manual of Laboratory Operations, Lipid Research Clinics Program Report, Washington, D.C., *U.S. Dept. of Health, Education and Welfare Publication*; 1:75-628 (1974).

Steiner, PM et al., Standardization of Micromethods for Plasma Cholesterol, Triglyceride and HDL-Cholesterol with the Lipid Clinic's Methodology [abstract], *J. Clin. Chem. Clin. Bichem*; 19:850 (1981).

Steele WG, et al., Enzymatic Determinations of Cholesterol in High Density Lipoprotein Fractions Prepared by Precipitation Technique, 22 *Clin. Chem.*; 1:98-101 (1976).

Salen et al., "Increased Sitosterol Absorption, Decreased Removal and Expanded Body Pools Compensate for Reduced Choelsterol Syntheses in Sitosterolemia with Xanthomatosis", *J. Lipd Res.*,; 30:1319-1330 (1989).

Lutjohann et al., "Sterol Absorption and Sterol Balance in Phytosterolemia Evaluated by Deuterium-Labeled Sterols: Effect of Sitostanol Treatment", *J. Lipid Res.*; 36:8; 1763-1773 (1995).

Zhang et al., "Calpain Inhibitor I Increases B- Amyloid Peptide by Inhibiting the Degradation of the Substrate of γ- Secretase" 274 *J. Biol, Chem.*, 13:8966-8972 (1999).

Zhang et al., "Biochemical Characterization of the γ-Secretase Activity that Produces B- Amyloid Peptides", Biochemistry 40:5049-5055 (2001).

Ida et al., "Analysis of Heterogeneous BA4 Peptides in Human Cerebrospinal Fluid and Blood by a Newly Developed Sensitive Western Blot Assay", 271 *J. Biol, Chem.*; 37:22908-22914 (1996).

Lichtlen, P.R. et al., 1990, *Lancet*; 335:1109-1113.

Bays et al., "Effectiveness and Tolerability of Ezetimibe in Patients with Primary Hypercholesterolemia: Pooled Analysis of Two Phase II Studies", *Clinical Therapeutics*, 23:1209-1230 (2001).

E. Leitersdorf et al., "Cholesterol absorption inhibition: filling an unmet need in lipid-lowering management", *European Heart Journal Supplement*, 3:E17-E23 (Jun. 2001).

Bauer et al., "Ezetimibe Does not Affect the Pharmacokinetics or Pharmacodynamics of Warfarin", *Clinical Pharmacology and Therapeutics*, 69:2 p. 5 (Mar. 6-10, 2001).

Keung et al., Ezetimibe Does Not Affect the Pharmacokinetics of oral Contraceptives, *Clinical Pharmacology and Therapeutics*, 69:2 p. 55 (Mar. 6-10, 2001).

Kosoglou et al., "Pharmacodynamic interaction between fenofibrate and the Cholesterol Absorption Inhibitor Ezetimibe", *Workshops Lipid Lowering Drugs 72nd EAS Congress*, p. 38 (May 21-23, 2001).

T. Kosoglou et al., "Coadministration of Ezetimibe and Fenofibrate Leads to Favorable Effects On Apo CII and LDL Subfractions", *Posters 11 Lipid Lowering Drugs/Novel, 72nd EAS Congress*, p. 89 (May 21-23, 2001).

L. Reyderman et al., "Assessment of a Multiple-Dose Interaction Between Ezetimibe and Gemfibrozil", Presented at XIV Int'l Symp. on Drugs Affecting Lipid Metabolism (DALM) N.Y. (Sep 9-12, 2001).

P. Statkevich et al., "Ezetimibe Does Not Affect the Pharmacokinetics and Pharmacodynamics of Glipizide", *Clinical Pharmacology & Therapeutics*, 69:67 (Mar. 6-10, 2001).

Knopp et al, "Effect of Ezetimibe on Serum Concentrations of Lipid-Soluble Vitamins", *Posters 11. Lipid Lowering Drug/Novel 72[hd] EAS Congress*, p. 90 (May 21-23, 2001).

Kosoglou et al., "Pharmacodynamic Interaction Between Fenofibrate and the Cholesterol Absorption Inhibitor Ezetimibe", *Workshops Lipid Lowering Drugs, 72nd EAS Congress*, p. 38 (Mar. 6-10, 2001).

Bays et al., "Low-Density Lipoprotein Cholesterol Reduction By SCH 58235 (Ezetimibe), A Novel Inhibitor of Intestinal Cholesterol Absortion, in 243 Hypercholesterolemic Subjects: Results of a Dose-Response Study", *XII International Symposium on Atherosclerosis*, Stockholm, Sweden (Jun. 25-29, 2000).

Castaner et al, "Ezetimibe—Hypolipidemic Cholesterol Absorption Inhibitor", *Drugs of the Future*, 25(7):679-685 (2000).

Lipka et al., "Reduction of LDL-Cholesterol and Elevation of HDL-Cholesterol in Subjects with Primary Hypercholesterolemia by Ezetimibe (SCH 58235): Pooled Analysis of Two Phase II Studies", *American College of Cardiology Annual Meeting*, Anaheim, CA (Mar. 12-15, 2000).

Van Heek et al., "Comparison of the activity and disposition of the novel cholesterol absorption inhibitor, SCH58235, and its glucuronide, SCH60663", *British Journal of Pharmacology*, 129:1748-1754 (2000).

Van Heek et al, 2000, "The potent cholesterol absorption inhibitor, ezetimibe is glucuronidated in the intestine, localizes to the intestine, and circulates enteroheptically", *XII International Symposium of Atherosclerosis*, Stockholm Sweden (Jun. 25-29, 2000).

Iannucci et al., "Metabolism of SCH 58235 in the Human, Rat and Dog", *47th ASMS Conference on Mass Spectrometry and Allied Topics*, Dallas, TX (Jun. 13-17, 1999).

Reiss et al., "An Enzymatic Synthesis of Glucoronides of Azetidinone-based Cholesterol Absorption Inhibitors", *Bioorganic & Medicinal Chemistry*, 7:2199-2202 (1999).

Rosenblum et al., "Discovery of 1-(4-Flurophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem*. 41:973-980 (1998).

Vaccaro et al., "Sugar-Substitiuted 2-Azetidinone Cholesterol Absorption Inhibitors: Enhanced Potency by Modification of the Sugar", *Bioorganic & Medicinal Chemistry Letters*, 8:313-318 (1998).

Zaks et al., "Enzymatic Glucuronidation of a Novel Cholesterol Absorption Inhibitor, SCH 58235", *Applied Biochemistry and Biotechnology*, 73:205-214 (1998).

W. Insuli et al., Postmenopausal Hypercholesterolemic Women Derive Additive Benefit from Raloxifene and Simvastatin on Lipid Parameters, *World Heart Federation 6th International Symposium on Global Risk of Coronary Heart Disease and Stroke—Abstract Book*, p. 35 (Jun. 12-15, 2002).

L. Simons et al., 2002, "Ezetimibe added to on-going statin therapy for treatment of primary hypercholesterolemia: Efficacy and safety in patients with Type 2 diabetes mellitus", presented at rhe 38th Annual Meeting of the EASD, Sep. 1-5, 2002.

C. Allain et al, 1974, "Enzymatic Determination of Total Serum Cholesterol", *Clinical Chemical*, 20:470-475.

R. Mayhofer et al., 1980, "Simple-Preparation of 3-Benzylidene-2-azetilidinones", *Synthesis*, 247-248.

Burrier, R.E. et al, 1994, "Demonstration of a Direct Effect on Hepatic Acyl CoA:Cholesterol Acyl Transferase (ACAT) Activity by An Orally Administered Enzyme Inhibitor in the Hamster", *Biochemical Pharmacology* 47:15451551.

Burrier, R.E. et al., 1994, "The Effect of Acyl CoACholesterol Acyltransferase Inhibitor on the Uptake, Esterification and Secretion of Cholesterol by the Hamster Small Intestine", *The Journal of Pharmacology and Experimental Therapeutics* 272:156-163.

E.F. Binder et al., "Effects of Hormone Replacement Therapy on Serum Lipids in Elderly Women. A Randomized, Placebo-Controlled Trial", *134 Ann. Intern. Med.* 9:754-760 (May 1, 2001).

MR Haymart et al., "Optimal Management of Dyslipidemia in Women and Men", *2 J. Gend. Specif. Med.* 6:37-42 (Nov.-Dec. 1997).

"Framingham Heart Study Analysis Reveals Some Primary Prevention Subgroups Are Being Overlooked", *Heartwire* (Apr. 12, 2001).

Detection Evaluation, and Treatment of High Blood Cholesterol in Adults (Adult Treatment Panel III), "Third Report of the National Cholesterol Education Program (NCEP)", *NIH* Publication No. 01-3670 (May 2001).

Van Heek et al., "Ezetimibe, A Potent Cholesterol Absorption Inhibitor, Normalizes Combined Dyslipidemia in Obese Hyperinsulinemic Hamsters", *50 Diabetes* 1330-1335 (Jun. 2001).

"Additional Statins Show Anti-Inflammatory Effect", 103 *Circulation* 1933-35 (Apr. 17, 2001).

H. Hauser, et al, "Identification of a Receptor Mediating Absorption of Dietary Cholesterol in the Intestine", *Biochemistry* 37:17843-17850, 1998.

G. Salen, et al., "Sitosterolemia", *Journal of Lipid Research* 33:945-955, 1992.

Stedman's Medical Dictionary, 27th Edition, p. 1381.

Stuart B. Rosenblum et al., Discovery of 1-(4-Fluorophenyl)-(3R)-[3-(fluorophenyl)-(3S)-hydroxypropyl]-(4S)-(4-hydroxyphenyl)-2-azetidinone (SCH 58235): A Designed, Potent, Orally Active Inhibitor of Cholesterol Absorption, *J. Med. Chem.* 41:973-980 (1998).

Remington's Pharmaceutical Sciences, 18th ed. 1990 p. 1319, 1633-1647.

Baker S G et al., Treatment of homozygous familial hypercholesterolaema with probucol, *South African Medical Journal* (1982).

R. Milanese et al., Xantomi E Ipercolesterolemia: Prevalenza, Diagnosi e Terapia, *Chron. Derm.* 455-61 (1990).

"Study showed ezetimibe significantly reduced levels of LDL cholesterol of "bad" cholesterol in patients" *Schering Press Release* 1-3 (2001).

Kosoglou et al., "Pharmacodynamic interaction between fenofibrate and the cholesterol absorption inhibitor ezetimibe" *Atheroscelerosis* (2):3(2001).

Davis et al., "The Synergistic Hypocholesterolemic Activity of the Potent Cholesterol Absorption Inhibitor, Ezetimibe, in Combination with 3-Hydroxy-3-Methylglutaryl Coenzyme A Reductase Inhibitors in Dogs" *Metabolism* 50(10):1234-1241(2001).

Thompson, G.R. et al., "Novel lipid-regulating drugs" *Expert Opinion on Investigational Drugs* 9(11):2619-2628 (2000), XP008011782.

Kosoglou, T. et al., "Coadministration of ezetimibe and lenofibrate leads to favorable effects on Apo CII and LDL subfractions" *Atherosclerosis* 2:89 (2001), XP001132089 abstract.

Gilber R. Thompson et al., Novel lipid-regulating drugs, Ashley Publications Ltd. ISSN 1354-3784, 2000, pp. 2619-2628.

Belamarich P.F. et al., Response to diet and cholestyramine in a patient with sitosterolemia, Pediatrics, ISSN 0031-4005, Dec. 1990.

Salen G. et al., Lethal atherosclerosis associated with abnormal plasma and tissue sterol composition in sitosterolemia with xanthomatosis, Journal of lipid research, ISSN 0022-2275, Sep. 1985.

Sorbera et al., Netoglitazone, *Drugs of the Future*, 2002, 27(2):132-139.

Michel Farnier, Nouvelles approaches médicamenteuses dans le traitement des dyslipidémies, *MT Endocrinologie*, 2002, 4:252-259.

Berger et al., Physiological and Therapeutic Roles of Peroxisome Proliferator-Activated Receptors, *Diabetes Technology & Therapeutics*, 2002, 4:163-174.

U.S. Appl. No. 10/791,910.
U.S. Appl. No. 10/792,346.
U.S. Appl. No. 10/791,979.
U.S. Appl. No. 10/701,244.
U.S. Appl. No. 10/639,900.

Cholesterol Drugs May Reverse MS Symptoms, Studies in Mice show statins may treat Multiple Sclerosis— CNN.com/Health, Wednesday, Nov. 6, 2002 posted: 4:30 PM EST (2130 GMT).

D. Grady, Health, Antiocholesterol Drug Found to Help Paralytic Mice, www.nytimes.com/2002/11/07/health/07DRUG.html.

S. Youssef et al., Atorvastatin, a HMG-CoA Reductase Inhibitor, Promotes a Th2 Bias and Reversal of Paralysis in Chronic Relapsing Autoimmune Encephalomyelitis, *Neurology* 58 Apr. 2002 (Suppl 3), A384-A385.

M. Soilu-Hanninen et al., Semliki Forest Virus Infects Mouse Brain Endothelial Cells and Causes Blood-Brain Barrier Damage, *Journal of Virology*, Oct. 1994, 6291-6298.

Chapter 15 Animal Models for Autoimmune and Inflammatory Disease, Unit 15.1 Experimantal Autoimmune Encephalomyelitis in the Mouse, *Current Protocols in Immunology*, Nov. 6, 2002.

J. Pope et al., Flow Cytometric and Functional Analyses of Central Nervous System-Infiltrating Cells in SJL/J Mice with Theiler's Virus-Induced Demyelinating Disease—Evidence for a CD4+ T Cell-Mediated Pathology, *The Journal of Immunology* 4050-4058.

H. Butzkueven et al., LIF receptor signaling limits immune-mediated demyelination by enhancing oligodendrocyte survival, *2002 Nature Publishing Group- Nature Medicine*, 8:6 613-619 (Jun. 2002).

I. Grewal et al., CD62L Is Required on Effector Cells for Local Interactions in the CNS to cause Myyelin Damage in Experimental Allergic Encephalomyelitis, *Immunity*, 14:291-302 (Mar. 2001).

E. Tran et al., Induction of experimental autoimmune encephalomyelitis in C57BL/6 mice deficient in either the chemokine macrophage inflammatory protein—1α or its CCR5 Receptor, *Eur. J. Immunol.*, 30:1410-1415 (2000).

F. Giubilei et al., Blood cholesterol and MRI activity in first clinical episode suggestive of simple sclerosis, *Aeta Neurol Scan*, 106:109-112 (2002).

R.O. Weller, Neurology & Applied Neurobioiogy, *Blackwell Scientific Publications*, 20:2 Apr. 1994.

R. Berkow et al., The Merck Manual of Medical Information—Home Edition, *Pocket Books*, Title of Chapter 68 347-350 (1997).

Pelfrey, C., Actrims—Ectrims 2002 (Part II), Baltimore, MD USA, Sep. 18-21, 2002, *The Investigational Drugs Database ALERTS*.

P. Reany, Cholesterol Drugs may help MS Patients, *Yahoo Financial News*, Wednesday, Nov. 6, 2002 pm ET.

H. Wekerle, Tackling Multiple Sclerosis, *Nature* 420:39-84 (2002).

S. Youssef et al., The HMG-CoA reductase inhibitor, atorvastatin, promotes a TH2 bias and reverse paralysis in central nervous system autoimmune disease, *Nature*, 420:78-84 Nov. 7, 2002.

Shestopalov, A.M. et al., Cyclization of Nitriles .Xl. Synthesis and reactions of 3-Amino-2-Carboxythieno[2,3-b]-Pyridines, *Zhurnal Organicheskoi Khimii*, 20:9 1818-1827.

Shestopalov, A. M. et al., Cyclization of Nitriles .XIX. Synthesis and reactions of the derivatives of 2-oxo-and 2-thioxo-2,5,6,7-Tetrahydro-1H-Pyrindines, *Zhurnal Organicheskoi Khimii* 22:6 1163-1168.

Luis Grubefg, MD, "Inflammatory Markers in Acute Coronary Syndromes: C-reactive Protein (CRP) and Chlamydia," American Heart Association Scientific Sessions 2000.

The International Search Report for International Application No. PCT/US2004/006555 (Apr. 8, 2004)—5 pages.

Kosoglou, entitled "Co-Administration of Simvastatin and Ezetimibe Leads to Significant Reduction in LDL-Cholesterol," Proceedings of International Congress on Coronary, Artery Disease from Prevention to Intervention; Lyon, France p. 271 (2000) XP008027568.

\* cited by examiner

SUBSTITUTED AZETIDINONE COMPOUNDS, PROCESSES FOR PREPARING THE SAME, FORMULATIONS AND USES THEREOF

CROSS-REFERENCE TO RELATED APPLICATIONS

This application is a divisional of U.S. patent application Ser. No. 10/791,979, filed Mar. 3, 2004 now U.S. Pat. No. 7,192,944, and claims the benefit of priority from U.S. Provisional Patent Application Ser. No. 60/452,722, filed Mar. 7, 2003, each incorporated by reference herein.

BACKGROUND OF THE INVENTION

Field of the Invention

The present invention relates to substituted azetidinone compounds useful for treating vascular and lipidemic conditions, and formulations and processes related thereto.

Atherosclerotic coronary heart disease (CHD) represents the major cause for death and vascular morbidity in the western world. Risk factors for atherosclerotic coronary heart disease include hypertension, diabetes mellitus, family history, male gender, cigarette smoke and high serum cholesterol. A total cholesterol level in excess of 225-250 mg/dl is associated with significant elevation of risk of CHD. The newly revised NCEP ATP III low density lipoprotein (LDL-C) goal for patients with CHD or CHD risk equivalent is <100 mg/dL (2.59 mmol/L), for individuals with two or more risk factors is <130 mg/dL (3.37 mmol/L) and for individuals with fewer than two risk factors is <160 mg/dL (4.14 mmol/L).

The regulation of whole-body cholesterol homeostasis in mammals and animals involves the regulation of dietary cholesterol and modulation of cholesterol biosynthesis, bile acid biosynthesis and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis. When intestinal cholesterol absorption is reduced, by whatever means, less cholesterol is delivered to the liver. The consequence of this action is decreased hepatic lipoprotein (VLDL) production and an increase in the hepatic clearance of plasma cholesterol, mostly as LDL. Thus, the net effect of inhibiting intestinal cholesterol absorption is a decrease in plasma cholesterol levels and progression of atherosclerotic lesion formation.

U.S. Pat. Nos. 5,767,115, 5,624,920, 5,668,990, 5,656,624 and 5,688,787, respectively, disclose hydroxy-substituted azetidinone compounds and substituted β-lactam compounds useful for lowering cholesterol and/or in inhibiting the formation of cholesterol-containing lesions in mammalian arterial walls. U.S. Pat. No. 5,756,470, U.S. Patent Application No. 2002/0137690, U.S. Patent Application No. 2002/0137689 and PCT Patent Application No. WO 2002/066464 disclose sugar-substituted azetidinones and amino acid substituted azetidinones useful for preventing or treating atherosclerosis and reducing plasma cholesterol levels.

U.S. Pat. Nos. 5,846,966 and 5,661,145, respectively, disclose treatments for inhibiting atherosclerosis and reducing plasma cholesterol levels using such hydroxy-substituted azetidinone compounds or substituted β-lactam compounds in combination with HMG CoA reductase inhibitor compounds, which act by blocking hydroxymethylglutaryl coenzyme A (HMG-CoA) reductase (the rate-limiting enzyme in hepatic cholesterol synthesis).

Despite recent improvements in the treatment of vascular disease, there remains a need for improved compounds, compositions and treatments for hyperlipidaemia, atherosclerosis and other vascular conditions that provide more efficient delivery of treatment.

SUMMARY OF THE INVENTION

In one embodiment, the present invention provides a compound represented by the structural formula (I):

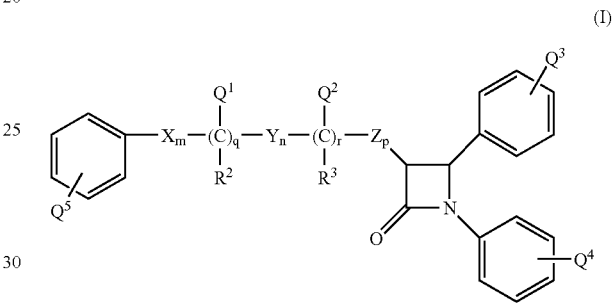

or pharmaceutically acceptable isomers, salts, solvates or esters of the compound of Formula (I), wherein in Formula (I) above:

X, Y and Z can be the same or different and each is independently selected from the group consisting of —$CH_2$—, —CH(alkyl)- and —C(alkyl)$_2$-;

$Q^1$ and $Q^2$ can be the same or different and each is independently selected from the group consisting of H, —($C_0$-$C_{30}$ alkylene)-G, —$OR^6$, —$OC(O)R^6$, —$OC(O)OR^9$, —$OC(O)NR^6R^7$ and -L-M;

$Q^3$ is 1 to 5 substituents independently selected from the group consisting of alkyl, alkenyl, alkynyl, —($C_0$-$C_{30}$ alkylene)-G, —($C_0$-$C_{10}$ alkylene)-$OR^6$, —($C_0$-$C_{10}$ alkylene)-C(O)$R^6$, —($C_0$-$C_{10}$ alkylene)-C(O)$OR^6$, —($C_0$-$C_{10}$ alkylene)-OC(O)$R^6$, —($C_0$-$C_{10}$ alkylene)-OC(O)$OR^9$, —CH=CH—C(O)$R^6$, —CH=CH—C(O)$OR^6$,

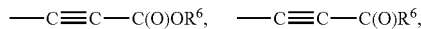

—O—($C_1$-$C_{10}$ alkylene)-$OR^6$, —O—($C_1$-$C_{10}$ alkylene)-C(O)$R^6$, —O—($C_1$-$C_{10}$ alkylene)-C(O)$OR^6$, —CN, —O—($C_0$-$C_{10}$ alkylene)-C(O)$NR^6R^7$, —O—($C_0$-$C_{10}$ alkylene)-C(O)$NR^6NR^7C(O)OR^6$, —O—($C_1$-$C_{10}$ alkylene)-C(O)(aryl)-N—N=N⁻, —OC(O)—($C_1$-$C_{10}$ alkylene)-C(O)$OR^6$, —($C_0$-$C_{10}$ alkylene)-C(O)$NR^6R^7$, —($C_0$-$C_{10}$ alkylene)-OC(O)$NR^6R^7$, —$NO_2$, —($C_0$-$C_{10}$ alkylene)-$NR^6R^7$, —O—($C_2$-$C_{10}$ alkylene)-$NR^6R^7$, —$NR^6C(O)R^7$, —$NR^6C(O)OR^9$, —$NR^6C(O)NR^7R^8$, —$NR^6S(O)_{0-2}R^9$, —$N(S(O)_{0-2}R^9)_2$, —$CHNOR^6$, —C(O)$NR^6R^7$, —C(O)$NR^6NR^6R^7$, —$S(O)_{0-2}NR^6R^7$, —$S(O)_{0-2}R^9$, —O—C(O)—($C_1$-$C_{10}$ alkylene)-C(O)$NR^6R^7$, —OC(O)—($C_1$-$C_{10}$ alkylene)-$NR^6C(O)O$-(alkylaryl), —P(O)(OR$^{10}$)$_2$, —(C$_1$-C$_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

Q$^4$ is 1 to 5 substituents independently selected from the group consisting of alkyl, alkenyl, alkynyl, —(C$_0$-C$_{30}$ alkylene)-G, —(C$_0$-C$_{10}$ alkylene)-OR$^6$, —(C$_0$-C$_{10}$ alkylene)-C(O)R$^6$, —(C$_0$-C$_{10}$ alkylene)-C(O)OR$^6$, —(C$_0$-C$_{10}$ alkylene)-OC(O)R$^6$, —(C$_0$-C$_{10}$ alkylene)-OC(O)OR$^9$, —CH═CH—C(O)R$^6$, —CH═CH—C(O)OR$^6$,

—C≡C—C(O)OR$^6$, —C≡C—C(O)R$^6$,

—O—(C$_1$-C$_{10}$ alkylene)-OR$^6$, —O—(C$_1$-C$_{10}$ alkylene)-C(O)R$^6$, —O—(C$_1$-C$_{10}$ alkylene)-C(O)OR$^6$, —CN, —O—(C$_1$-C$_{10}$ alkylene)-C(O)NR$^6$R$^7$, —O—(C$_0$-C$_{10}$ alkylene)-C(O)NR$^6$NR$^7$C(O)OR$^6$, —O—(C$_1$-C$_{10}$ alkylene)-C(O)(aryl)-N—N═N$^-$, —OC(O)—(C$_1$-C$_{10}$ alkylene)-C(O)OR$^6$, —(C$_0$-C$_{10}$ alkylene)-C(O)NR$^6$R$^7$, —(C$_0$-C$_{10}$ alkylene)-OC(O)NR$^6$R$^7$, —NO$_2$, —(C$_0$-C$_{10}$ alkylene)-NR$^6$R$^7$, —O—(C$_1$-C$_{10}$ alkylene)-NR$^6$R$^7$, —NR$^6$C(O)R$^7$, —NR$^6$C(O)OR$^9$, —NR$^6$C(O)NR$^7$R$^8$, —NR$^6$S(O)$_{0-2}$R$^9$, —N(S(O)$_{0-2}$R$^9$)$_2$, —CHNOR$^6$, —C(O)NR$^6$R$^7$, —C(O)NR$^6$NR$^6$R$^7$, —S(O)$_{0-2}$NR$^6$R$^7$, —S(O)$_{0-2}$R$^9$, —O—C(O)—(C$_1$-C$_{10}$ alkylene)-C(O)NR$^6$R$^7$, —OC(O)—(C$_1$-C$_{10}$ alkylene)-NR$^6$C(O)O-(alkylaryl), —P(O)(OR$^{10}$)$_2$, —(C$_1$-C$_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

Q$^5$ is 1 to 5 substituents independently selected from the group consisting of alkyl, alkenyl, alkynyl, —(C$_0$-C$_{30}$ alkylene)-G, —(C$_0$-C$_{10}$ alkylene)-OR$^6$, —(C$_0$-C$_{10}$ alkylene)-C(O)R$^6$, —(C$_0$-C$_{10}$ alkylene)-C(O)OR$^6$, —(C$_0$-C$_{10}$ alkylene)-OC(O)R$^6$, —(C$_0$-C$_{10}$ alkylene)-OC(O)OR$^9$, —CH═CH—C(O)R$^6$, —CH═CH—C(O)OR$^6$,

—C≡C—C(O)OR$^6$, —C≡C—C(O)R$^6$,

—O—(C$_1$-C$_{10}$ alkylene)-OR$^6$, —O—(C$_1$-C$_{10}$ alkylene)-C(O)R$^6$, —O—(C$_1$-C$_{10}$ alkylene)-C(O)OR$^6$, —CN, —O—(C$_1$-C$_{10}$ alkylene)-C(O)NR$^6$R$^7$, —O—(C$_0$-C$_{10}$ alkylene)-C(O)NR$^6$NR$^7$C(O)OR$^6$, —O—(C$_1$-C$_{10}$ alkylene)-C(O)(aryl)-N—N═N$^-$, —OC(O)—(C$_1$-C$_{10}$ alkylene)-C(O)OR$^6$, —(C$_0$-C$_{10}$ alkylene)-C(O)NR$^6$R$^7$, —(C$_0$-C$_{10}$ alkylene)-OC(O)NR$^6$R$^7$, —NO$_2$, —(C$_0$-C$_{10}$ alkylene)-NR$^6$R$^7$, —O—(C$_1$-C$_{10}$ alkylene)-NR$^6$R$^7$, —NR$^6$C(O)R$^7$, —NR$^6$C(O)OR$^9$, —NR$^6$C(O)NR$^7$R$^8$, —NR$^6$S(O)$_{0-2}$R$^9$, —N(S(O)$_{0-2}$R$^9$)$_2$, —CHNOR$^6$, —C(O)NR$^6$R$^7$, —C(O)NR$^6$NR$^6$R$^7$, —S(O)$_{0-2}$NR$^6$R$^7$, —S(O)$_{0-2}$R$^9$, —O—C(O)—(C$_1$-C$_{10}$ alkylene)-C(O)NR$^6$R$^7$, —OC(O)—(C$_1$-C$_{10}$ alkylene)-NR$^6$C(O)O-(alkylaryl), —P(O)(OR$^{10}$)$_2$, —(C$_1$-C$_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

wherein optionally one or more carbon atoms of the —(C$_0$-C$_{30}$ alkylene)- radical of Q$^1$, Q$^2$, Q$^3$, Q$^4$ and Q$^5$ is independently replaced by —O—, —C(O)—, —CH═CH—,

—C≡C—,

—N(alkyl)-, —N(alkylaryl)- or —NH—;

G is selected from the group consisting of a sugar residue, disugar residue, trisugar residue, tetrasugar residue, sugar acid, amino sugar, amino acid residue, oligopeptide residue comprising 2 to 9 amino acids, trialkylammoniumalkyl radical and —S(O)$_2$—OH, wherein optionally the sugar residue, disugar residue, trisugar residue, tetrasugar residue, sugar acid, amino sugar, amino acid residue or oligopeptide residue of G is substituted with -L-M;

L is selected from the group consisting of

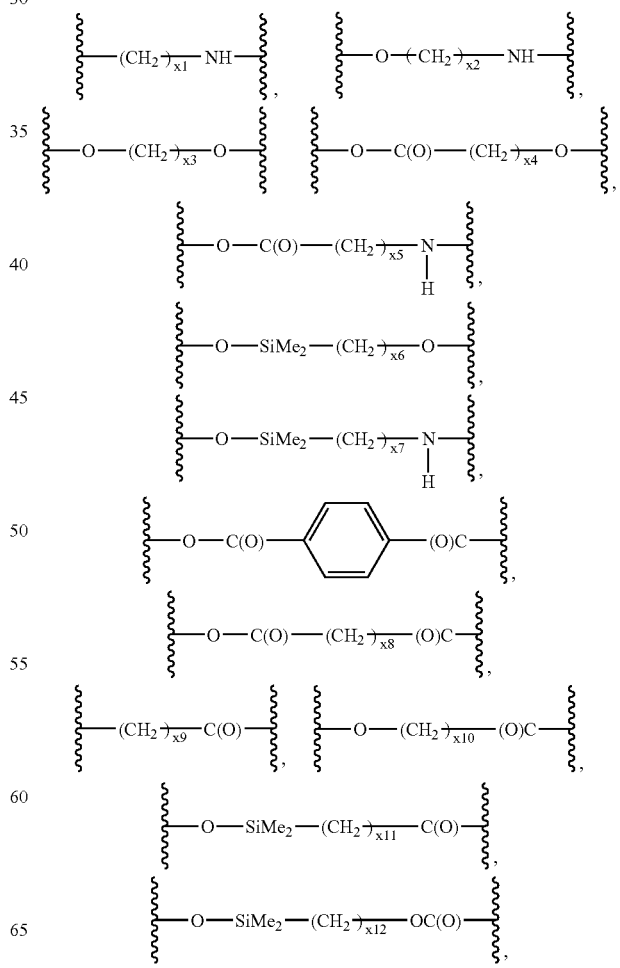

-continued
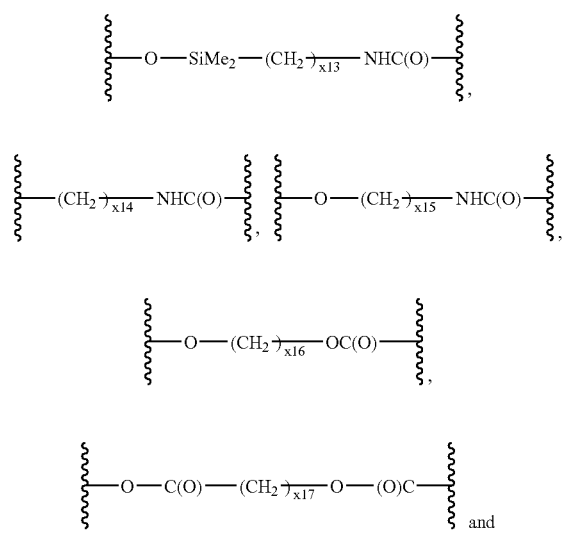
wherein Me is methyl;
M is selected from the group of moieties consisting of
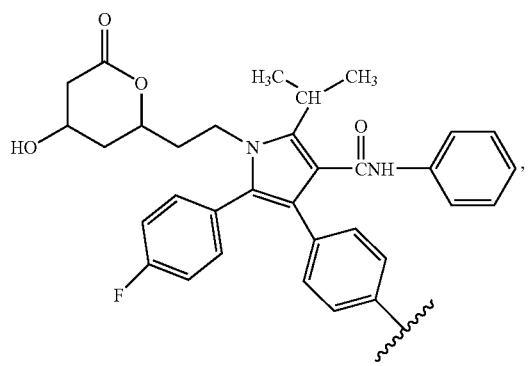
(M1)
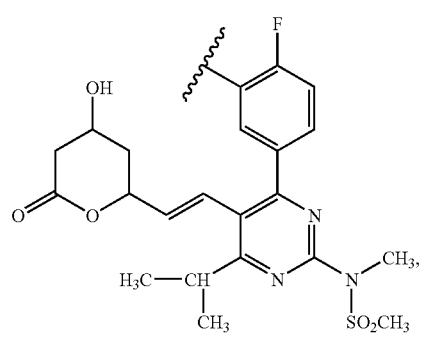
(M4)
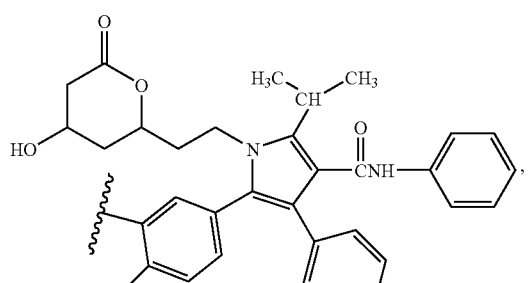
(M3)
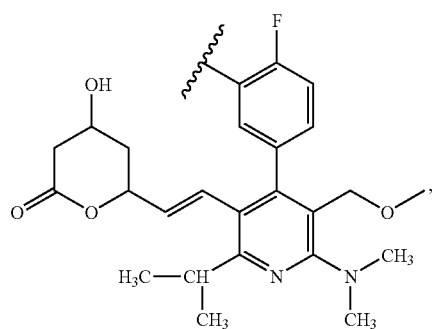
(M5)
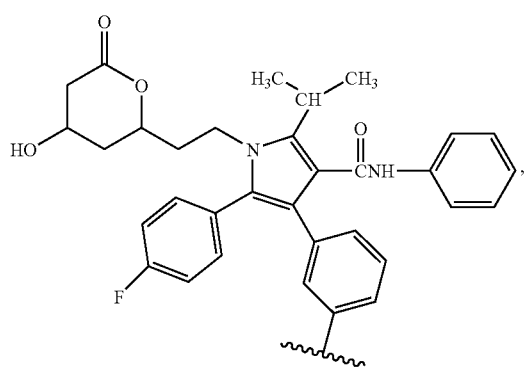
(M6)
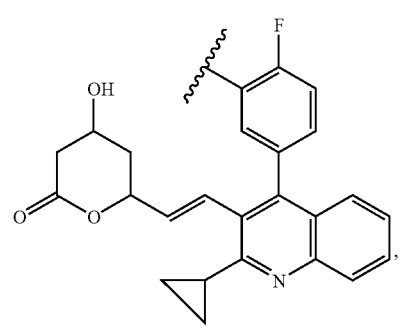
(M7)

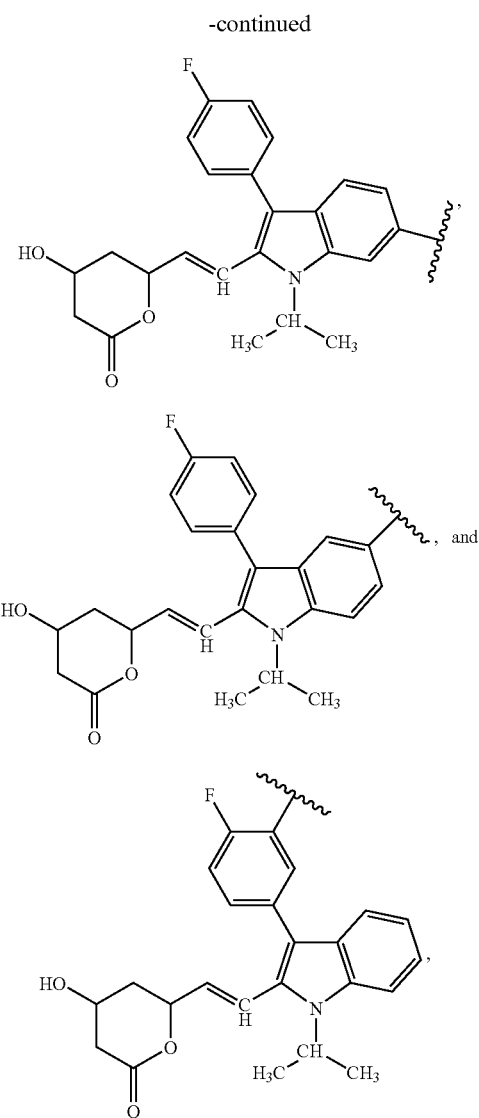

pharmaceutically acceptable salts of the moieties (M1) and (M3) to (M10) and free acids of the moieties (M1) and (M3) to (M10);

R² and R³ can be the same or different and each is independently selected from the group consisting of hydrogen, alkyl and aryl;

R⁶, R⁷ and R⁸ can be the same or different and each is independently selected from the group consisting of hydrogen, alkyl, aryl and arylalkyl; and each R⁹ is independently alkyl, aryl or arylalkyl.
each R¹⁰ is independently H or alkyl;
q is 0 or 1;
r is 0 or 1;
m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;
x1 is 1 to 10;
x2 is 1 to 10;
x3 is 1 to 10;
x4 is 1 to 10;
x5 is 1 to 10;
x6 is 1 to 10;
x7 is 1 to 10;
x8 is 1 to 10;
x9 is 1 to 10;
x10 is 1 to 10;
x11 is 1 to 10;
x12 is 1 to 10;
x13 is 1 to 10;
x14 is 1 to 10;
x15 is 1 to 10; and
x16 is 1 to 10;
x17 is 1 to 10; and
x18 is 1 to 10;
with the proviso that at least one of $Q^1$, $Q^2$, $Q^3$, $Q^4$ and $Q^5$ is -L-M or the sugar residue, disugar residue, trisugar residue, tetrasugar residue, sugar acid, amino sugar, amino acid residue or oligopeptide residue of G is substituted with -L-M.

In another embodiment, the present invention provides a compound represented by the structural formula (IA):

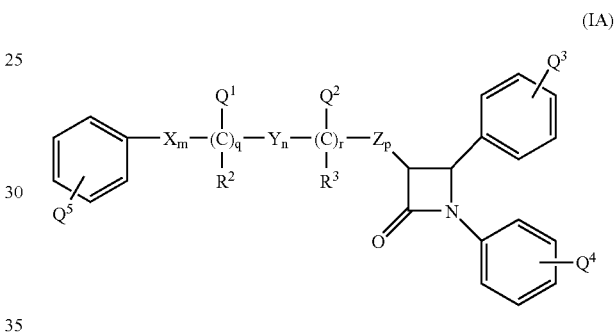

(IA)

or pharmaceutically acceptable isomers, salts, solvates or esters of the compound of Formula (IA), wherein in Formula (IA) above:

X, Y and Z can be the same or different and each is independently selected from the group consisting of —CH₂—, —CH(alkyl)- and —C(alkyl)₂-;

$Q^1$ and $Q^2$ can be the same or different and each is independently selected from the group consisting of H, —(C₀-C₃₀ alkylene)-G, —OR⁶, —OC(O)R⁶, —OC(O)OR⁹, —OC(O)NR⁶R⁷, and -L-M;

$Q^3$ is 1 to 5 substituents independently selected from the group consisting of alkyl, alkenyl, alkynyl, —(C₀-C₃₀ alkylene)-G, —(C₀-C₁₀ alkylene)-OR⁶, —(C₀-C₁₀ alkylene)-C(O)R⁶, —(C₀-C₁₀ alkylene)-C(O)OR⁶, —(C₀-C₁₀ alkylene)-OC(O)R⁶, —(C₀-C₁₀ alkylene)-OC(O)OR⁹, —CH═CH—C(O)R⁶, —CH═CH—C(O)OR⁶,

—C≡C—C(O)OR⁶, —C≡C—C(O)R⁶,

—O—(C₁-C₁₀ alkylene)-OR⁶, —O—(C₁-C₁₀ alkylene)-C(O)R⁶, —O—(C₁-C₁₀ alkylene)-C(O)OR⁶, —CN, —O—(C₁-C₁₀ alkylene)-C(O)NR⁶R⁷, —O—(C₀-C₁₀ alkylene)-C(O)NR⁶NR⁷C(O)OR⁶, —O—(C₁-C₁₀ alkylene)-C(O)(aryl)-N—N═N⁻, —OC(O)—(C₁-C₁₀ alkylene)-C(O)OR⁶, —(C₀-C₁₀ alkylene)-C(O)NR⁶R⁷, —(C₀-C₁₀ alkylene)-OC(O)NR⁶R⁷, —NO₂, —(C₀-C₁₀ alkylene)-NR⁶R⁷, —O—(C₁-C₁₀ alkylene)-NR⁶R⁷, —NR⁶C(O)R⁷, —NR⁶C(O)OR⁸, —NR⁶C(O)NR⁷R⁸, —NR⁶S(O)₀₋₂R⁹, —N(S(O)₀₋₂R⁹)₂, —CHNOR⁶, —C(O)NR⁶R⁷, —C(O)NR⁶NR⁶R⁷, —S(O)₀₋₂NR⁶R⁷, —S(O)₀₋₂R⁹, —O—C(O)—C₁-C₁₀ alkylene)-C(O)NR⁶R⁷, —OC(O)—(C₁-C₁₀ alkylene)-NR⁶C(O)O-(alkylaryl), —P(O)(OR¹⁰)₂, —(C₁-C₁₀ alkylene)-OSi(alkyl)₃, —CF₃, —OCF₃, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

$Q^4$ is 1 to 5 substituents independently selected from the group consisting of alkyl, alkenyl, alkynyl, —(C₀-C₃₀ alkylene)-G, —(C₀-C₁₀ alkylene)-OR⁶, —(C₀-C₁₀ alkylene)-C(O)R⁶, —(C₀-C₁₀ alkylene)-C(O)OR⁶, —(C₀-C₁₀ alkylene)-OC(O)R⁶, —(C₀-C₁₀ alkylene)-OC(O)OR⁹, —CH═CH—C(O)R⁶, —CH═CH—C(O)OR⁶,

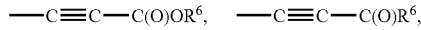

—O—(C₁-C₁₀ alkylene)-OR⁶, —O—(C₁-C₁₀ alkylene)-C(O)R⁶, —O—(C₁-C₁₀ alkylene)-C(O)OR⁶, —CN, —O—(C₁-C₁₀ alkylene)-C(O)NR⁶R⁷, —O—(C₀-C₁₀ alkylene)-C(O)NR⁶NR⁷C(O)OR⁶, —O—(C₁-C₁₀ alkylene)-C(O)(aryl)-N—N═N⁻, —OC(O)—(C₁-C₁₀ alkylene)-C(O)OR⁶, —(C₀-C₁₀ alkylene)-C(O)NR⁶R⁷, —(C₀-C₁₀ alkylene)-OC(O)NR⁶R⁷, —NO₂, —(C₀-C₁₀ alkylene)-NR⁶R⁷, —O—(C₁-C₁₀ alkylene)-NR⁶R⁷, —NR⁶C(O)R⁷, —NR⁶C(O)OR⁹, —NR⁶C(O)NR⁷R⁸, —NR⁶S(O)₀₋₂R⁹, —N(S(O)₀₋₂R⁹)₂, —CHNOR⁶, —C(O)NR⁶R⁷, —C(O)NR⁶NR⁶R⁷, —S(O)₀₋₂NR⁶R⁷, —S(O)₀₋₂R⁹, —O—C(O)—C₁-C₁₀ alkylene)-C(O)NR⁶R⁷, —OC(O)—(C₁-C₁₀ alkylene)-NR⁶C(O)O-(alkylaryl), —P(O)(OR¹⁰)₂, —(C₁-C₁₀ alkylene)-OSi(alkyl)₃, —CF₃, —OCF₃, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

$Q^5$ is 1 to 5 substituents independently selected from the group consisting of alkyl, alkenyl, alkynyl, —(C₀-C₃₀ alkylene)-G, —(C₀-C₁₀ alkylene)-OR⁶, —(C₀-C₁₀ alkylene)-C(O)R⁶, —(C₀-C₁₀ alkylene)-C(O)OR⁶, —(C₀-C₁₀ alkylene)-OC(O)R⁶, —(C₀-C₁₀ alkylene)-OC(O)OR⁹, —CH═CH—C(O)R⁶, —CH═CH—C(O)OR⁶,

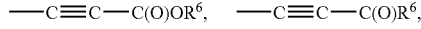

—O—(C₁-C₁₀ alkylene)-OR⁶, —O—(C₁-C₁₀ alkylene)-C(O)R⁶, —O—(C₁-C₁₀ alkylene)-C(O)OR⁶, —CN, —O—(C₁-C₁₀ alkylene)-C(O)NR⁶R⁷, —O—(C₀-C₁₀ alkylene)-C(O)NR⁶NR⁷C(O)OR⁶, —O—(C₁-C₁₀ alkylene)-C(O)(aryl)-N—N═N⁻, —OC(O)—(C₁-C₁₀ alkylene)-C(O)OR⁶, —(C₀-C₁₀ alkylene)-C(O)NR⁶R⁷, —(C₀-C₁₀ alkylene)-OC(O)NR⁶R⁷, —NO₂, —(C₀-C₁₀ alkylene)-NR⁶R⁷, —O—(C₁-C₁₀ alkylene)-NR⁶R⁷, —NR⁶C(O)R⁷, —NR⁶C(O)OR⁹, —NR⁶C(O)NR⁷R⁸, —NR⁶S(O)₀₋₂R⁹, —N(S(O)₀₋₂R⁹)₂, —CHNOR⁶, —C(O)NR⁶R⁷, —C(O)NR⁶NR⁶R⁷, —S(O)₀₋₂NR⁶R⁷, —S(O)₀₋₂R⁹, —O—C(O)—(C₁-C₁₀ alkylene)-C(O)NR⁶R⁷, —OC(O)—(C₁-C₁₀ alkylene)-NR⁶C(O)O-(alkylaryl), —P(O)(OR¹⁰)₂, —(C₁-C₁₀ alkylene)-OSi(alkyl)₃, —CF₃, —OCF₃, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

wherein optionally one or more carbon atoms of the —(C₀-C₃₀ alkylene)- radical of $Q^1$, $Q^2$, $Q^3$, $Q^4$ and $Q^5$ is independently replaced by —O—, —C(O)—, —CH═CH—,

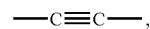

—N(alkyl)-, —N(alkylaryl)- or —NH—;

G is selected from the group consisting of a sugar residue, disugar residue, trisugar residue, tetrasugar residue, sugar acid, amino sugar, amino acid residue, oligopeptide residue comprising 2 to 9 amino acids, trialkylammoniumalkyl radical and —S(O)₂—OH, wherein optionally the sugar residue, disugar residue, trisugar residue, tetrasugar residue, sugar acid, amino sugar, amino acid residue or oligopeptide residue of G is substituted with -L-M;

L is selected from the group consisting of

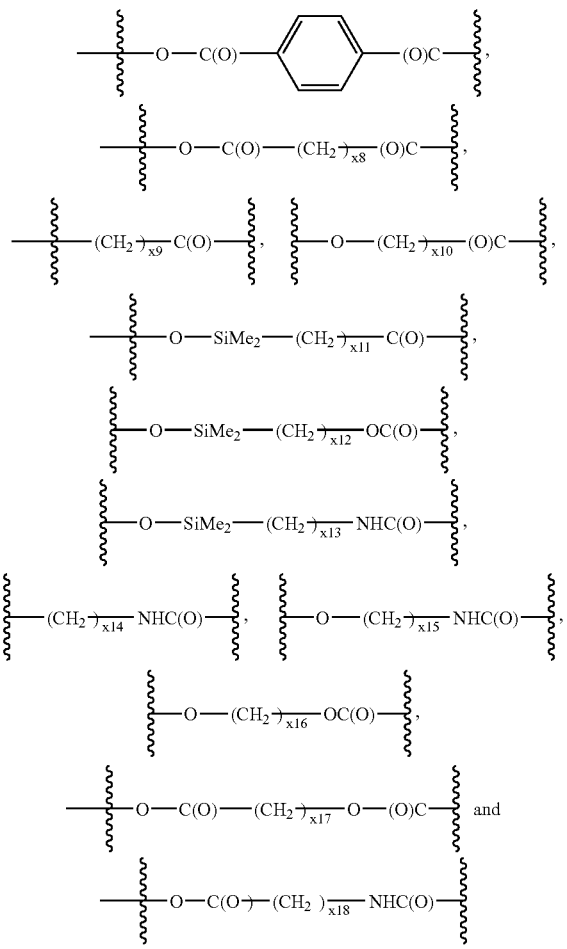

wherein Me is methyl;

M is selected from the group of moieties consisting of

-continued
(M20)
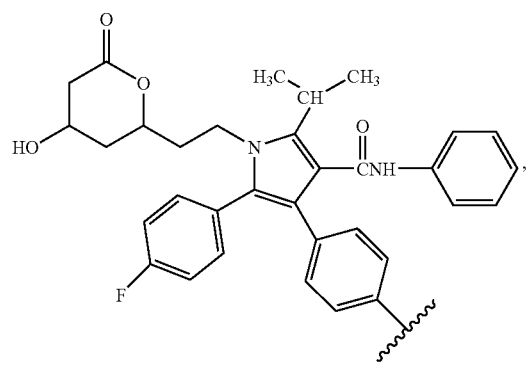
(M21)
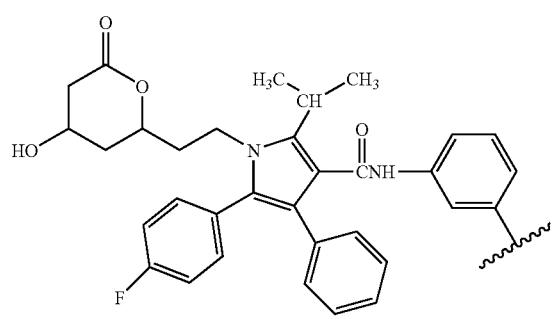
(M22)
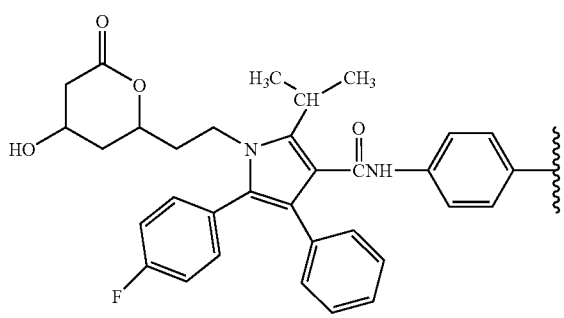
(M23)
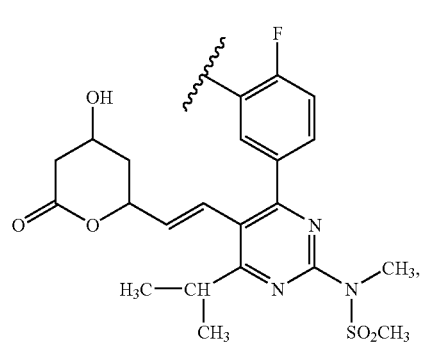
-continued
(M24)
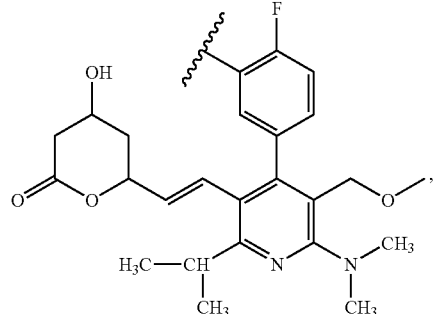
(M25)
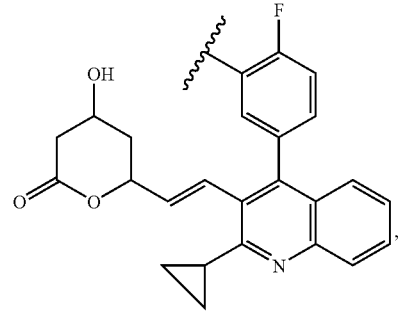
(M26)
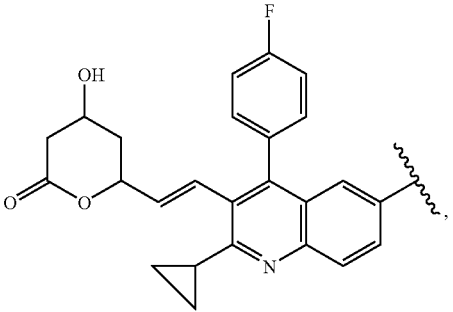
(M27)
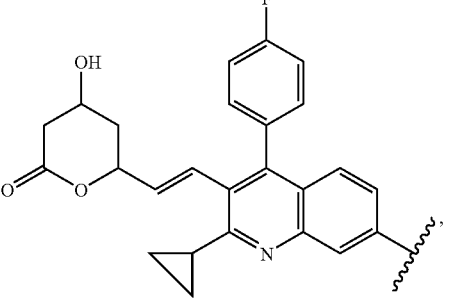
(M28)
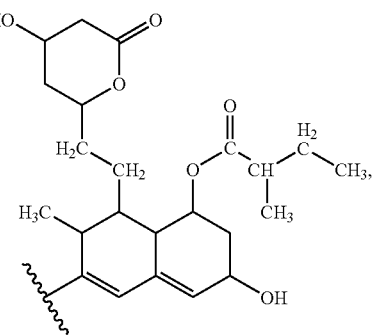

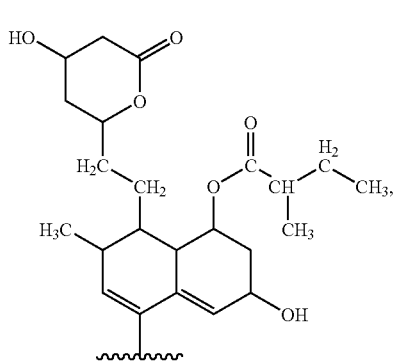
(M29)

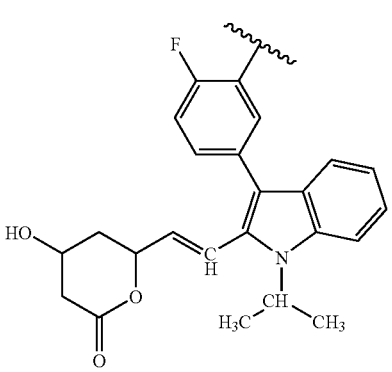
(M33)

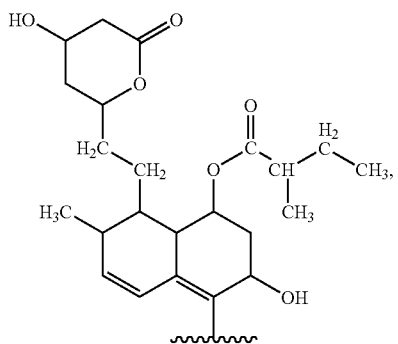
(M30)

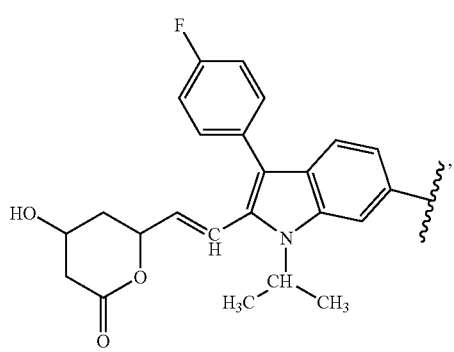
(M31)

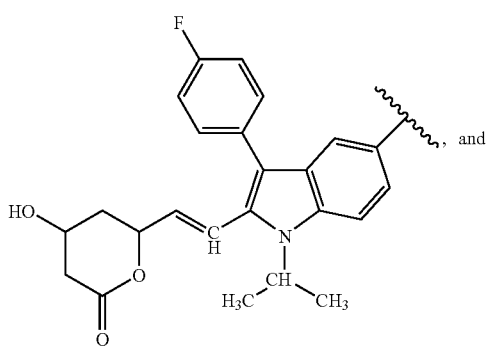
(M32), and and pharmaceutically acceptable salts of moieties (M1) to (M33);

$R^2$ and $R^3$ can be the same or different and each is independently selected from the group consisting of hydrogen, alkyl and aryl;

$R^6$, $R^7$ and $R^8$ can be the same or different and each is independently selected from the group consisting of hydrogen, alkyl, aryl and arylalkyl; and each $R^9$ is independently alkyl, aryl or arylalkyl.

each $R^{10}$ is independently H or alkyl;

q is 0 or 1;

r is 0 or 1;

m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

x8 is 1 to 10;
x9 is 1 to 10;
x10 is 1 to 10;
x11 is 1 to 10;
x12 is 1 to 10;
x13 is 1 to 10;
x14 is 1 to 10;
x15 is 1 to 10; and
x16 is 1 to 10;
x17 is 1 to 10; and
x18 is 1 to 10;

with the proviso that at least one of $Q^1$, $Q^2$, $Q^3$, $Q^4$ and $Q^5$ is -L-M or the sugar residue, disugar residue, trisugar residue, tetrasugar residue, sugar acid, amino sugar, amino acid residue or oligopeptide residue of G is substituted with -L-M.

Pharmaceutical formulations or compositions for the treatment or prevention of a vascular condition, diabetes, obesity, stroke, lowering a concentration of a sterol or stanol in plasma of a mammal, preventing demyelination or treating Alzheimer's disease and/or regulating levels of amyloid β peptides in a subject comprising a therapeutically effective amount of the above compounds and a pharmaceutically acceptable carrier also are provided.

Methods of treating or preventing a vascular condition, diabetes, obesity, stroke, lowering a concentration of a sterol or stanol in plasma of a mammal, preventing demyelination or treating Alzheimer's disease and/or regulating levels of amyloid β peptides in a subject comprising the step of administering to a subject in need of such treatment an effective amount of the above compounds of Formula (I) or (IA) also are provided.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

In its many embodiments, the present invention provides a novel class of compounds of Formulae (I) and (IA) above, processes for producing such compounds, pharmaceutical formulations or compositions comprising one or more of such compounds, methods of preparing the same, and methods of treatment, prevention, inhibition or amelioration of one or more conditions or diseases associated with vascular conditions or other conditions such as are discussed in detail below.

The compounds of Formulae (I) and (IA) are capable of being metabolized in vivo to form a sterol and/or stanol absorption inhibitor compound and a sterol biosynthesis inhibitor compound. As used herein, "sterol absorption inhibitor" means a compound capable of inhibiting the absorption of one or more sterols, including but not limited to cholesterol and phytosterols (such as sitosterol, campesterol, stigmasterol and avenosterol) when administered in a therapeutically effective (sterol absorption inhibiting) amount to a subject or human. "Stanol absorption inhibitor" means a compound capable of inhibiting the absorption of one or more 5α-stanols (such as cholestanol, 5α-campestanol, 5α-sitostanol) when administered in a therapeutically effective (stanol absorption inhibiting) amount to a subject or human. The sterol or stanol absorption inhibitor can inhibit the absorption of cholesterol from the intestinal lumen into enterocytes, leading to a decrease in the delivery of intestinal sterol or stanol, respectively, to the liver. "Sterol biosynthesis inhibitor" means a compound, such as a 3-hydroxy-3-methylglutaryl coenzyme A (HMG CoA) reductase inhibitor, that blocks hydroxymethylglutaryl coenzyme A (HMG-CoA) reductase, which is the rate-limiting enzyme in hepatic cholesterol synthesis.

In an alternative embodiment, compounds of Formulae (I) and (IA) can have dual functionality, i.e., can exhibit sterol and/or stanol absorption inhibiting properties and also block hydroxymethylglutaryl coenzyme A (HMG-CoA) reductase.

Referring now to Formulae (I) and (IA), in one embodiment of the present invention, X, Y and Z are each —CH$_2$—.

The sum of m, n, p, q and r is preferably 2, 3 or 4, more preferably 3. Also preferred are compounds of Formulae (I) and (IA) in which p, q and n are each zero, r is 1 and m is 2 or 3.

In one embodiment, m, n and r are each zero, q is 1, p is 2, and Z is —CH$_2$—. Also preferred are compounds wherein m, n and r are each zero, q is 1, p is 2, and Z is —CH$_2$—, Q$^1$ is —OR$^6$, wherein R$^6$ is hydrogen and Q$^5$ is fluorine.

R$^2$ and R$^3$ are each preferably hydrogen.

In one embodiment, Q$^1$ and Q$^2$ can be —OR$^6$ wherein R$^6$ is hydrogen, or a group readily metabolizable to a hydroxyl (such as —O(CO)R$^6$, —O(CO)OR$^9$ and —O(CO)NR$^6$R$^7$, defined above).

In another embodiment Q$^4$ is halo or —OR$^6$.
In another embodiment, Q$^1$ is —OR$^6$ wherein R$^6$ is H.
In yet another embodiment, Q$^1$ is -L-M.
In another embodiment, Q$^2$ is -L-M.
In another embodiment, Q$^3$ is -L-M.
In another embodiment, Q$^4$ is -L-M.
In another embodiment, Q$^5$ is -L-M.
In another embodiment, Q$^5$ is halo.

In another embodiment, Q$^1$, Q$^2$, Q$^3$, Q$^4$ or Q$^5$ is independently —(C$_0$-C$_{30}$ alkylene)-G. In another embodiment, Q$^1$, Q$^2$ or Q$^3$ is independently —(C$_0$-C$_{30}$ alkylene)-G. In another embodiment, Q$^1$ or Q$^3$ is independently —(C$_0$-C$_{30}$ alkylene)-G.

In one embodiment, G is selected from the group consisting of:

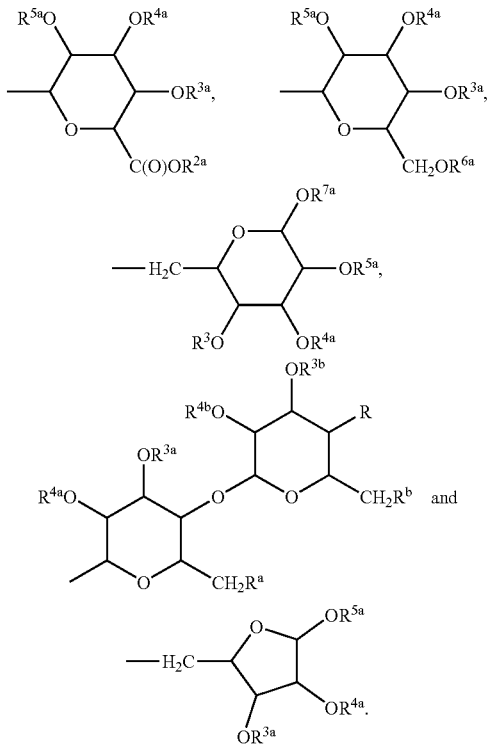

(sugar residues)

wherein R, R$^a$ and R$^b$ can be the same or different and each is independently selected from the group consisting of H, —OH, halo, —NH$^2$, azido, alkoxyalkoxy or -W-R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

R$^{2a}$ and R$^{6a}$ can be the same or different and each is independently selected from the group consisting of H, alkyl, acetyl, aryl and arylalkyl;

R$^{3a}$, R$^{4a}$, R$^{5a}$, R$^{7a}$, R$^{3b}$ and R$^{4b}$ can be the same or different and each is independently selected from the group consisting of H, alkyl, acetyl, arylalkyl, —C(O)alkyl and —C(O)aryl;

R$^{30}$ is independently selected from the group consisting of R$^{32}$-substituted T, R$^{32}$-substituted-T-alkyl, R$^{32}$-substituted-alkenyl, R$^{32}$-substituted-alkyl, R$^{32}$-substituted-cycloalkyl and R$^{32}$-substituted-cycloalkylalkyl;

R$^{31}$ is independently selected from the group consisting of H and alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

R$^{32}$ is 1 to 3 substituents which are each independently selected from the group consisting of H, halo, alkyl, —OH, phenoxy, —CF$_3$, —NO$_2$, alkoxy, methylenedioxy, oxo, alkylsulfanyl, alkylsulfinyl, alkylsulfonyl, —N(CH$_3$)$_2$, —C(O)—NHalkyl, —C(O)—N(alkyl)$_2$, —C(O)-alkyl, —C(O)-alkoxy and pyrrolidinylcarbonyl; or R$^{32}$ is a covalent bond and R$^{31}$, the nitrogen to which it is attached and R$^{32}$ form a pyrrolidinyl, piperidinyl, N-methyl-piperazinyl, indolinyl or morpholinyl group, or a alkoxycarbonyl-substituted pyrrolidinyl, piperidinyl, N-methylpiperazinyl, indolinyl or morpholinyl group.

In another embodiment, G is selected from:

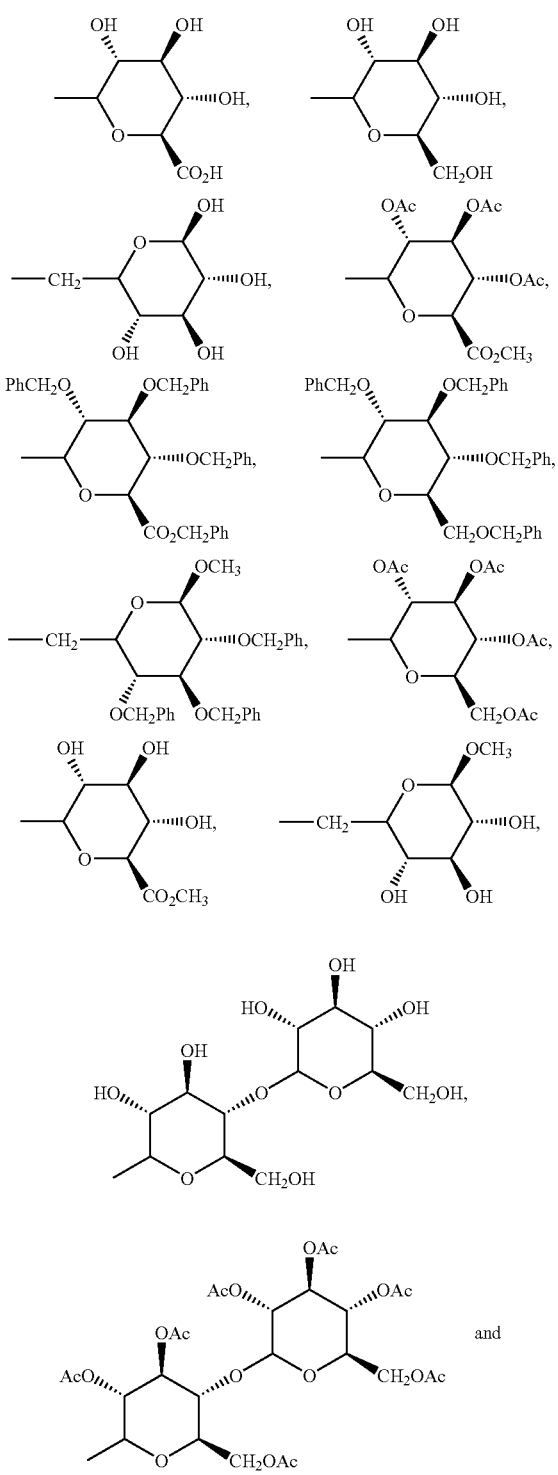

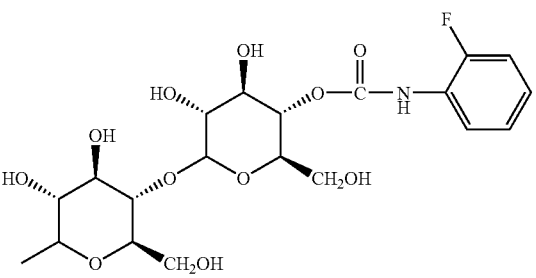

wherein Ac is acetyl and Ph is phenyl.

In another embodiment, optionally one or more carbon atoms of the —(C$_0$-C$_{30}$ alkylene)- radical of Q$^1$, Q$^2$, Q$^3$, Q$^4$ and Q$^5$ is independently replaced by —O—, —C(O)—, —CH═CH—, $$-C \equiv C-,$$

—N(alkyl)-, —N(alkylaryl)- or —NH—, preferably —O—.

The —(C$_0$-C$_{30}$ alkylene)-G substituent is preferably in the 4-position of the phenyl ring to which it is attached.

In one embodiment, L is

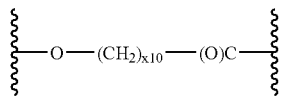

In another embodiment, L is

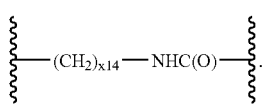

In another embodiment, L is

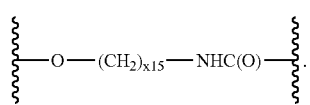

In another embodiment, L is

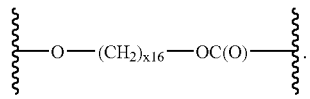

In another embodiment, L is
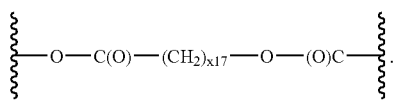
In another embodiment, L is
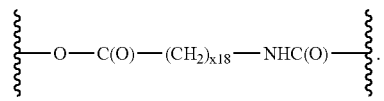
In one embodiment, M is
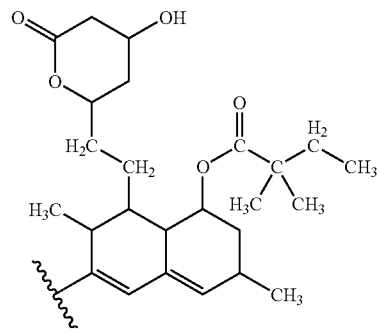
(M11) or pharmaceutically acceptable salts thereof.
In another embodiment, M is
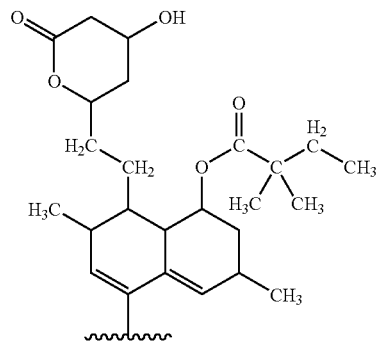
(M12) or pharmaceutically acceptable salts thereof.
In another embodiment, M is
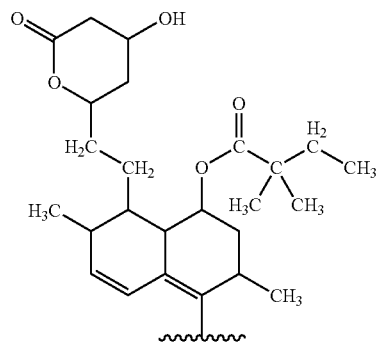
(M13) or pharmaceutically acceptable salts thereof.
One embodiment of the present invention is a compound of Formula (II)
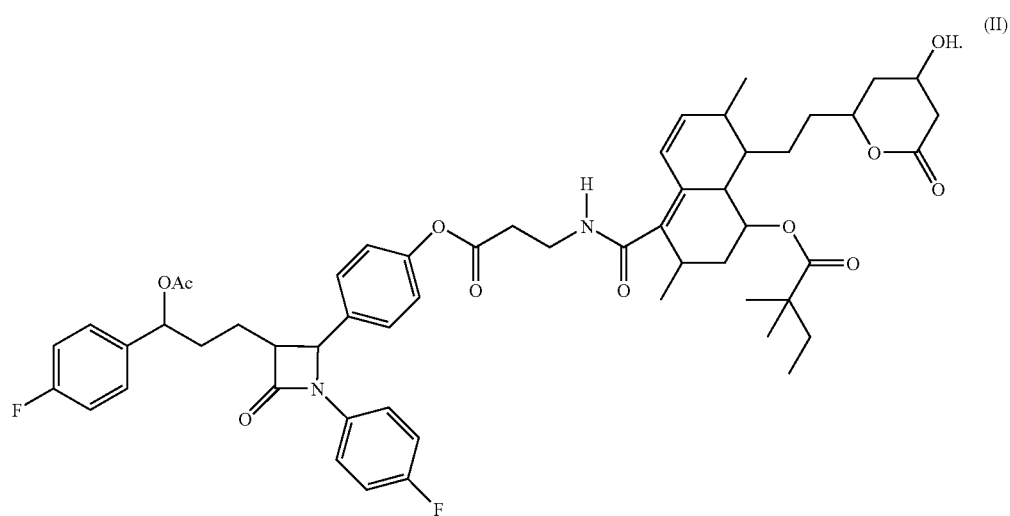

When the compound of Formula (II) is metabolized, one of the compounds (sterol and/or stanol absorption inhibitor) which can be formed is represented by Formula (III) (ezetimibe) below:

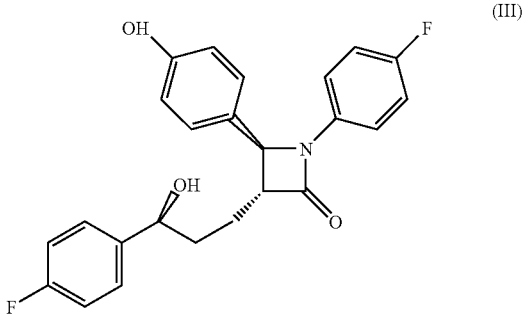

(III)

or pharmaceutically acceptable salts, esters or solvates of the compound of Formula (III).

Alternatively or additionally, when the compound of Formula (II) is metabolized, compounds (sterol biosynthesis inhibitor) which can be formed are represented by Formulae (IV) (carboxylated open acid analog of simvastatin) and (V) (carboxylated analog of simvastatin) below:

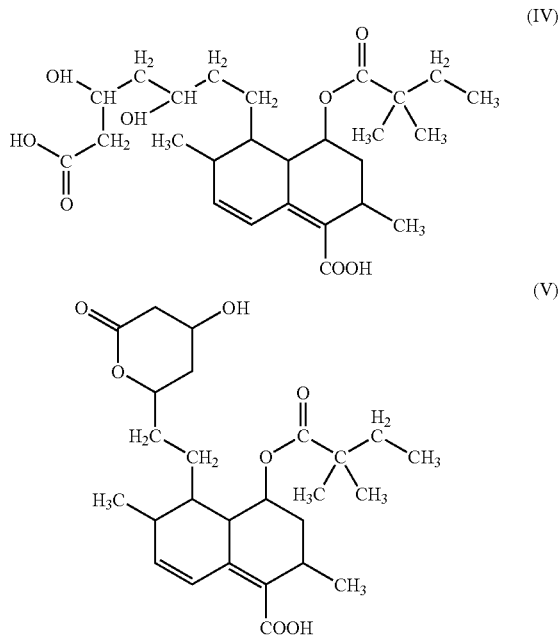

As used above, and throughout the specification, the following terms, unless otherwise indicated, shall be understood to have the following meanings:

"Subject" includes both mammals and non-mammalian animals.

"Mammal" includes humans and other mammalian animals.

The above statements, wherein, for example, $Q^1$ and $Q^2$ are said to be independently selected from a group of substituents, means that $Q^1$ and $Q^2$ are independently selected, but also that where an $Q^1$ or $Q^2$ variable occurs more than once in a molecule, those occurrences are independently selected (e.g., if $Q^1$ is —$OR^6$ wherein $R^6$ is hydrogen, $Q^2$ can be —$OR^6$ wherein $R^6$ is alkyl). Those skilled in the art will recognize that the size and nature of the substituent(s) will affect the number of substituents that can be present.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

As used herein, the term "alkyl" means an aliphatic hydrocarbon group that can be straight or branched and comprises 1 to about 20 carbon atoms in the chain. Preferred alkyl groups comprise 1 to about 12 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. "Lower alkyl" means a group having about 1 to about 6 carbon atoms in a chain that may be straight or branched. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. "Lower alkenyl" means 2 to about 6 carbon atoms in the chain that can be straight or branched. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbutenyl and n-pentenyl.

Where an alkyl or alkenyl chain joins two other variables and is therefore bivalent, the terms alkylene and alkenylene, respectively, are used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

"Alkoxyarylalkoxy" means an alkyl-O-aryl-alkylene-O— group in which the alkyl, alkylene and aryl groups are as previously described. Useful alkoxyarylalkoxy groups can comprise 7 to about 26 carbon atoms, preferably 7 to about 12 carbon atoms. A non-limiting example of a suitable alkoxyarylalkoxy group is methoxybenzyloxy. The alkoxyarylalkoxy is linked to an adjacent moiety through the ether oxygen.

"Alkoxycarbonylalkoxy" means an alkyl-O—C(O)-alkylene-O— group in which the alkyl and alkylene groups are as previously described: Useful alkoxycarbonylalkoxy groups can comprise 3 to about 12 carbon atoms, preferably 3 to about 8 carbon atoms. A non-limiting example of a suitable alkoxycarbonylalkoxy group is CH₃CH₂—O—C(O)—CH₂—O—. The alkoxycarbonylalkoxy is linked to an adjacent moiety through the ether oxygen.

"Alkoxyiminoalkyl" means an alkyl-O—N═CH-alkylene- group in which the alkyl and alkylene groups are as previously described. Useful alkoxyiminoalkyl groups can comprise 2 to about 12 carbon atoms, preferably 2 to about 8 carbon atoms. The alkoxyiminoalkyl is linked to an adjacent moiety through the alkylene group.

"Alkyldioyl" means an ROC(O)-alkylene-C(O)—O— group in which R is alkyl or H and the alkylene group is as previously described. Useful alkyldioyl groups can comprise 2 to about 12 carbon atoms, preferably 2 to about 8 carbon atoms. Non-limiting examples of suitable alkyldioyl groups include 1,3-propanediol. The alkyldioyl is linked to an adjacent moiety through the ester oxygen.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

"Allyloxy" means H₂C═CH—O—. The allyloxy is linked to an adjacent moiety through the ether oxygen.

"Aryl" means an aromatic monocyclic or multicyclic ring system comprising about 5 to about 14 carbon atoms, preferably about 6 to about 10 carbon atoms. The aryl group can be substituted with one or more "ring system substituents" which may be the same or different, and are as defined herein. Non-limiting examples of suitable aryl groups include phenyl, naphthyl, indenyl, tetrahydronaphthyl and indanyl.

"Arylene" means a bivalent phenyl group, including ortho, meta and para-substitution.

"Aralkyl" or "arylalkyl" means an aryl-alkylene- group in which the aryl and alkylene are as previously described. Preferred aralkyls comprise a lower alkyl group. Non-limiting examples of suitable aralkyl groups include benzyl, phenethyl and naphthlenylmethyl. The aralkyl is linked to an adjacent moiety through the alkylene group.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkoxy" or "arylalkyloxy" means an aralkyl-O— group in which the aralkyl group is as previously described. Non-limiting examples of suitable aralkoxy groups include benzyloxy and 1- or 2-naphthalenemethoxy. The bond to the parent moiety is through the ether oxygen. "Aralkoxycarbonyl" means an aralkoxy-C(O)— group in which the aralkoxy group is as previously described.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Aroyloxy" means an aroyl-O— group in which the aroyl group is as previously described. The bond to the parent moiety is through the ether oxygen. Non-limiting examples of suitable groups include benzoyloxy and 1- and 2-naphthoyloxy.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be substituted with one or more "ring system substituents" which may be the same or different, and are as defined below. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornyl, adamantyl and the like. "Cycloalkylene" refers to a corresponding bivalent ring, wherein the points of attachment to other groups include all positional isomers.

"Dioxolanyl" means

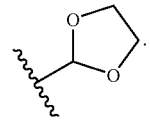

"Halo" refers to fluorine, chlorine, bromine or iodine radicals. Preferred are fluoro, chloro or bromo, and more preferred are fluoro and chloro.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. The heteroatom(s) interrupt a carbocyclic ring structure and have a sufficient number of delocalized pi electrons to provide aromatic character, provided that the rings do not contain adjacent oxygen and/or sulfur atoms. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be oxidized to form the corresponding N-oxide. All regioisomers are contemplated, e.g., 2-pyridyl, 3-pyridyl and 4-pyridyl. Examples of useful 6-membered heteroaryl groups include pyridyl, pyrimidinyl, pyrazinyl, pyridazinyl and the like and the N-oxides thereof. Examples of useful 5-membered heteroaryl rings include furyl, thienyl, pyrrolyl, thiazolyl, isothiazolyl, imidazolyl, pyrazolyl and isoxazolyl. Useful bicyclic groups are benzo-fused ring systems derived from the heteroaryl groups named above, e.g., quinolyl, phthalazinyl, quinazolinyl, benzofuranyl, benzothienyl and indolyl.

"Heteroarylalkyl" or "heteroaralkyl" means a heteroaryl-alkylene- group in which the heteroaryl and alkyl are as previously described. Preferred heteroaralkyls contain a lower alkyl group. Non-limiting examples of suitable heteroaralkyl groups include pyridylmethyl, 2-(furan-3-yl)ethyl and quinolin-3-ylmethyl. The bond to the parent moiety is through the alkylene. "Heteroarylalkoxy" means a heteroaryl-alkylene-O— group in which the heteroaryl and alkylene are as previously described.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylalkyl" means a heterocyclyl-alkylene-group in which the heterocyclyl and alkylene groups are as previously described. Preferred heterocyclylalkyls contain a lower alkylene group. The bond to the parent moiety is through the alkylene. "Heterocyclylcarbonyl" means a heterocyclyl-C(O)— group in which the heterocyclyl is as previously described. Preferred heterocyclylcarbonyls contain a lower alkyl group. The bond to the parent moiety is through the carbonyl. "Heterocyclylcarbonylalkoxy" means a heterocyclyl-C(O)-alkoxy- group in which the heterocyclyl and alkoxy are as previously described.

"Ring system substituent" means a substituent attached to an aromatic or non-aromatic ring system that, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Sugar residue" means a moiety derived from an aldose or ketose that has 3 to 7 carbon atoms and may belong to the D or L series. Non-limiting examples of suitable aldoses from which the sugar residue can be formed include glucose, mannose, galactose, ribose, erythrose and glyceraldehydes. A non-limiting example of a suitable ketose from which the sugar residue can be formed is fructose.

"Disugar residue" means a moiety derived from a sugar that can be hydrolyzed to two monosaccharide molecules. Non-limiting examples of suitable compounds from which the disugar residue can be formed include maltose, lactose, cellobiose and sucrose.

Examples of sugar residues and disugar residues include those moieties G listed in detail above.

Di-, tri- or tetrasaccharides are formed by acetal-like binding of two or more sugars. The bonds may be in α or β form. "Trisugar residue" means a moiety derived from a sugar that can be hydrolyzed to three monosaccharide molecules. "Tetrasugar residue" means a moiety derived from a sugar that can be hydrolyzed to four monosaccharide molecules.

If the sugar is substituted, the substitution is preferably at the hydrogen atom of an OH group of the sugar.

"Sugar acid" means an sugar residue, such as can be formed from glucuronic acid, galacturonic acid, gluconic acid, galactonic acid, mannonic acid, glucaric acid and galactaric acid.

"Amino sugar" means an amino-substituted sugar residue such as can be formed from glucosamine, galactosamine, glucamine or 3-amino-1,2-propanediol.

Suitable protective groups for the hydroxyl groups of the sugars include benzyl, acetyl, benzoyl, pivaloyl, trityl, tert-butyidimethylsilyl, benzilidene, cyclohexidene or isopropylidene protective groups.

"Amino acid residue" means a moiety derived from an amino acid. The amino acid moiety can be prepared from the D or L forms of the amino acid. Non-limiting examples of suitable amino acids from which the amino acid residue can be prepared include alanine, arginine, asparagine, aspartic acid, cysteine, cystine, glutamic acid, glutamine, glycine, histidine, hydroxylysine, hydroxyproline, isoleucine, leucine, lysine, methionine, phenylanine, proline, serine, threonine, tryptophane, tyrosine, valine, 2-aminoadipic acid, 3-aminoadipic acid, beta-alanine, 2-aminobutyric acid, 4-aminobutyric acid, piperidino carboxylic acid, 6-aminocaproic acid, 2-aminoheptanoic acid, 2-(2-thienyl)glycine, penicillamine, N-ethylasparagine, 2-aminoisobutyric acid, 2-aminoisobutyric acid, 2-aminopimelic acid, 2,4-diaminobutyric acid, desmosine, 2,2-diaminopimelic acid, 2,3-diaminopropioninc acid, N-ethylglycine, 3-(2-thienyl)alanine, sarcosine, N-methylisoleucine, 6-N-methyllysine, N-methylvaline, norvaline, norleucine, ornithine and N-methylglycine.

"Oligopeptide residue" means the residue of a peptide constructed of 2 to 9 of the amino acids mentioned above.

"Trialkylammonium alkyl radical" means the group

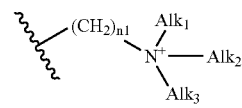

wherein n1 is 0 to 10 and $Alk_1$, $Alk_2$ and $Alk_3$ can be the same or different and each is a straight or branched alkyl radical having 1 to 20 carbon atoms.

Compounds of the invention have at least one asymmetrical carbon atom and therefore all isomers, including enantiomers, stereoisomers, rotamers, tautomers and racemates of the compounds of Formulae (I) and (II) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulae (I) or (II). Isomers may also include geometric isomers, e.g., when a double bond is present. Polymorphous forms of the compounds of Formulae (I) or (II), whether crystalline or amorphous, also are contemplated as being part of this invention.

Those skilled in the art will appreciate that for some of the compounds of the Formulae (I) or (II), one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of the invention with a carboxylic acid group can form pharmaceutically acceptable esters with an alcohol. Examples of suitable alcohols include methanol and ethanol.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof (e.g., a prodrug on being brought to the physiological pH or through enzyme action is converted to the desired drug form). A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Generally, the azetidinone portion of the compounds of Formula (I) can be prepared by a variety of methods well known to those skilled in the art, for example such as are disclosed in U.S. Pat. Nos. 5,631,365, 5,767,115, 5,846,966, 6,207,822, PCT Patent Application No. 02/079174 and PCT Patent Application WO 93/02048, each of which is incorporated herein by reference, and in the Example below. Preferably the azetidinone is prepared from ezetimibe, such as can be prepared by routine separation methods from ZETIA® ezetimibe formulation that is commercially available from Schering-Plough Corporation.

The statin compound for preparing the -M portion of the molecule can be prepared by a variety of methods, for example the statin compound for preparing M11, M12 or M13 can be prepared by methods such as are disclosed in PCT WO 98/12188, U.S. Pat. Nos. 5,763,653, 5,763,646, 4,444,784, 4,582,915, 4,820,850, or by routine separation methods from ZOCOR® simvastatin formulation which is commercially available from Merck & Co. Inc. The compound for preparing M14 or M15 can be prepared by methods such as are disclosed in U.S. Pat. Nos. 4,231,938, 4,294,926, 5,763,653, 4,323,648, 4,916,239, 5,763,646 or by routine separation methods from MEVACOR® lovastatin formulation which is commercially available from Merck & Co. Inc. The compound for preparing M1, M3, M4, M17, M19, M20, M21 or M22 can be prepared by methods such as are disclosed in U.S. Pat. Nos. 5,273,995, 4,681,893, 5,969,156 or by routine separation methods from LIPITOR® atorvastatin formulation which is commercially available from Pfizer. The compound for preparing M6 or M23 can be prepared by methods such as are disclosed in U.S. Pat. No. 5,260,440 or by routine separation methods from CRESTOR® rosuvastatin formulation that is commercially available from AstraZeneca. The compound for preparing M24 can be prepared by methods such as are disclosed in U.S. Pat. Nos. 5,006,530 and 5,177,080. The compound for preparing M7, M25, M26, or M27 can be prepared by methods such as are disclosed in U.S. Pat. Nos. 5,872,130, 5,856,336, 5,011,930 and 5,854,259. The compound for preparing M28, M29 or M30 can be prepared by methods such as are disclosed in U.S. Pat. Nos. 4,346,227, 4,537,859, 4,410,629 or by routine separation methods from PRAVACHOL® pravastatin formulation which is commercially available from Bristol-Myers Squibb. The compound for preparing M8, M9, M10, M31, M32 or M33 can be prepared by methods such as are disclosed in U.S. Pat. Nos. 5,354,772 and 4,739,073 or by routine separation methods from LESCOL® fluvastatin formulation that is commercially available from Novartis.

In general, the compounds of Formulae (I) and (IA) can be prepared through the general routes described below in Scheme 1. The azetidinone portion of the molecule and -M portion of the molecule can be linked by linker -L- as shown for example in Scheme 1 below. Non-limiting examples of suitable compounds for preparing linker

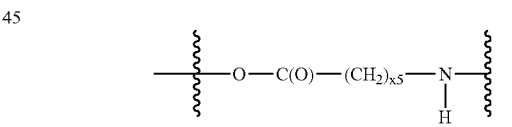

are from N-Boc-β-alanine, N-Boc glycine and N-Boc-6-aminocaproic acid, respectively, in a manner as shown below:

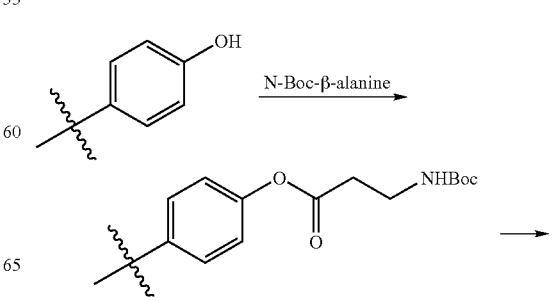

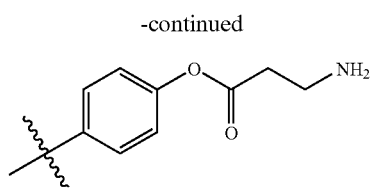
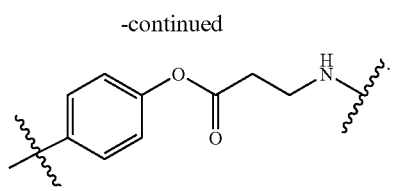
Scheme 1. General Synthesis: Ezetimibe Linked to Simvastatin
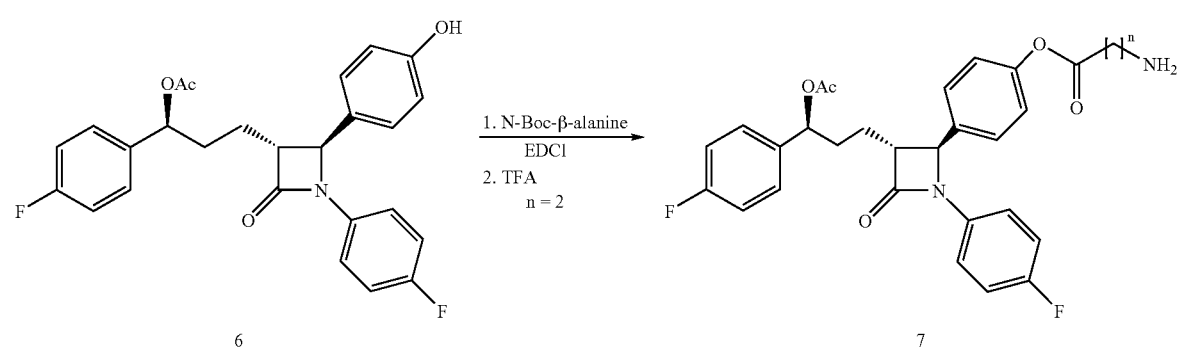
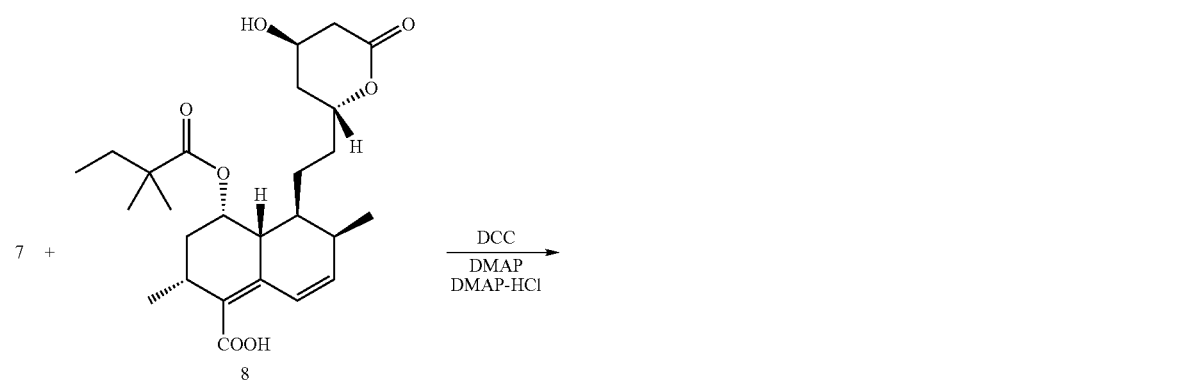
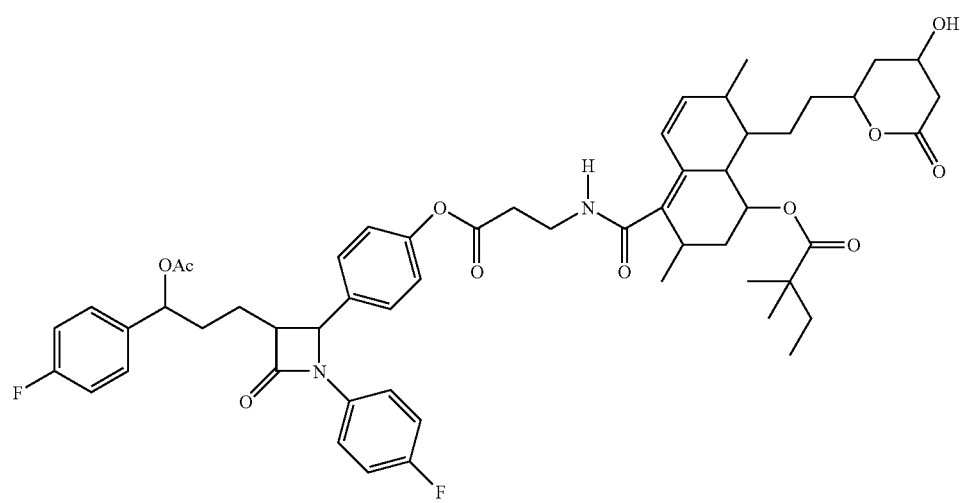

Generally, in Scheme 1, treatment of the starting azetidinone (for example acetoxy-protected ezetimibe 6) with an amino acid in which the amine functionality can be blocked with a suitable protective group such as a butoxycarbonyl (Boc) and an amide coupling reagent such as 1-(3-Dimethylaminopropyl)-3-ethylcarbodiimide gives rise to the protected amino ester which upon treatment with mild acid such as trifluoroacetic acid gives the desired amine-substituted azetidinone 7. Selection of solvents and additives for the amide coupling reaction may vary and would be obvious to one skilled in the art. Amine-substituted azetidinone 7 is reacted with carboxy-substituted statin 8 (for example simvastatin) and pyridine to form compound 9 of the present invention.

The daily dose of the compound of Formula (I) can range from about 0.1 to about 1000 mg per day, preferably about 0.25 to about 100 mg/day, and more preferably about 5, 10, 20, 30, 40, 50, 60 70, 80, 90 or 100 mg per day, given in a single dose or 2-4 divided doses. The exact dose, however, is determined by the attending clinician and is dependent on the potency of the compound administered, the age, weight, condition and response of the patient. The phrases "effective amount" and "therapeutically effective amount" mean that amount of a compound of Formula I, and other pharmacological or therapeutic agents described below, that will elicit a biological or medical response of a tissue, system, animal or mammal that is being sought by the administrator (such as a researcher, doctor or veterinarian) which includes alleviation of the symptoms of the condition or disease being treated and the prevention, slowing or halting of progression of one or more conditions, for example vascular conditions, such as hyperlipidaemia (for example atherosclerosis, hypercholesterolemia or sitosterolemia), vascular inflammation, stroke, diabetes, obesity and/or to reduce the level of sterol(s) (such as cholesterol) or stanol(s) in the plasma of a subject. As used herein, "vascular" comprises cardiovascular, cerebrovascular, peripheral vascular and combinations thereof. The formulations or compositions, combinations and treatments of the present invention can be administered by any suitable means which produce contact of these compounds with the site of action in the body, for example in the plasma, liver or small intestine of a mammal or human.

For administration of pharmaceutically acceptable salts of the above compounds, the weights indicated above refer to the weight of the acid equivalent or the base equivalent of the therapeutic compound derived from the salt.

In one embodiment of the present invention, the compositions or therapeutic combinations can further comprise one or more pharmacological or therapeutic agents or drugs such as lipid-lowering agents discussed below. As used herein, "combination therapy" or "therapeutic combination" means the administration of two or more therapeutic agents, such as a compound of Formula (I) and a lipid-lowering or antihypertensive agent, to prevent or treat a condition as described above. Such administration includes coadministration of these therapeutic agents in a substantially simultaneous manner, such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating the condition. A potential advantage of the combination therapy disclosed herein may be a reduction in the required amount of an individual therapeutic compound or the overall total amount of therapeutic compounds that are effective in treating the condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

Non-limiting examples of additional cholesterol biosynthesis inhibitors for use in the compositions, therapeutic combinations and methods of the present invention include squalene synthase inhibitors, squalene epoxidase inhibitors and mixtures thereof. Non-limiting examples of suitable HMG CoA synthetase inhibitors include L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy] benzene-methanamine hydrochloride) and other sterol biosynthesis inhibitors such as DMP-565. Generally, a total daily dosage of additional cholesterol biosynthesis inhibitor(s) can range from about 0.1 to about 160 mg per day, and preferably about 0.2 to about 80 mg/day in single or 2-3 divided doses.

In another preferred embodiment, the composition or treatment comprises the compound of Formula (I) in combination with one or more peroxisome proliferator-activated receptor(s) activator(s). In this embodiment, preferably the peroxisome proliferator-activated receptor activator(s) is a fibric acid derivative such as gemfibrozil, clofibrate and/or fenofibrate.

In another alternative embodiment, the compositions, therapeutic combinations or methods of the present invention can further comprise one or more bile acid sequestrants (insoluble anion exchange resins), coadministered with or in combination with the compound of Formula (I) discussed above. Bile acid sequestrants bind bile acids in the intestine, interrupting the enterohepatic circulation of bile acids and causing an increase in the faecal excretion of steroids. Bile acid sequestrants can lower intrahepatic cholesterol and promote the synthesis of apo B/E (LDL) receptors that bind LDL from plasma to further reduce cholesterol levels in the blood. Non-limiting examples of suitable bile acid sequestrants include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), and colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo). Generally, a total daily dosage of bile acid sequestrant(s) can range from about 1 to about 50 grams per day, and preferably about 2 to about 16 grams per day in single or 2-4 divided doses.

In an alternative embodiment, the compositions or treatments of the present invention can further comprise one or more ileal bile acid transport ("IBAT") inhibitors (or apical sodium co-dependent bile acid transport ("ASBT") inhibitors) coadministered with or in combination with the compound of Formula (I) discussed above. The IBAT inhibitors can inhibit bile acid transport to reduce LDL cholesterol levels. Non-limiting examples of suitable IBAT inhibitors include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference. Generally, a total daily dosage of IBAT inhibitor(s) can range from about 0.01 to about 1000 mg/day, and preferably about 0.1 to about 50 mg/day in single or 2-4 divided doses.

In another alternative embodiment, the compositions or treatments of the present invention can further comprise nicotinic acid (niacin) and/or derivatives thereof coadministered with or in combination with the compound of Formula (I) discussed above. As used herein, "nicotinic acid derivative" means a compound comprising a pyridine-3-carboxylate structure or a pyrazine-2-carboxylate structure, including acid forms, salts, esters, zwitterions and tautomers, where available. Examples of nicotinic acid derivatives include niceritrol, nicofuranose and acipimox (5-methyl pyrazine-2-carboxylic acid 4-oxide). Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos. Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

In another alternative embodiment, the compositions or treatments of the present invention can further comprise one or more AcylCoA:Cholesterol O-acyltransferase ("ACAT") Inhibitors, which can reduce LDL and VLDL levels, coadministered with or in combination with the compound of Formula (I) discussed above. ACAT is an enzyme responsible for esterifying excess intracellular cholesterol and may reduce the synthesis of VLDL, which is a product of cholesterol esterification, and overproduction of apo B-100-containing lipoproteins. Non-limiting examples of useful ACAT inhibitors include avasimibe, HL-004, lecimibide (DuP-128) and CL-277082 (N-(2,4-difluorophenyl)-N-[[4-(2,2-dimethylpropyl)phenyl]methyl]-N-heptylurea). See P. Chang et al., "Current, New and Future Treatments in Dyslipidaemia and Atherosclerosis", *Drugs* 2000 July; 60(1); 55-93, which is incorporated by reference herein. Generally, a total daily dosage of ACAT inhibitor(s) can range from about 0.1 to about 1000 mg/day in single or 2-4 divided doses.

In another alternative embodiment, the compositions or treatments of the present invention can further comprise one or more Cholesteryl Ester Transfer Protein ("CETP") Inhibitors coadministered with or in combination with compound of Formula (I) discussed above. CETP is responsible for the exchange or transfer of cholesteryl ester carrying HDL and triglycerides in VLDL. Non-limiting examples of suitable CETP inhibitors are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be coadministered with or in combination with the compound of Formula (I) discussed above. Generally, a total daily dosage of CETP inhibitor(s) can range from about 0.01 to about 1000 mg/day, and preferably about 0.5 to about 20 mg/kg body weight/day in single or divided doses.

In another alternative embodiment, the compositions or treatments of the present invention can further comprise probucol or derivatives thereof (such as AGI-1067 and other derivatives disclosed in U.S. Pat. Nos. 6,121,319 and 6,147,250), which can reduce LDL levels, coadministered with or in combination with the compound of Formula (I) discussed above. Generally, a total daily dosage of probucol or derivatives thereof can range from about 10 to about 2000 mg/day, and preferably about 500 to about 1500 mg/day in single or 2-4 divided doses.

In another alternative embodiment, the compositions or treatments of the present invention can further comprise low-density lipoprotein (LDL) receptor activators, coadministered with or in combination with the compound of Formula (I) discussed above. Non-limiting examples of suitable LDL-receptor activators include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", Arterioscler. Thromb. 1993; 13:1005-12. Generally, a total daily dosage of LDL receptor activator(s) can range from about 1 to about 1000 mg/day in single or 2-4 divided doses.

In another alternative embodiment, the compositions or treatments of the present invention can further comprise fish oil, which contains Omega 3 fatty acids (3-PUFA), which can reduce VLDL and triglyceride levels, coadministered with or in combination with the compound of Formula (I) discussed above. Generally, a total daily dosage of fish oil or Omega 3 fatty acids can range from about 1 to about 30 grams per day in single or 2-4 divided doses.

In another alternative embodiment, the compositions or treatments of the present invention can further comprise natural water soluble fibers, such as psyllium, guar, oat and pectin, which can reduce cholesterol levels, coadministered with or in combination with the compound of Formula (I) discussed above. Generally, a total daily dosage of natural water soluble fibers can range from about 0.1 to about 10 grams per day in single or 2-4 divided doses.

In another alternative embodiment, the compositions or treatments of the present invention can further comprise plant sterols, plant stanols and/or fatty acid esters of plant stanols, such as sitostanol ester used in BENECOL® margarine, which can reduce cholesterol levels, coadministered with or in combination with the compound of Formula (I) discussed above. Generally, a total daily dosage of plant sterols, plant stanols and/or fatty acid esters of plant stanols can range from about 0.5 to about 20 grams per day in single or 2-4 divided doses.

In another alternative embodiment, the compositions or treatments of the present invention can further comprise antioxidants, such as probucol, tocopherol, ascorbic acid, β-carotene and selenium, or vitamins such as vitamin $B_6$ or vitamin $B_{12}$, coadministered with or in combination with the compound of Formula (I) discussed above. Generally, a total daily dosage of antioxidants or vitamins can range from about 0.05 to about 10 grams per day in single or 2-4 divided doses.

In another alternative embodiment, the compositions or treatments of the present invention can further comprise monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E, coadministered with or in combination with the compound of Formula (I) discussed above. Generally, a total daily dosage of these agents can range from about 0.01 to about 1000 mg/day in single or 2-4 divided doses.

Also useful with the present invention are compositions or therapeutic combinations that further comprise hormone replacement agents and compositions. Useful hormone agents and compositions for hormone replacement therapy of the present invention include androgens, estrogens, progestins, their pharmaceutically acceptable salts and derivatives thereof. Combinations of these agents and compositions are also useful. The dosage of androgen and estrogen combinations vary, desirably from about 1 mg to about 4 mg androgen and from about 1 mg to about 3 mg estrogen.

The compositions, therapeutic combinations or methods of the present invention can further comprise one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxtine); thermogenic agents (such as ephedrine, caffeine, theophylline, and selective β3-adrenergic agonists); alpha-blocking agents; kainite or AMPA receptor antagonists; leptin-lipolysis stimulated receptors; phosphodiesterase enzyme inhibitors; compounds having nucleotide sequences of the mahogany gene; fibroblast growth factor-10 polypeptides; monoamine oxidase inhibitors (such as befloxatone, moclobemide, brofaromine, phenoxathine, esuprone, befol, toloxatone, pirlindol, amiflamine, sercloremine, bazinaprine, lazabemide, milacemide and caroxazone); compounds for increasing lipid metabolism (such as evodiamine compounds); and lipase inhibitors (such as orlistat). Generally, a total dosage of the above-described obesity control medications can range from 1 to 3,000 mg/day, desirably from about 1 to 1,000 mg/day and more desirably from about 1 to 200 mg/day in single or 2-4 divided doses.

The compositions, therapeutic combinations or methods of the present invention can further comprise one or more blood modifiers which are chemically different from the compounds of Formula (I) discussed above, for example, they contain one or more different atoms, have a different arrangement of atoms or a different number of one or more atoms than the compounds of Formula (I) discussed above. Useful blood modifiers include but are not limited to anticoagulants (argatroban, bivalirudin, dalteparin sodium, desirudin, dicumarol, lyapolate sodium, nafamostat mesylate, phenprocoumon, tinzaparin sodium, warfarin sodium); antithrombotic (anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab, zolimomab aritox); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate, epoprostenol, epoprostenol sodium, ticlopidine hydrochloride, aspirin, ibuprofen, naproxen, sulindae, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitors; Factor VIIa inhibitors (4H-31-benzoxazin-4-ones, 4H-3,1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl}amide trifluoroacetate, dibenzofuran-2-sulfonic acid {1-[3-(aminomethyl)-benzyl]-5-oxo-pyrrolidin-3-yl}-amide, tolulene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate); Factor Xa inhibitors (disubstituted pyrazolines, disubstituted triazolines, substituted n-[(aminoiminomethyl)phenyl]propylamides, substituted n-[(aminomethyl)phenyl]propylamides, tissue factor pathway inhibitor (TFPI), low molecular weight heparins, heparinoids, benzimidazolines, benzoxazolinones, benzopiperazinones, indanones, dibasic (amid inoaryl) propanoic acid derivatives, amid inophenyl-pyrrolidines, amidinophenyl-pyrrolines, amidinophenyl-isoxazolidines, amidinoindoles, amidinoazoles, bis-arlysulfonylaminobenzamide derivatives, peptidic Factor Xa inhibitors).

The compositions, therapeutic combinations or methods of the present invention can further comprise one or more cardiovascular agents which are chemically different from the compounds of Formula (I) discussed above, for example, they contain one or more different atoms, have a different arrangement of atoms or a different number of one or more atoms than the compounds of Formula (I) discussed above. Useful cardiovascular agents include but are not limited to calcium channel blockers (clentiazem maleate, amlodipine besylate, isradipine, nimodipine, felodipine, nilvadipine, nifedipine, teludipine hydrochloride, diltiazem hydrochloride, belfosdil, verapamil hydrochloride, fostedil); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate, nebivolol); adrenergic stimulants; angiotensin converting enzyme (ACE) inhibitors (benazepril hydrochloride, benazeprilat, captopril, delapril hydrochloride, fosinopril sodium, libenzapril, moexipril hydrochloride, pentopril, perindopril, quinapril hydrochloride, quinaprilat, ramipril, spirapril hydrochloride, spiraprilat, teprotide, enalapril maleate, lisinopril, zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate, bevantolol hydrochloride), for example HYZAAR® or COZAAR® antihypertensive agents available from Merck & Co., Inc.; angiotensin II receptor antagonists (candesartan, irbesartan, losartan potassium, candesartan cilexetil, telmisartan); anti-anginal agents (amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochoride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexiline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the present invention can further comprise one or more antidiabetic medications for reducing blood glucose levels in a human. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguanide (such as mefformin and buformin), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 2-4 divided doses.

The compositions, therapeutic combinations or methods of the present invention can further comprise one or more treatments for Alzheimer's Disease which are chemically different from the compounds of Formula (I). Non-limiting examples of suitable treatments which can be useful in treating Alzheimer's Disease include administration of one or more of the following: cholinesterase inhibitors, muscarinic receptor agonists, M2 muscarinic receptor antagonists, acetylcholine release stimulators, choline uptake stimulators, nicotinic cholinergic receptor agonists, anti-Aβ vaccines, γ-secretase inhibitors, β-secretase inhibitors, amyloid aggregation inhibitors, amyloid precursor protein antisense oligonucleotides, monoamine reuptake inhibitors, human stem cells, gene therapy, nootropic agents, AMPA receptor ligands, growth factors or growth factor receptor agonists, anti-inflammatory agents, free radical scavengers, antioxidants, superoxide dismutase stimulators, calcium channel blockers, apoptosis inhibitors, caspase inhibitors, monoamine oxidase inhibitors, estrogens and estrogen receptor ligands, NMDA receptor antagonists, Jun N-terminal kinase (JNK) inhibitors, copper/zinc chelators, 5-HT1a receptor agonists, NGF stimulators, neuroprotective agents, H3 histamine receptor antagonists, calpain inhibitors, poly ADP ribose polymerase inhibitors, prolylendopeptidase inhibitors, calcium modulators, corticortropin releasing factor receptor antagonists, corticortropin releasing factor binding protein inhibitors, GABA modulators, GABA-A receptor antagonists, GABA-B receptor antagonists, neuroimmunophilin ligands, sigma receptor ligands, galanin receptor ligands, imidazoline/alpha adrenergic receptor antagonists, vasoactive intestinal peptide receptor agonists, benzodiazepine receptor inverse agonists, cannabinoid receptor agonists, thyrotropin releasing hormone receptor agonists, protein kinase C inhibitors, 5-HT3 receptor antagonists, prostaglandin receptor antagonists, topoisomerase II inhibitors, steroid receptor ligand, nitric oxide modulators, RAGE inhibitors, dopamine receptor agonists, and combinations thereof.

Mixtures of any of the pharmacological or therapeutic agents described above can be used in the compositions and therapeutic combinations of the present invention.

The pharmaceutical treatment compositions (formulations or medicaments) and therapeutic combinations of the present invention can further comprise one or more pharmaceutically acceptable carriers, one or more excipients and/or one or more additives. As used herein, the term "composition" is intended to encompass a product comprising the specified ingredients in the specified amounts, as well as any product which results, directly or indirectly, from combination of the specified ingredients in the specified amounts.

Non-limiting examples of pharmaceutically acceptable carriers include solids and/or liquids such as ethanol, glycerol, water and the like. The amount of carrier in the treatment composition can range from about 5 to about 99 weight percent of the total weight of the treatment composition or therapeutic combination. Non-limiting examples of suitable pharmaceutically acceptable excipients and additives include non-toxic compatible fillers, binders such as starch, disintegrants, buffers, preservatives, anti-oxidants, lubricants, flavorings, thickeners, coloring agents, emulsifiers and the like. The amount of excipient or additive can range from about 0.1 to about 90 weight percent of the total weight of the treatment composition or therapeutic combination. One skilled in the art would understand that the amount of carrier(s), excipients and additives (if present) can vary.

The treatment compositions of the present invention can be administered in any conventional dosage form, preferably an oral dosage form such as a capsule, tablet, powder, cachet, suspension or solution. The formulations and pharmaceutical compositions can be prepared using conventional pharmaceutically acceptable and conventional techniques. Several examples of preparation of dosage formulations are provided below.

The following formulation exemplifies a dosage form of this invention. In the formulation, the term "Active Compound I" designates a compound of Formula I described herein above.

EXAMPLE

| No. | Ingredient | mg/tablet |
|---|---|---|
| | Tablets | |
| 1 | Active Compound I | 20 |
| 2 | Lactose monohydrate NF | 55 |
| 3 | Microcrystalline cellulose NF | 20 |
| 4 | Povidone (K29-32) USP | 4 |
| 5 | Croscarmellose sodium NF | 8 |
| 6 | Sodium lauryl sulfate | 2 |
| 7 | Magnesium stearate NF | 1 |
| | Total | 110 |

Method of Manufacture

Mix Item No. 4 with purified water in suitable mixer to form binder solution. Spray the binder solution and then water over Items 1, 2, 6 and a portion of Item 5 in a fluidized bed processor to granulate the ingredients. Continue fluidization to dry the damp granules. Screen the dried granules and blend with Item No. 3 and the remainder of Item 5. Add Item No. 7 and mix. Compress the mixture to appropriate size and weight on a suitable tablet machine.

Since the present invention relates to treating conditions as discussed above, such as reducing the plasma sterol (especially cholesterol) concentrations or levels by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one compound of Formula (I) and a separate pharmaceutical composition comprising at least one other therapeutic agent as described above. The kit will preferably include directions for the administration of the separate components. The kit form is particularly advantageous when the separate components must be administered in different dosage forms (e.g., oral and parenteral) or are administered at different dosage intervals.

The treatment compositions and therapeutic combinations of the present invention can inhibit the intestinal absorption of cholesterol in mammals, as shown in the Example below, and can be useful in the treatment and/or prevention of conditions, for example vascular conditions, such as atherosclerosis, hypercholesterolemia and sitosterolemia, stroke, obesity and lowering of plasma levels of cholesterol in mammals, in particular in mammals.

In another embodiment of the present invention, the compositions and therapeutic combinations of the present invention can inhibit sterol absorption or reduce plasma concentration of at least one sterol selected from the group consisting of phytosterols (such as sitosterol, campesterol, stigmasterol and avenosterol), 5α-stanols (such as cholestanol, 5α-campestanol, 5α-sitostanol), cholesterol and mixtures thereof. The plasma concentration can be reduced by administering to a mammal in need of such treatment an effective amount of at least one treatment composition or therapeutic combination comprising a compound of Formula (I) described above. The reduction in plasma concentration of sterols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593-600 (1999), incorporated by reference herein.

Illustrating the invention are the following examples which, however, are not to be considered as limiting the invention to their details. Unless otherwise indicated, all parts and percentages in the following examples, as well as throughout the specification, are by weight.

EXAMPLE

Hypothetical In Vivo Evaluation

The hypercholesterolemic Golden Syrian hamster can be used as the in vivo model to evaluate the oral potency and in vivo efficacy of cholesterol absorption inhibitors. Hamsters would be fed a cholesterol-containing diet for 7 days, which results in an increase in hepatic cholesteryl esters. A compound which blocks intestinal cholesterol absorption would reduce the accumulation of hepatic cholesteryl ester levels.

Male Golden Syrian hamsters (Charles River Labs, Wilmington, Mass.) would be fed Wayne rodent chow until study onset. At study onset (Day 1) animals would be separated into groups (n=4-6/group) and fed chow supplemented with 0.5% by weight of cholesterol (Research Diets Inc., New Brunswick, N.J.). One group of hamsters would receive a dosage of 3 mg/kg of body weight of any one of the compounds of Formulae (II), (III), (IV) or (V) administered once daily for 7 days, starting on Day 1 via oral gavage in 0.2 ml corn oil. The control group of hamsters would receive placebo corn oil in the same amount on the same schedule. On Day 7 liver samples would be taken for neutral lipid analyses. Samples of liver would be lipid extracted. Lipid extracts would be dried under nitrogen into HPLC sample vials, resuspended in hexane and injected onto a Zorbax Sil (4.6×25 cm) silica column. Chromatography would be performed using an isocratic mobile phase containing 98.8% hexane and 1.2% isopropanol at a flow rate of 2 ml/min. Lipids can be detected by absorbance at 206 nm and quantitated by computer integration (System Gold, Beckman) of elution profiles. Cholesterol concentrations can be determined by the use of a response factor derived from a standard curve using known amounts of cholesterol. Cholesteryl ester content of liver-derived samples can be derived from a standard curve constructed using known amounts of cholesteryl oleate. Cholesteryl oleate can be used as the standard since this is the major cholesteryl ester species present in the liver and this specific cholesteryl ester has an extinction coefficient that approximates that of a weighted average for all the cholesteryl esters present in the liver.

The reduction of hepatic cholesteryl ester accumulation is utilized as a marker for cholesterol absorption inhibition.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Therefore, we claim:

1. A compound represented by the structural formula (I):

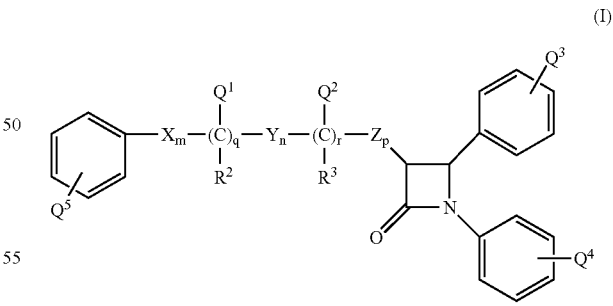

(I)

or pharmaceutically acceptable isomers, salts, solvates or esters of the compound of Formula (I), wherein in Formula (I) above:

X, Y and Z can be the same or different and each is independently selected from the group consisting of $-CH_2-$, $-CH(alkyl)-$ and $-C(alkyl)_2-$;

$Q^1$ and $Q^2$ can be the same or different and each is independently selected from the group consisting of H, -G, $-(C_1-C_{30}$ alkylene)-G, $-OR^6$, $-OC(O)R^6$, $-OC(O)OR^9$, $-OC(O)NR^6R^7$, and -L-M;

Q³ is 1 to 5 substituents independently selected from the group consisting of alkyl, alkenyl, alkynyl, -G, —(C$_1$-C$_{30}$ alkylene)-G, —OR$^6$, —(C$_1$-C$_{10}$ alkylene)-OR$^6$, —C(O)R$^6$, —(C$_1$-C$_{10}$ alkylene)-C(O)R$^6$, —C(O)OR$^6$, —(C$_1$-C$_{10}$ alkylene)-C(O)OR$^6$, —OC(O)R$^6$, —(C$_1$-C$_{10}$ alkylene)-OC(O)R$^6$, —OC(O)OR$^9$, —(C$_1$-C$_{10}$ alkylene)-OC(O)OR$^9$, —CH=CH—C(O)R$^6$, —CH=CH—C(O)OR$^6$,

—C≡C—C(O)OR$^6$, —C≡C—C(O)R$^6$,

—O—(C$_1$-C$_{10}$ alkylene)-OR$^6$, —O—(C$_1$-C$_{10}$ alkylene)-C(O)R$^6$, —O—(C$_1$-C$_{10}$ alkylene)-C(O)OR$^6$, —CN, —O—(C$_1$-C$_{10}$ alkylene)-C(O)NR$^6$R$^7$, —O—C(O)NR$^6$NR$^7$C(O)OR$^6$, —O—(C$_1$-C$_{10}$ alkylene)-C(O)NR$^6$NR$^7$C(O)OR$^6$, —O—(C$_1$-C$_{10}$ alkylene)-C(O)(aryl)-N$_3$, —OC(O)—(C$_1$-C$_{10}$ alkylene)-C(O)OR$^6$, —C(O)NR$^6$R$^7$, —(C$_1$-C$_{10}$ alkylene)-C(O)NR$^6$R$^7$, —OC(O)NR$^6$R$^7$, —(C$_1$-C$_{10}$ alkylene)-OC(O)NR$^6$R$^7$, —NO$_2$, —NR$^6$R$^7$, —(C$_1$-C$_{10}$ alkylene)-NR$^6$R$^7$, —O—(C$_2$-C$_{10}$ alkylene)-NR$^6$R$^7$, —NR$^6$C(O)R$^7$, —NR$^6$C(O)OR$^9$, —NR$^6$C(O)NR$^7$R$^8$, —NR$^6$S(O)$_{0-2}$R$^9$, —N(S(O)$_{0-2}$R$^9$)$_2$, —CHNOR$^6$, —C(O)NR$^6$R$^7$, —C(O)NR$^6$NR$^6$R$^7$, —S(O)$_{0-2}$NR$^6$R$^7$, —S(O)$_{0-2}$R$^9$, —O—C(O)—(C$_1$-C$_{10}$ alkylene)-C(O)NR$^6$R$^7$, —OC(O)—(C$_1$-C$_{10}$ alkylene)-NR$^6$C(O)O-(alkylaryl), —P(O)(OR$^{10}$)$_2$, —(C$_1$-C$_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

Q⁴ is 1 to 5 substituents independently selected from the group consisting of alkyl, alkenyl, alkynyl, -G, —(C$_1$-C$_{30}$ alkylene)-G, —OR$^6$, —(C$_1$-C$_{10}$ alkylene)-OR$^6$, —C(O)R$^6$, —(C$_1$-C$_{10}$ alkylene)-C(O)R$^6$, —C(O)OR$^6$, —(C$_1$-C$_{10}$ alkylene)-C(O)OR$^6$, —OC(O)R$^6$, —(C$_1$-C$_{10}$ alkylene)-OC(O)R$^6$, —OC(O)OR$^9$, —(C$_1$-C$_{10}$ alkylene)-OC(O)OR$^9$, —CH=CH—C(O)R$^6$, —CH=CH—C(O)OR$^6$,

—C≡C—C(O)OR$^6$, —C≡C—C(O)R$^6$,

—O—(C$_1$-C$_{10}$ alkylene)-OR$^6$, —O—(C$_1$-C$_{10}$ alkylene)-C(O)R$^6$, —O—(C$_1$-C$_{10}$ alkylene)-C(O)OR$^6$, —CN, —O—(C$_1$-C$_{10}$ alkylene)-C(O)NR$^6$R$^7$, —O—C(O)NR$^6$NR$^7$C(O)OR$^6$, —O—(C$_1$-C$_{10}$ alkylene)-C(O)NR$^6$NR$^7$C(O)OR$^6$, —O—(C$_1$-C$_{10}$ alkylene)-C(O)(aryl)-N$_3$, —OC(O)—(C$_1$-C$_{10}$ alkylene)-C(O)OR$^6$, —C(O)NR$^6$R$^7$, —(C$_1$-C$_{10}$ alkylene)-C(O)NR$^6$R$^7$, —OC(O)NR$^6$R$^7$, —(C$_1$-C$_{10}$ alkylene)-OC(O)NR$^6$R$^7$, —NO$_2$, —NR$^6$R$^7$, —(C$_1$-C$_{10}$ alkylene)-NR$^6$R$^7$, —O—(C$_2$-C$_{10}$ alkylene)-NR$^6$R$^7$, —NR$^6$C(O)R$^7$, —NR$^6$C(O)OR$^9$, —NR$^6$C(O)NR$^7$R$^8$, —NR$^6$S(O)$_{0-2}$R$^9$, —N(S(O)$_{0-2}$R$^9$)$_2$, —CHNOR$^6$, —C(O)NR$^6$R$^7$, —C(O)NR$^6$NR$^6$R$^7$, —S(O)$_{0-2}$NR$^6$R$^7$, —S(O)$_{0-2}$R$^9$, —O—C(O)—(C$_1$-C$_{10}$ alkylene)-C(O)NR$^6$R$^7$, —OC(O)—(C$_1$-C$_{10}$ alkylene)-NR$^6$C(O)O-(alkylaryl), —P(O)(OR$^{10}$)$_2$, —(C$_1$-C$_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

Q⁵ is 1 to 5 substituents independently selected from the group consisting of alkyl, alkenyl, alkynyl, -G, —(C$_1$-C$_{30}$ alkylene)-G, —OR$^6$, —(C$_1$-C$_{10}$ alkylene)-OR$^6$, —C(O)R$^6$, —(C$_1$-C$_{10}$ alkylene)-C(O)R$^6$, —C(O)OR$^6$, —(C$_1$-C$_{10}$ alkylene)-C(O)OR$^6$, —OC(O)R$^6$, —(C$_1$-C$_{10}$ alkylene)-OC(O)R$^6$, —OC(O)OR$^9$, —(C$_1$-C$_{10}$ alkylene)-OC(O)OR$^9$, —CH=CH—C(O)R$^6$, —CH=CH—C(O)OR$^6$,

—C≡C—C(O)OR$^6$, —C≡C—C(O)R$^6$,

—O—(C$_1$-C$_{10}$ alkylene)-OR$^6$, —O—(C$_1$-C$_{10}$ alkylene)-C(O)R$^6$, —O—(C$_1$-C$_{10}$ alkylene)-C(O)OR$^6$, —CN, —O—(C$_1$-C$_{10}$ alkylene)-C(O)NR$^6$R$^7$, —O—C(O)NR$^6$NR$^7$C(O)OR$^6$, —O—(C$_1$-C$_{10}$ alkylene)-C(O)NR$^6$NR$^7$C(O)OR$^6$, —O—(C$_1$-C$_{10}$ alkylene)-C(O)(aryl)-N$_3$, —OC(O)—(C$_1$-C$_{10}$ alkylene)-C(O)OR$^6$, —C(O)NR$^6$R$^7$, —(C$_1$-C$_{10}$ alkylene)-C(O)NR$^6$R$^7$, —OC(O)NR$^6$R$^7$, —(C$_1$-C$_{10}$ alkylene)-OC(O)NR$^6$R$^7$, —NO$_2$, —NR$^6$R$^7$, —(C$_1$-C$_{10}$ alkylene)-NR$^6$R$^7$, —O—(C$_2$-C$_{10}$ alkylene)-NR$^6$R$^7$, —NR$^6$C(O)R$^7$, —NR$^6$C(O)OR$^9$, —NR$^6$C(O)NR$^7$R$^8$, —NR$^6$S(O)$_{0-2}$R$^9$, —N(S(O)$_{0-2}$R$^9$)$_2$, —CHNOR$^6$, —C(O)NR$^6$R$^7$, —C(O)NR$^6$NR$^6$R$^7$, —S(O)$_{0-2}$NR$^6$R$^7$, —S(O)$_{0-2}$R$^9$, —O—C(O)—(C$_1$-C$_{10}$ alkylene)-C(O)NR$^6$R$^7$, —OC(O)—(C$_1$-C$_{10}$ alkylene)-NR$^6$C(O)O-(alkylaryl), —P(O)(OR$^{10}$)$_2$, —(C$_1$-C$_{10}$ alkylene)-OSi(alkyl)$_3$, —CF$_3$, —OCF$_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

wherein optionally one or more carbon atoms of the —(C$_1$-C$_{30}$ alkylene)- radical of Q¹, Q², Q³, Q⁴ and Q⁵ is independently replaced by —O—, —C(O)—, —CH=CH—, —C≡C—, —N(alkyl)-, —N(alkylaryl)- or —NH—;

G is selected from the group consisting of a sugar residue, disugar residue, trisugar residue, tetrasugar residue, sugar acid, and amino sugar, wherein optionally the sugar residue, disugar residue, trisugar residue, tetrasugar residue, sugar acid, or amino sugar of G is substituted with -L-M;

L is selected from the group consisting of

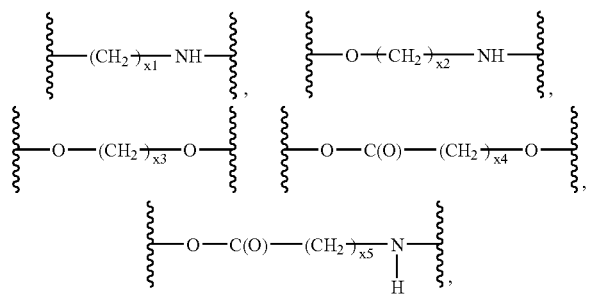

-continued
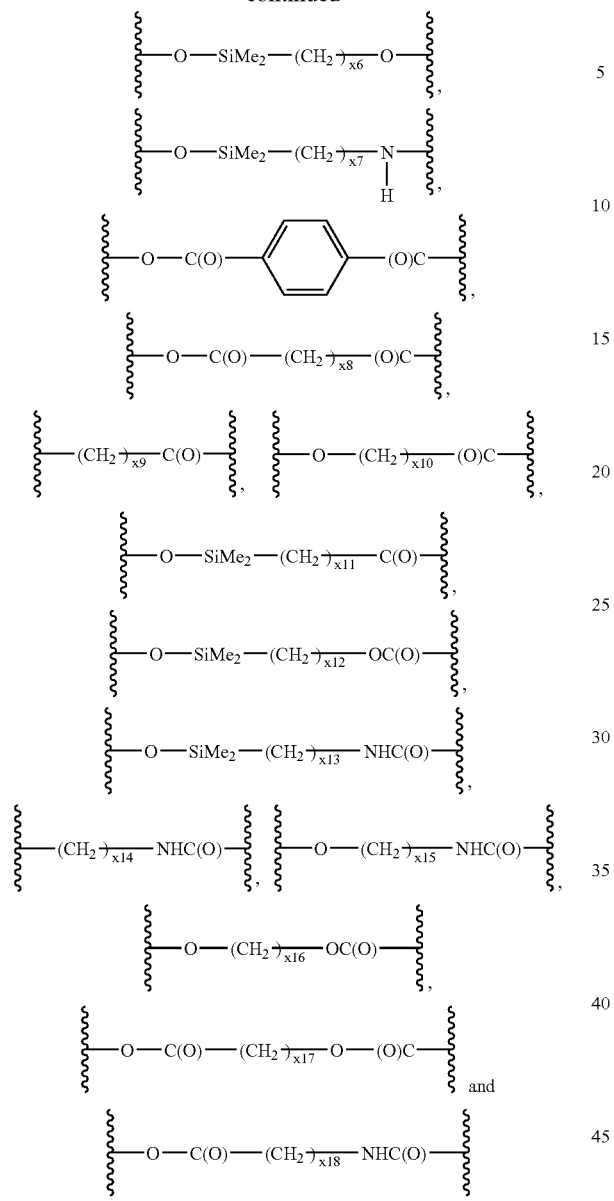
wherein Me is methyl;
M is selected from the group of moieties consisting of
-continued
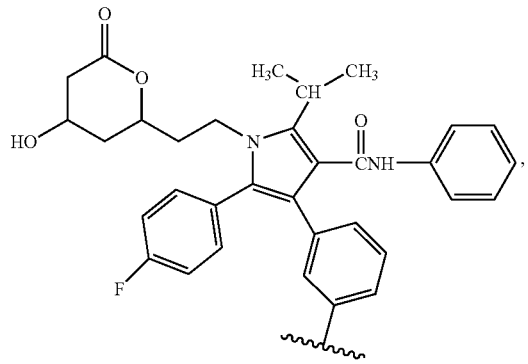
(M3)
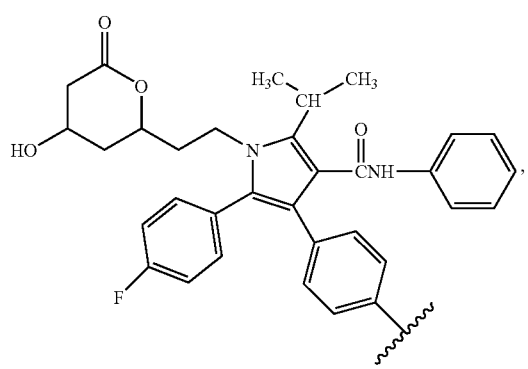
(M4)
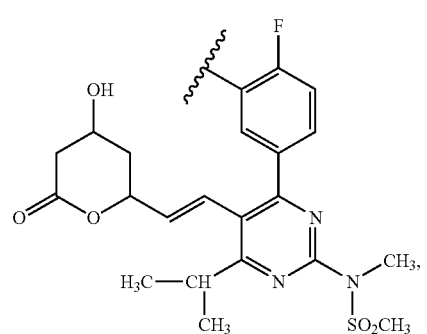
(M5)
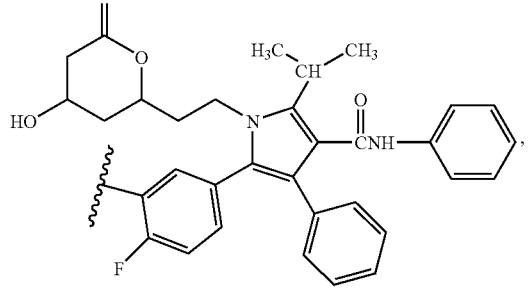
(M1)
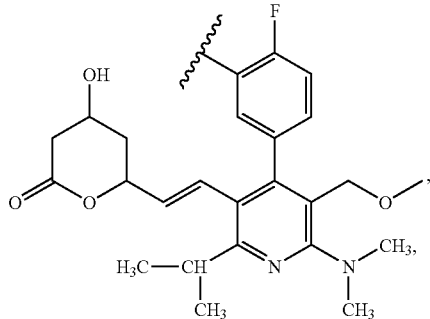
(M6)

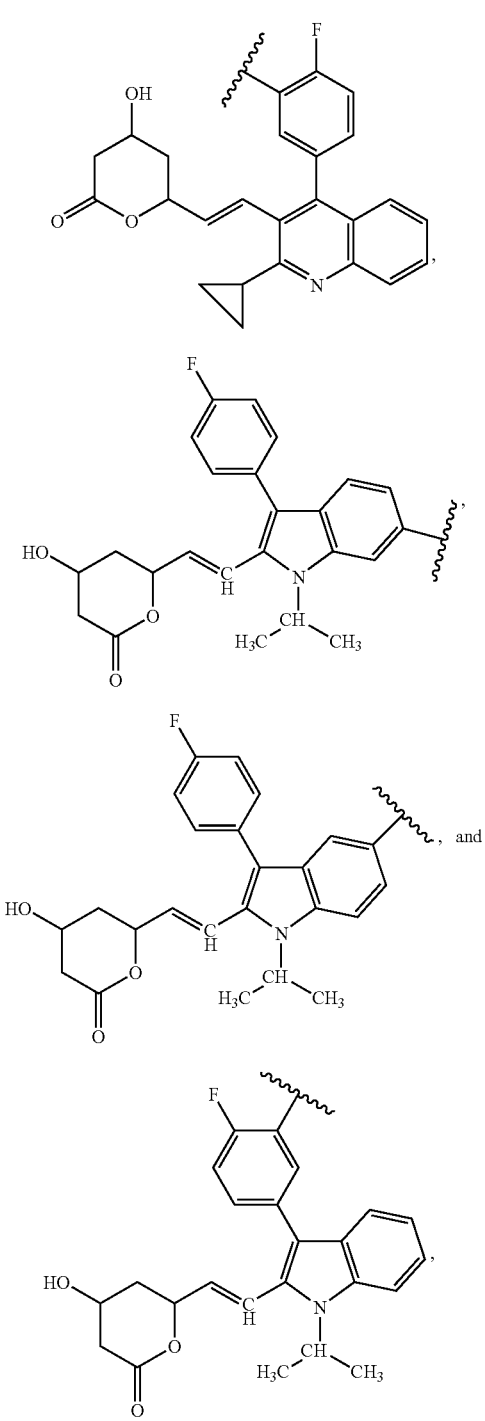

pharmaceutically acceptable salts of the moieties (M1) and (M3) to (M10) and free acids of the moieties (M1) and (M3) to (M10);

R$^2$ and R$^3$ can be the same or different and each is independently selected from the group consisting of hydrogen, alkyl and aryl;

R$^6$, R$^7$ and R$^8$ can be the same or different and each is independently selected from the group consisting of hydrogen, alkyl, aryl and arylalkyl; and each R$^9$ is independently alkyl, aryl or arylalkyl, each R$^{10}$ is independently H or alkyl;

q is 0 or 1;

r is 0 or 1;

m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

x1 is 1 to 10;
x2 is 1 to 10;
x3 is 1 to 10;
x4 is 1 to 10;
x5 is 1 to 10;
x6 is 1 to 10; and
x7 is 1 to 10;
x8 is 1 to 10;
x9 is 1 to 10;
x10 is 1 to 10;
x11 is 1 to 10;
x12 is 1 to 10;
x13 is 1 to 10;
x14 is 1 to 10;
x15 is 1 to 10; and
x16 is 1 to 10;
x17 is 1 to 10; and
x18 is 1 to 10;

with the proviso that at least one of Q$^1$, Q$^2$, Q$^3$, Q$^4$ and Q$^5$ is the sugar residue, disugar residue, trisugar residue, tetrasugar residue, sugar acid, or amino sugar of G is substituted with -L-M, and wherein each of the above alkyl, alkenyl, alkynyl, alkylene, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, or heterocyclylcarbonylalkoxy groups, when present, is independently substituted or unsubstituted.

2. The compound according to claim 1, wherein m, n and r are each zero, q is 1, p is 2, and Z is —CH$_2$—.

3. The compound according to claim 1, wherein m, n and r are each zero, q is 1, p is 2, and Z is —CH$_2$—, Q$^1$ is —OR$^6$, wherein R$^6$ is hydrogen and Q$^5$ is fluorine.

4. The compound according to claim 1, wherein R$^2$ and R$^3$ are each hydrogen.

5. The compound according to claim 1, wherein Q$^1$ and Q$^2$ are each independently selected from the group consisting of —OR$^6$, —O(CO)R$^6$, —O(CO)OR$^9$ and —O(CO)NR$^6$R$^7$.

6. The compound according to claim 1, wherein Q$^4$ is halo or —OR$^6$.

7. The compound according to claim 1, wherein Q$^1$ is —OR$^6$ wherein R$^6$ is H.

8. The compound according to claim 1, wherein Q$^1$, Q$^2$, Q$^3$, Q$^4$ or Q$^5$ is -L-M.

9. The compound according to claim 1, wherein Q$^1$, Q$^2$, Q$^3$, Q$^4$ or Q$^5$ is -G or —(C$_1$-C$_{30}$ alkylene)-G.

10. The compound according to claim 1, wherein G is selected from the group consisting of:

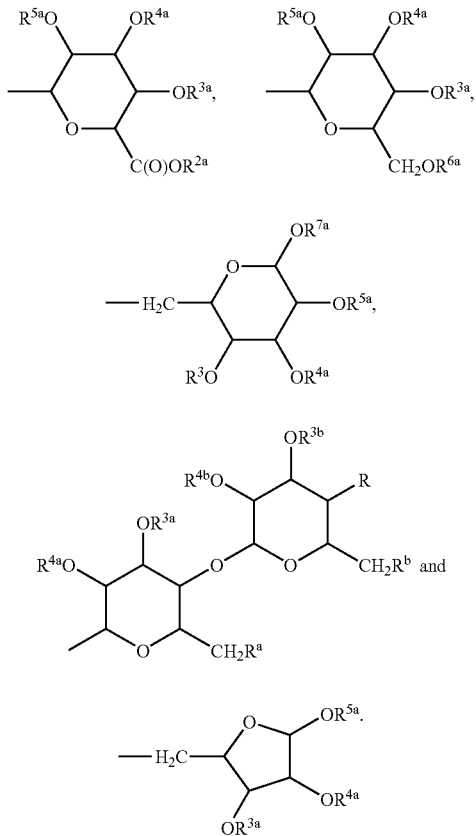

wherein R, $R^a$ and $R^b$ can be the same or different and each is independently selected from the group consisting of H, —OH, halo, —$NH_2$, azido, alkoxyalkoxy or -W-$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^{2a}$ and $R^{6a}$ can be the same or different and each is independently selected from the group consisting of H, alkyl, acetyl, aryl and arylalkyl;

$R^{3a}$, $R^{4a}$, $R^{5a}$, $R^{7a}$, $R^{3b}$ and $R^{4b}$ can be the same or different and each is independently selected from the group consisting of H, alkyl, acetyl, arylalkyl, —C(O)alkyl and —C(O)aryl;

$R^{30}$ is independently selected from the group consisting of $R^{32}$-substituted T, $R^{32}$-substituted-T-alkyl, $R^{32}$-substituted-alkenyl, $R^{32}$-substituted-alkyl, $R^{32}$-substituted-cycloalkyl and $R^{32}$-substituted-cycloalkylalkyl;

$R^{31}$ is independently selected from the group consisting of H and alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is 1 to 3 substituents which are each independently selected from the group consisting of H, halo, alkyl, —OH, phenoxy, —$CF_3$, —$NO_2$, alkoxy, methylenedioxy, oxo, alkylsulfanyl, alkylsulfinyl, alkylsulfonyl, —N($CH_3$)$_2$, —C(O)—NHalkyl, —C(O)—N(alkyl)$_2$, —C(O)-alkyl, —C(O)-alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a alkoxycarbonyl-substituted pyrrolidinyl, piperidinyl, N-methylpiperazinyl, indolinyl or morpholinyl group.

11. The compound according to claim 10, wherein G is selected from:

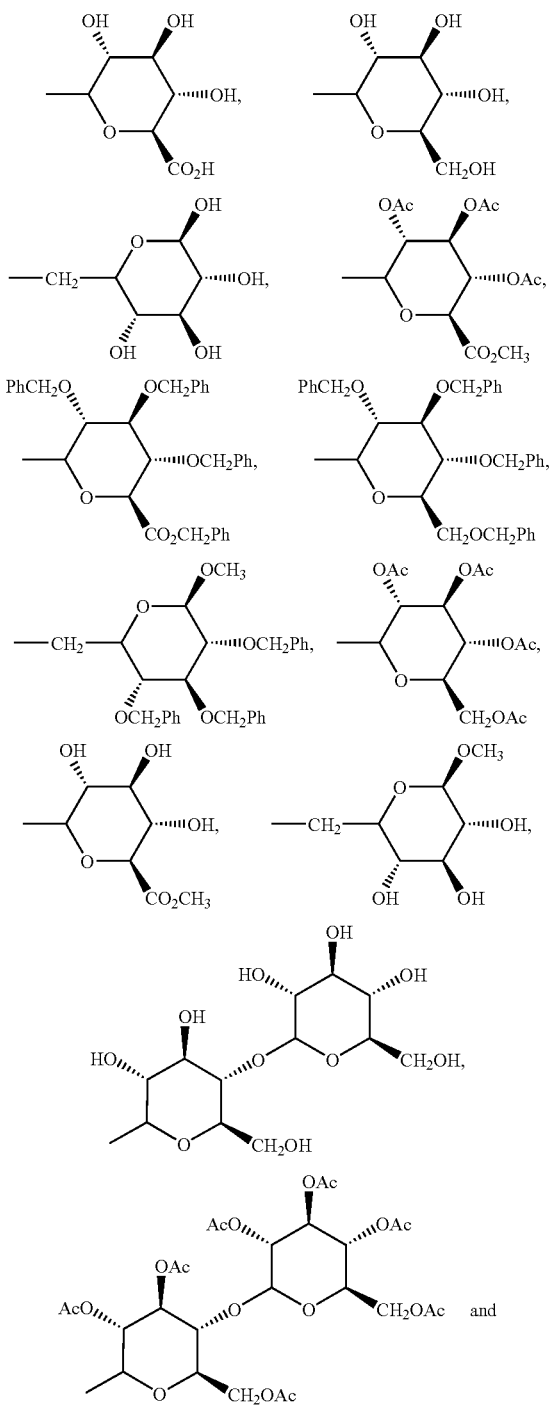

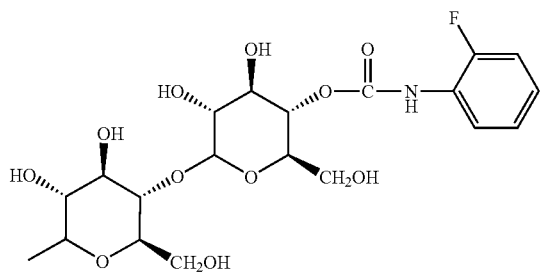

wherein Ac is acetyl and Ph is phenyl.

12. The compound according to claim 1, wherein optionally one or more carbon atoms of the —($C_1$-$C_{30}$ alkylene)- radical of $Q^1$, $Q^2$, $Q^3$, $Q^4$ and $Q^5$ is independently replaced by —O—.

13. A pharmaceutical composition for the treatment of atherosclerosis, hypercholesterolemia, sitosterolemia, lowering a concentration of cholesterol, phytosterol or 5α-stanol in plasma of a subject comprising a therapeutically effective amount of a compound of claim 1 in a pharmaceutically acceptable carrier.

14. A pharmaceutical composition comprising a cholesterol-lowering effective amount of a compound of claim 1 in a pharmaceutically acceptable carrier.

15. A method of treating atherosclerosis, hypercholesterolemia, sitosterolemia, lowering a concentration of cholesterol, phytosterol or 5α-stanol in plasma of a subject comprising the step of administering to a subject in need of such treatment an effective amount of a compound of claim 1.

16. A method of lowering cholesterol level in plasma of a mammal in need of such treatment comprising administering a pharmaceutically effective amount of the compound of claim 1.

17. A compound represented by the structural formula (IA):

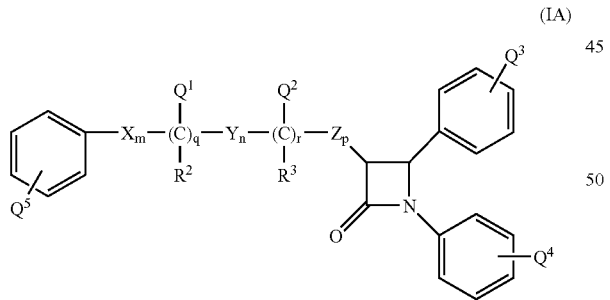

or pharmaceutically acceptable isomers, salts, solvates or esters of the compound of Formula (IA),
wherein in Formula (IA) above:
X, Y and Z can be the same or different and each is independently selected from the group consisting of —$CH_2$—, —CH(alkyl)- and —C(alkyl)$_2$-;
$Q^1$ and $Q^2$ can be the same or different and each is independently selected from the group consisting of H, -G, —($C_1$-$C_{30}$ alkylene)-G, —$OR^6$, —$OC(O)R^6$, —$OC(O)OR^9$, —$OC(O)NR^6R^7$, and -L-M;

$Q^3$ is 1 to 5 substituents independently selected from the group consisting of alkyl, alkenyl, alkynyl, -G, —($C_1$-$C_{30}$ alkylene)-G, —$OR^6$, —($C_1$-$C_{10}$ alkylene)-$OR^6$, —$C(O)R^6$, —($C_1$-$C_{10}$ alkylene)-$C(O)R^6$, —$C(O)OR^6$, —($C_1$-$C_{10}$ alkylene)-C(O)$OR^6$, —$OC(O)R^6$, —($C_1$-$C_{10}$ alkylene)-$OC(O)R^6$, —$OC(O)R^9$, —($C_1$-$C_{10}$ alkylene)-OC(O)$OR^9$, —CH=CH—$C(O)R^6$, —CH=CH—C(O)$OR^6$,

—C≡C—C(O)$OR^6$, —C≡C—$C(O)R^6$,

—O—($C_1$-$C_{10}$ alkylene)-$OR^6$, —O—($C_1$-$C_{10}$ alkylene)-$C(O)R^6$, —O—($C_1$-$C_{10}$ alkylene)-C(O)$OR^6$, —CN, —O—($C_1$-$C_{10}$ alkylene)-$C(O)NR^6R^7$, —O—C(O)$NR^6NR^7C(O)OR^6$, —O—($C_1$-$C_{10}$ alkylene)-C(O) $NR^6NR^7C(O)OR^6$, —O—($C_1$-$C_{10}$ alkylene)-C(O)(aryl)-$N_3$, —OC(O)—($C_1$-$C_{10}$ alkylene)-C(O)$OR^6$, —$C(O)NR^6R^7$, —($C_1$-$C_{10}$ alkylene)-$C(O)NR^6R^7$, —$OC(O)NR^6R^7$, —($C_1$-$C_{10}$ alkylene)-$OC(O)NR^6R^7$, —$NO_2$, —$NR^6R^7$, —($C_1$-$C_{10}$ alkylene)-$NR^6R^7$, —O—($C_2$-$C_{10}$ alkylene)-$NR^6R^7$, —$NR^6C(O)R^7$, —$NR^6C(O)OR^9$, —$NR^6C(O)NR^7R^8$, —$NR^6S(O)_{0-2}R^9$, —N(S(O)$_{0-2}R^9$)$_2$, —$CHNOR^6$, —$C(O)NR^6R^7$, —C(O)$NR^6NR^6R^7$, —$S(O)_{0-2}NR^6R^7$, —$S(O)_{0-2}R^9$, —O—C(O)—($C_1$-$C_{10}$ alkylene)-$C(O)NR^6R^7$, —OC(O)—($C_1$-$C_{10}$ alkylene)-$NR^6C(O)O$-(alkylaryl), —P(O)(O$R^{10}$)$_2$, —($C_1$-$C_{10}$ alkylene)-OSi(alkyl)$_3$, —$CF_3$, —$OCF_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

$Q^4$ is 1 to 5 substituents independently selected from the group consisting of alkyl, alkenyl, alkynyl, -G, —($C_1$-$C_{30}$ alkylene)-G, —$OR^6$, —($C_1$-$C_{10}$ alkylene)-$OR^6$, —$C(O)R^6$, —($C_1$-$C_{10}$ alkylene)-$C(O)R^6$, —$C(O)OR^6$, —($C_1$-$C_{10}$ alkylene)-C(O)$OR^6$, —$OC(O)R^6$, —($C_1$-$C_{10}$ alkylene)-$OC(O)R^6$, —$OC(O)OR^9$, —($C_1$-$C_{10}$ alkylene)-OC(O)$OR^9$, —CH=CH—$C(O)R^6$, —CH=CH—C(O)$OR^6$,

—C≡C—C(O)$OR^6$, —C≡C—$C(O)R^6$,

—O—($C_1$-$C_{10}$ alkylene)-$OR^6$, —O—($C_1$-$C_{10}$ alkylene)-$C(O)R^6$, —O—($C_1$-$C_{10}$ alkylene)-C(O)$OR^6$, —CN, —O—($C_1$-$C_{10}$ alkylene)-$C(O)NR^6R^7$; —O—C(O)$NR^6NR^7C(O)OR^6$, —O—($C_1$-$C_{10}$ alkylene)-C(O) $NR^6NR^7C(O)OR^6$, —O—($C_1$-$C_{10}$ alkylene)-C(O)(aryl)-$N_3$, —OC(O)—($C_1$-$C_{10}$ alkylene)-C(O)$OR^6$, —$C(O)NR^6R^7$, —($C_1$-$C_{10}$ alkylene)-$C(O)NR^6R^7$, —$OC(O)NR^6R^7$, —($C_1$-$C_{10}$ alkylene)-$OC(O)NR^6R^7$, —$NO_2$, —$NR^6R^7$, —($C_1$-$C_{10}$ alkylene)-$NR^6R^7$, —O—($C_2$-$C_{10}$ alkylene)-$NR^6R^7$, —$NR^6C(O)R^7$, —$NR^6C(O)OR^9$, —$NR^6C(O)NR^7R^8$, —$NR^6S(O)_{0-2}R^9$, —N(S(O)$_{0-2}R^9$)$_2$, —$CHNOR^6$, —$C(O)NR^6R^7$, —C(O)$NR^6NR^6R^7$, —$S(O)_{0-2}NR^6R^7$, —$S(O)_{0-2}R^9$, —O—C(O)—($C_1$-$C_{10}$ alkylene)-$C(O)NR^6R^7$, —OC(O)—($C_1$-$C_{10}$ alkylene)-$NR^6C(O)O$-(alkylaryl), —P(O)(O$R^{10}$)$_2$, —($C_1$-$C_{10}$ alkylene)-OSi(alkyl)$_3$, —$CF_3$, —$OCF_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

$Q^5$ is 1 to 5 substituents independently selected from the group consisting of alkyl, alkenyl, alkynyl, -G, —($C_1$-$C_{30}$ alkylene)-G, —$OR^6$, —($C_1$-$C_{10}$ alkylene)-$OR^6$, —C(O)$R^6$—($C_1$-$C_{10}$ alkylene)-C(O)$R^6$, —C(O)$OR^6$, —($C_1$-$C_{10}$ alkylene)-C(O)$OR^6$, —OC(O)$R^6$, —($C_1$-$C_{10}$ alkylene)-OC(O)$R^6$, —OC(O)$OR^9$, —($C_1$-$C_{10}$ alkylene)-OC(O)$OR^9$, —CH=CH—C(O)$R^6$, —CH=CH—C(O)$OR^6$,

—C≡C—C(O)$OR^6$, —C≡C—C(O)$R^6$,

—O—($C_1$-$C_{10}$ alkylene)-$OR^6$, —O—($C_1$-$C_{10}$ alkylene)-C(O)$R^6$, —O—($C_1$-$C_{10}$ alkylene)-C(O)$OR^6$, —CN, —O—($C_1$-$C_{10}$ alkylene)-C(O)$NR^6R^7$, —O—C(O)$NR^6NR^7$C(O)$OR^6$, —O—($C_1$-$C_{10}$ alkylene)-C(O)$NR^6NR^7$C(O)$OR^6$, —O—($C_1$-$C_{10}$ alkylene)-C(O)(aryl)-$N_3$, —OC(O)—($C_1$-$C_{10}$ alkylene)-C(O)$OR^6$, —C(O)$NR^6R^7$, —($C_1$-$C_{10}$ alkylene)-C(O)$NR^6R^7$, —OC(O)$NR^6R^7$, —($C_1$-$C_{10}$ alkylene)-OC(O)$NR^6R^7$, —$NO_2$, —$NR^6R^7$, —($C_1$-$C_{10}$ alkylene)-$NR^6R^7$, —O—($C_2$-$C_{10}$ alkylene)-$NR^6R^7$, —$NR^6$C(O)$R^7$, —$NR^6$C(O)$OR^9$, —$NR^6$C(O)$NR^7R^8$, —$NR^6$S(O)$_{0-2}R^9$, —N(S(O)$_{0-2}R^9$)$_2$, —CHN$OR^6$, —C(O)$NR^6R^7$, —C(O)$NR^6NR^6R^7$, —S(O)$_{0-2}NR^6R^7$, —S(O)$_{0-2}R^9$, —O—C(O)—($C_1$-$C_{10}$ alkylene)-C(O)$NR^6R^7$, —OC(O)—($C_1$-$C_{10}$ alkylene)-$NR^6$C(O)O-(alkylaryl), —P(O)(O$R^{10}$)$_2$, —($C_1$-$C_{10}$ alkylene)-OSi(alkyl)$_3$, —$CF_3$, —$OCF_3$, halo, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, heterocyclylcarbonylalkoxy and -L-M;

wherein optionally one or more carbon atoms of the —($C_1$-$C_{30}$ alkylene)- radical of $Q^1$, $Q^2$, $Q^3$, $Q^4$ and $Q^5$ is independently replaced by —O—, —C(O)—, —CH=CH—,

—C≡C—,

—N(alkyl)-, —N(alkylaryl)- or —NH—;

G is selected from the group consisting of a sugar residue, disugar residue, trisugar residue, tetrasugar residue, sugar acid, and amino sugar, wherein optionally the sugar residue, disugar residue, trisugar residue, tetrasugar residue, sugar acid, or amino sugar of G is substituted with -L-M;

L is selected from the group consisting of

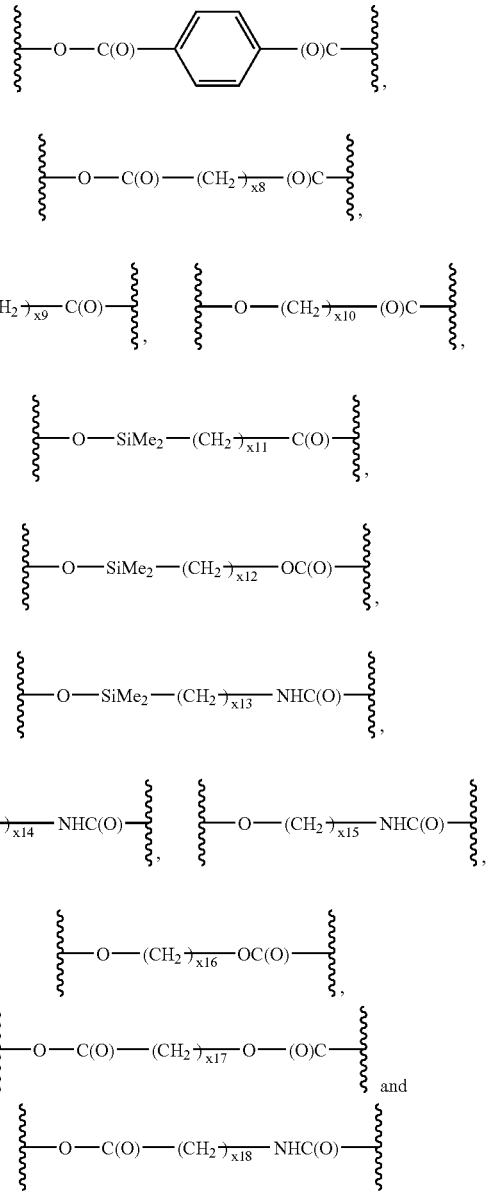

wherein Me is methyl;

M is selected from the group of moieties consisting of

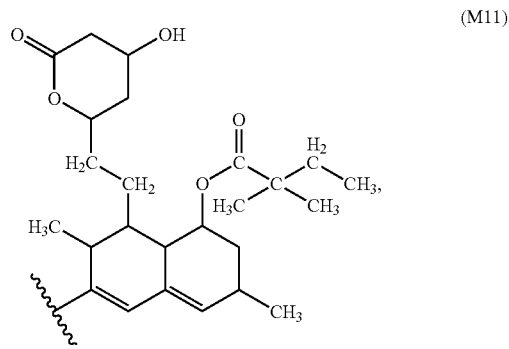

(M11)

-continued
(M12)
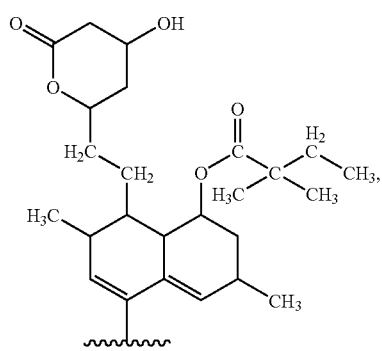
(M13)
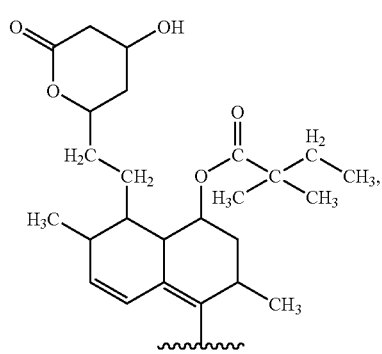
(M14)
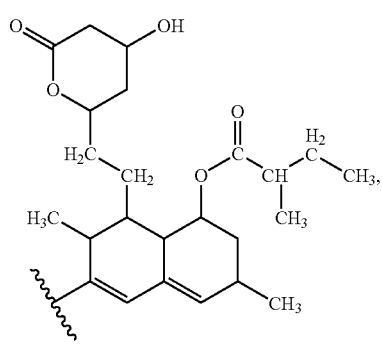
(M15)
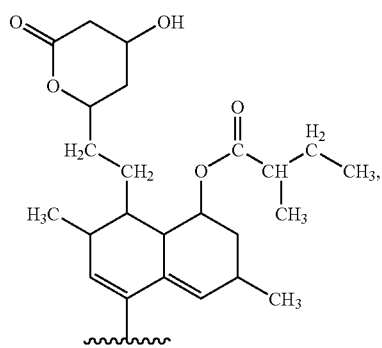
-continued
(M16)
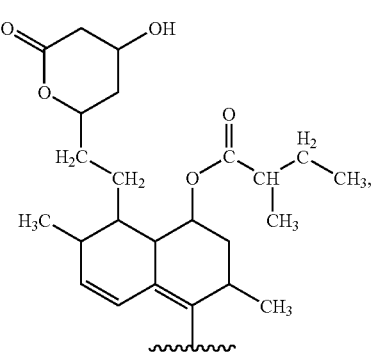
(M17)
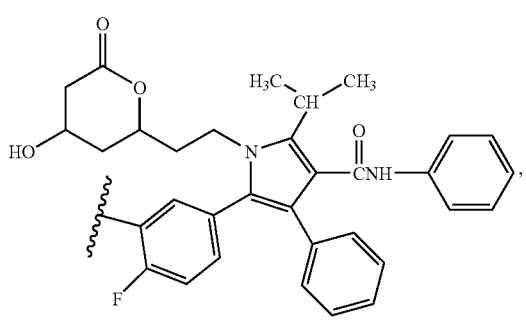
(M19)
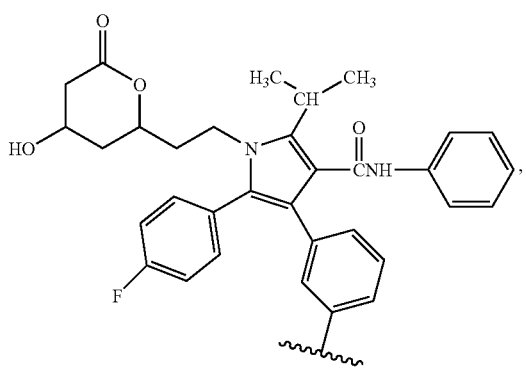
(M20)
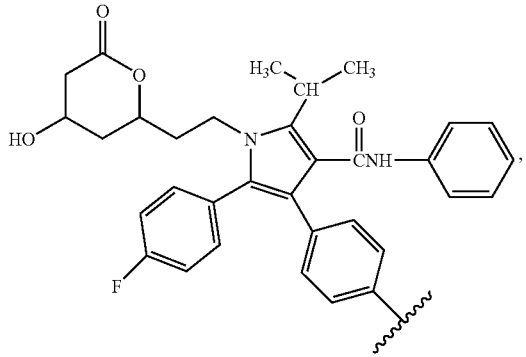

-continued
(M21) 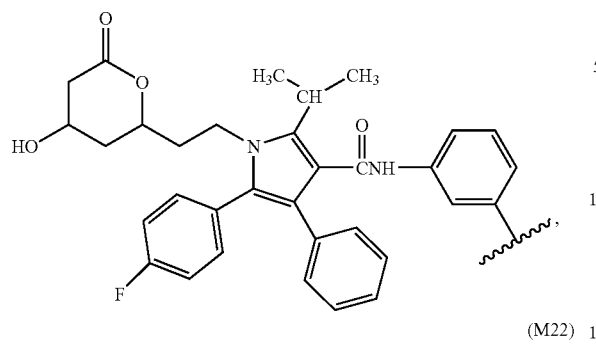
(M22) 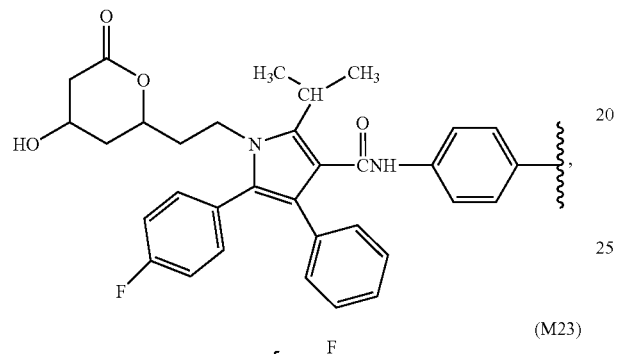
(M23) 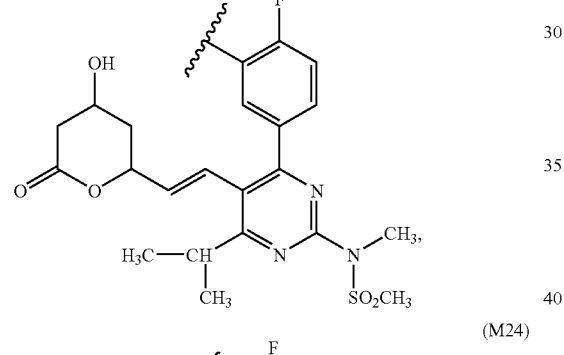
(M24) 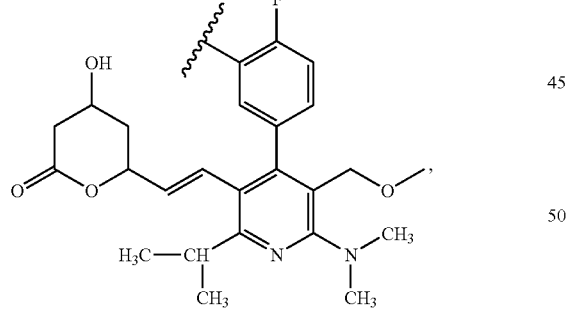
(M25) 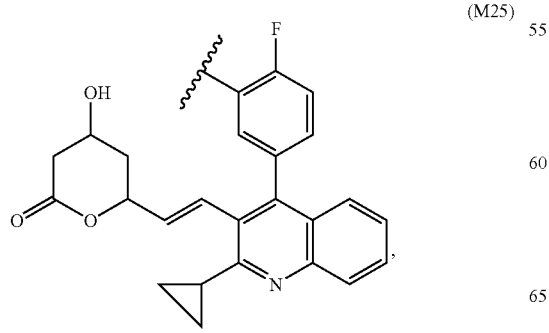
-continued
(M26) 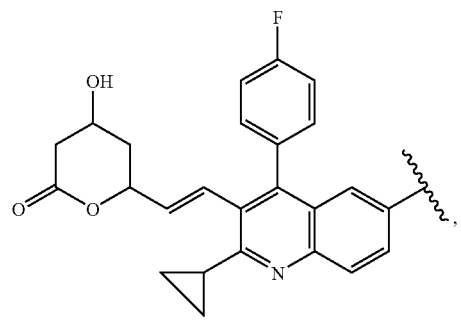
(M27) 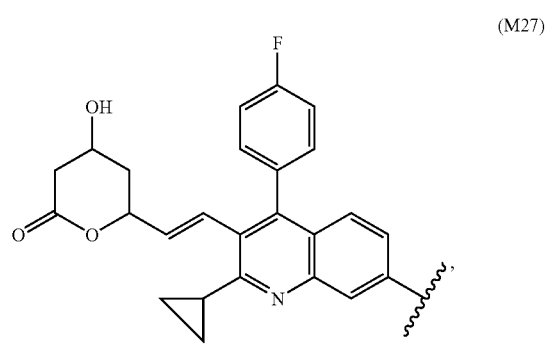
(M28) 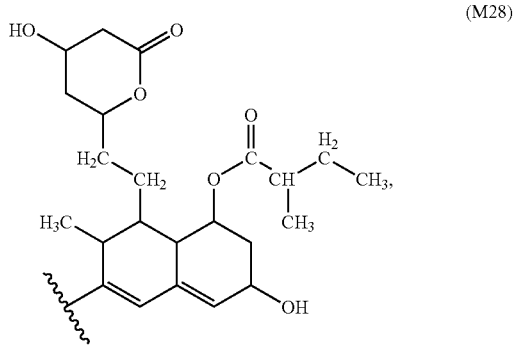
(M29) 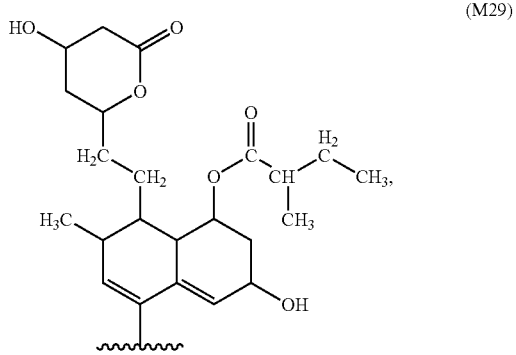

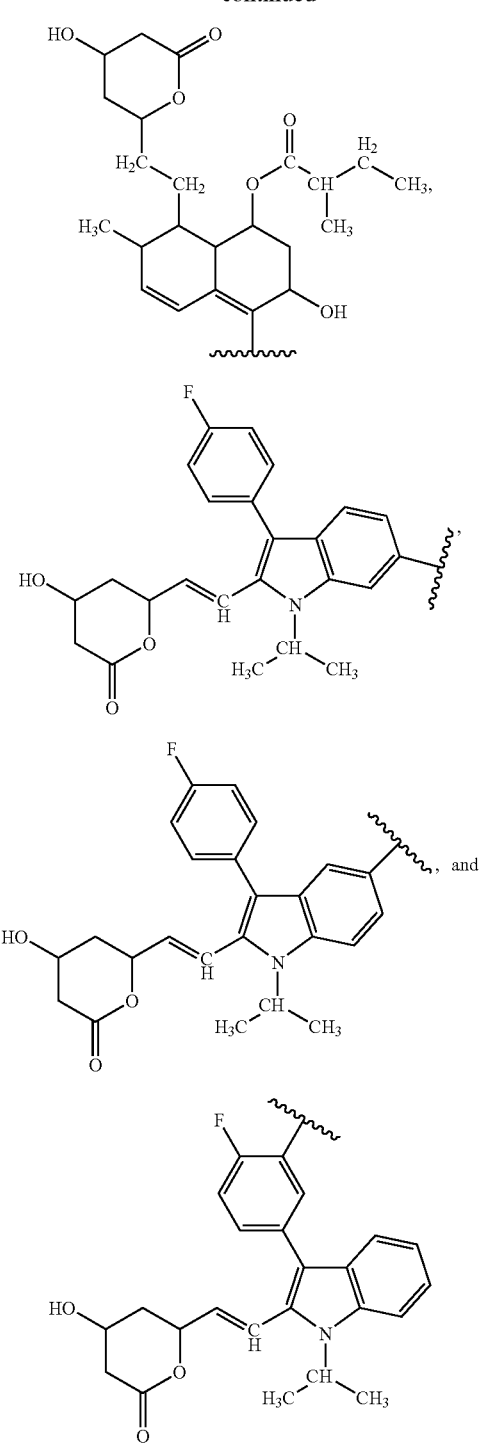

and pharmaceutically acceptable salts of moieties (M1) to (M33);

R² and R³ can be the same or different and each is independently selected from the group consisting of hydrogen, alkyl and aryl;

R⁶, R⁷ and R⁸ can be the same or different and each is independently selected from the group consisting of hydrogen, alkyl, aryl and arylalkyl; and each R⁹ is independently alkyl, aryl or arylalkyl, each $R^{10}$ is independently H or alkyl;

q is 0 or 1;

r is 0 or 1;

m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

x8 is 1 to 10;
x9 is 1 to 10;
x10 is 1 to 10;
x11 is 1 to 10;
x12 is 1 to 10;
x13 is 1 to 10;
x14 is 1 to 10;
x15 is 1 to 10; and
x16 is 1 to 10;
x17 is 1 to 10; and
x18 is 1 to 10;

with the proviso that at least one of $Q^1$, $Q^2$, $Q^3$, $Q^4$ and $Q^5$ is the sugar residue, disugar residue, trisugar residue, tetrasugar residue, sugar acid, or amino sugar of G is substituted with -L-M, and wherein each of the above alkyl, alkenyl, alkynyl, alkylene, alkoxyalkoxy, alkoxyalkoxyalkoxy, alkoxycarbonylalkoxy, alkoxyarylalkoxy, alkoxyiminoalkyl, alkyldioyl, allyloxy, aryl, arylalkyl, aryloxy, arylalkoxy, aroyl, aroyloxy, aroylaroyloxy, arylalkoxycarbonyl, benzoylbenzoyloxy, heteroaryl, heteroarylalkyl, heteroarylalkoxy, dioxolanyl, heterocyclyl, heterocyclylalkyl, heterocyclylcarbonyl, or heterocyclylcarbonylalkoxy groups when present, is independently substituted or unsubstituted.

18. The compound according to claim 17, wherein m, n and r are each zero, q is 1, p is 2, and Z is —CH₂—.

19. The compound according to claim 17, wherein m, n and r are each zero, q is 1, p is 2, and Z is —CH₂—, $Q^1$ is —OR⁶, wherein R⁶ is hydrogen and $Q^5$ is fluorine.

20. The compound according to claim 17, wherein R² and R³ are each hydrogen.

21. The compound according to claim 17, wherein $Q^1$ and $Q^2$ are each independently selected from the group consisting of —OR⁶, —O(CO)R⁶, —O(CO)OR⁹ and —O(CO)NR⁶R⁷.

22. The compound according to claim 17, wherein $Q^4$ is halo or —OR⁶.

23. The compound according to claim 17, wherein $Q^1$ is —OR⁶ wherein R⁶ is H.

24. The compound according to claim 17, wherein $Q^1$, $Q^2$, $Q^3$, $Q^4$ or $Q^5$ is -L-M.

25. The compound according to claim 17, wherein $Q^1$, $Q^2$, $Q^3$, $Q^4$ or $Q^5$ is —(C₁-C₃₀ alkylene)-G.

26. The compound according to claim 17, wherein G is selected from the group consisting of:

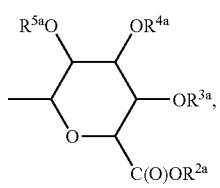 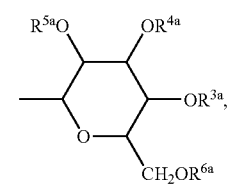

-continued

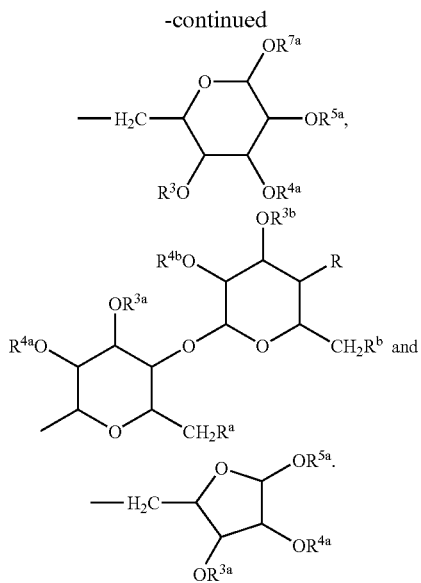

wherein R, $R^a$ and $R^b$ can be the same or different and each is independently selected from the group consisting of H, —OH, halo, —NH$_2$, azido, alkoxyalkoxy or —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

$R^{2a}$ and $R^{6a}$ can be the same or different and each is independently selected from the group consisting of H, alkyl, acetyl, aryl and arylalkyl;

$R^{3a}$, $R^{4a}$, $R^{5a}$, $R^{7a}$, $R^{3b}$ and $R^{4b}$ can be the same or different and each is independently selected from the group consisting of H, alkyl, acetyl, arylalkyl, —C(O)alkyl and —C(O)aryl;

$R^{30}$ is independently selected from the group consisting of $R^{32}$-substituted T, $R^{32}$-substituted-T-alkyl, $R^{32}$-substituted-alkenyl, $R^{32}$-substituted-alkyl, $R^{32}$-substituted-cycloalkyl and $R^{32}$-substituted-cycloalkylalkyl;

$R^{31}$ is independently selected from the group consisting of H and alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is 1 to 3 substituents which are each independently selected from the group consisting of H, halo, alkyl, —OH, phenoxy, —CF$_3$, —NO$_2$, alkoxy, methylenedioxy, oxo, alkylsulfanyl, alkylsulfinyl, alkylsulfonyl, —N(CH$_3$)$_2$, —C(O)—NHalkyl, —C(O)—N(alkyl)$_2$, —C(O)-alkyl, —C(O)-alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a alkoxycarbonyl-substituted pyrrolidinyl, piperidinyl, N-methylpiperazinyl, indolinyl or morpholinyl group.

27. The compound according to claim 26, wherein G is selected from:

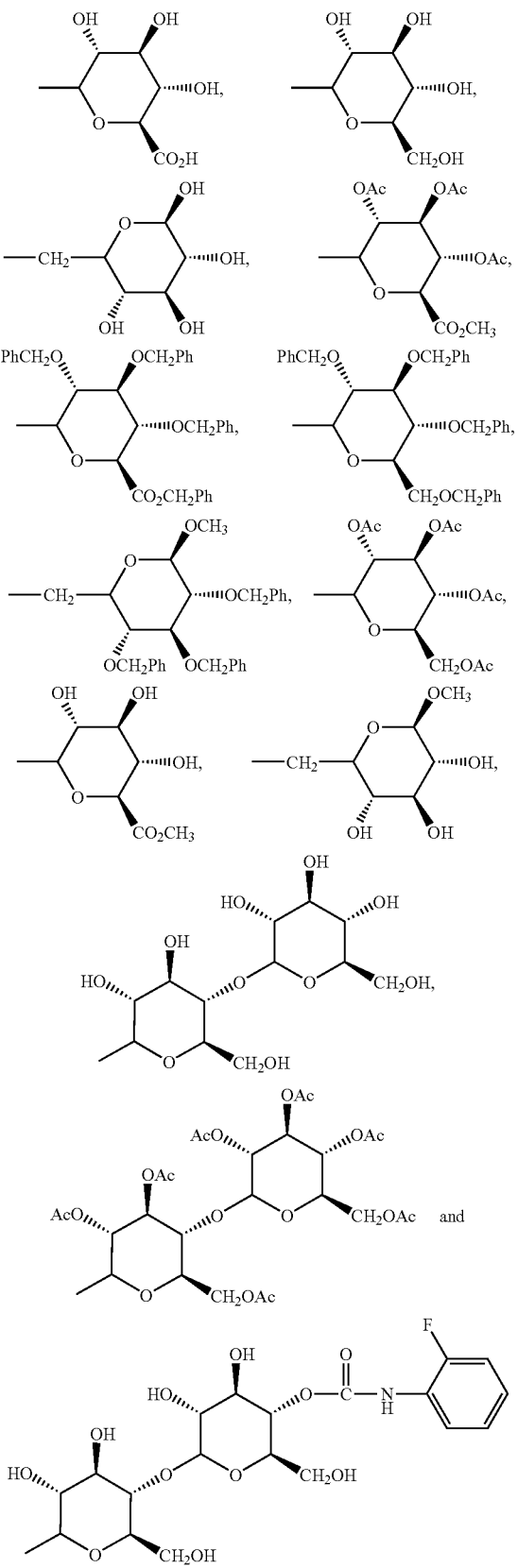

wherein Ac is acetyl and Ph is phenyl.

28. The compound according to claim 17, wherein optionally one or more carbon atoms of the —($C_1$-$C_{30}$ alkylene)-radical of $Q^1$, $Q^2$, $Q^3$, $Q^4$ and $Q^5$ is independently replaced by —O—.

29. A pharmaceutical composition for the treatment of atherosclerosis, hypercholesterolemia, sitosterolemia, lowering a concentration of cholesterol, phytosterol or 5α-stanol in plasma of a subject comprising a therapeutically effective amount of a compound of claim 17 in a pharmaceutically acceptable carrier.

30. A pharmaceutical composition comprising a cholesterol-lowering effective amount of a compound of claim 17 in a pharmaceutically acceptable carrier.

31. A method of treating atherosclerosis, hypercholesterolemia, sitosterolemia, lowering a concentration of cholesterol, phytosterol or 5α-stanol in plasma of a subject comprising the step of administering to a subject in need of such treatment an effective amount of a compound of claim 17.

32. A method of lowering cholesterol level in plasma of a mammal in need of such treatment comprising administering a pharmaceutically effective amount of the compound of claim 17.

* * * * *

UNITED STATES PATENT AND TRADEMARK OFFICE
CERTIFICATE OF CORRECTION

| | | |
|---|---|---|
| PATENT NO. | : 7,368,562 B2 | Page 1 of 1 |
| APPLICATION NO. | : 11/705977 | |
| DATED | : May 6, 2008 | |
| INVENTOR(S) | : Duane A. Burnett and John W. Clader | |

It is certified that error appears in the above-identified patent and that said Letters Patent is hereby corrected as shown below:

Claim 10, col. 49, line 40      Please correct "$NH^2$" to -- $NH_2$ --

Signed and Sealed this

Sixth Day of January, 2009

JON W. DUDAS
*Director of the United States Patent and Trademark Office*